US011685735B2

(12) United States Patent
Liu

(10) Patent No.: US 11,685,735 B2
(45) Date of Patent: Jun. 27, 2023

(54) PHARMACEUTICAL COMPOSITION COMPRISING BERBERINE SALTS FOR THE TREATMENT OF VARIOUS DISEASES OR DISORDERS

(71) Applicant: SHENZHEN HIGHTIDE BIOPHARMACEUTICAL, LTD., Shenzhen (CN)

(72) Inventor: Liping Liu, Manassas, VA (US)

(73) Assignee: Shenzhen HighTide Biopharmaceutical, Ltd., Shenzhen (CN)

( * ) Notice: Subject to any disclaimer, the term of this patent is extended or adjusted under 35 U.S.C. 154(b) by 145 days.

(21) Appl. No.: 17/204,776

(22) Filed: Mar. 17, 2021

(65) Prior Publication Data

US 2021/0300915 A1 Sep. 30, 2021

Related U.S. Application Data

(60) Continuation of application No. 16/351,819, filed on Mar. 13, 2019, now Pat. No. 10,988,471, which is a division of application No. 15/303,468, filed as application No. PCT/CN2015/085350 on Jul. 28, 2015, now Pat. No. 10,301,303.

(60) Provisional application No. 62/030,140, filed on Jul. 29, 2014, provisional application No. 62/030,147, filed on Jul. 29, 2014, provisional application No. 62/128,077, filed on Mar. 4, 2015.

(51) Int. Cl.
| | |
|---|---|
| *A61K 31/4375* | (2006.01) |
| *C07D 221/18* | (2006.01) |
| *C07D 455/03* | (2006.01) |
| *C07D 471/14* | (2006.01) |
| *A61K 31/4745* | (2006.01) |

(52) U.S. Cl.
CPC ........ *C07D 455/03* (2013.01); *A61K 31/4375* (2013.01); *A61K 31/4745* (2013.01); *C07D 471/14* (2013.01)

(58) Field of Classification Search
CPC .......................... A61K 31/4375; C07D 221/18
USPC ............................................. 514/280; 546/48
See application file for complete search history.

(56) References Cited

U.S. PATENT DOCUMENTS

2013/0273175 A1  10/2013  Finley

FOREIGN PATENT DOCUMENTS

| CN | 1762367   A | 4/2006 |
|---|---|---|
| CN | 101070337 A | 11/2007 |
| CN | 101113149 A | 1/2008 |
| CN | 101879162 A | 11/2010 |
| CN | 101935319 A | 1/2011 |
| CN | 101987860 A | 3/2011 |
| CN | 102076347 A | 5/2011 |
| CN | 102225961 A | 10/2011 |
| CN | 102370643 A | 3/2012 |
| CN | 102078418 B | 4/2012 |
| CN | 102580087 A | 7/2012 |
| CN | 103319479 A | 9/2013 |
| CN | 103989677 A | 8/2014 |
| CN | 102702190 B | 4/2016 |
| EP | 0065666   B | 12/1982 |
| EP | 0510404   B | 10/1992 |
| EP | 2221313   A | 8/2010 |
| FR | 2796551   B | 1/2001 |
| JP | 48028616  A | 4/1973 |
| JP | 06256192  A | 9/1994 |
| KR | 20050081477 A | 8/2005 |
| WO | 2006029577 A | 3/2006 |
| WO | 2014183184 A | 11/2014 |
| WO | 2015183794 A | 12/2015 |

OTHER PUBLICATIONS

PCT/CN2015/085350, International Search Report, dated Sep. 24, 2015.
PCT/CN2015/085350, Written Opinion of the ISA dated Sep. 24, 2015.
CN201580041177.9, Office Action, dated Feb. 13, 2018.
EP15826295.6, Communication Pursuant to Rule 164(1) EPC, dated Feb. 7, 2018.
Basu et al. Journal of Hepatology vol. 60, No. 1, pp. S355-79233, Apr. 1, 2014.
Database WPI, AN2011-H91123, Jun 1, 2011.
Anonymous: Berberine Support, XP55445006, Apr. 1, 2014.
Database WPI, AN 2011-P68227, Oct. 26, 2011.

(Continued)

*Primary Examiner* — Douglas M Willis
(74) *Attorney, Agent, or Firm* — Milstein Zhang & Wu LLC

(57) ABSTRACT

The invention provides various novel compositions of berberine in combination with pharmacologically active organic acids, and related methods of their use in treating various diseases or disorders. The invention further provides various novel compounds prepared from berberine and pharmacologically active organic acids and prepared from ursodeoxycholic acid and pharmacologically active organic bases, and pharmaceutical compositions thereof, and methods of their preparation and therapeutic use in treating and/or preventing various diseases or disorders. The compounds and pharmaceutical compositions of the invention can be utilized to treat various diseases or disorders, such as diabetes, diabetic complications, dyslipidemia, hyperlipidemia, obesity, metabolic syndromes, pre-diabetes, atherosclerosis, heart diseases, neurodegenerative diseases, sarcopenia, muscle atrophy, inflammation, cancer and liver diseases and conditions such as fatty liver, non-alcoholic fatty liver disease, non-alcoholic steatohepatitis, cholestatic liver diseases or graft-versus-host disease of the liver. The compounds of this invention are also useful in improving liver functions in chronic viral associated liver diseases and alcohol-related liver diseases.

12 Claims, 15 Drawing Sheets

(56) References Cited

OTHER PUBLICATIONS

Database WPI, AN 2013-A79535, Oct. 3, 2012.
Inder Pal Singh, Berberine and its derivatives: a patent review, XP55444683, Dec. 12, 2012.
Siqin Gaiowa, et al. Journal of Medicine & Pharmacy of Chinese Minorities No. 1, pp. 49-51, Jan. 31, 2014.
Chalasani, et al. Hepatology vol. 55, No. 6, 2005-2023, Apr. 3, 2012.
EA201790124/ 28, Office Action, dated Jan. 31, 2018.
SG11201700481Y, Written Opinion, dated Jan. 12, 2018.
SG11201700481Y, Search Report, dated Oct. 20, 2017.
EP15826295.6, Communication Pursuant to 94-3, dated Sep. 26, 2019.
JP 2016-564633, Decision of Rejection, dated Aug. 29, 2019.
MX/a/2017/001372, Office Action, dated Jul. 9, 2019.
SG11201700481Y, Written Opinion, dated Jul. 29, 2019.
Vuddanda, et al. Expert Opinion on Investinational Drugs, 19:10, 1297-1307, Sep. 13, 2010.
Rodrigues, et al. Expert Opinion on Investinational Drugs, 10:7, 1243-1253, Feb. 24, 2005.
Svenson "Carrier-Based Drug Delivery" 2004, ACS Symposium Seriesvol. 879; DOI: 10.1021/bk-2004-0879.ch001, May 5, 2004.
Dave "Overview of pharmaceutical excipients used in tablets and capsules", http://drugtopics.modernmedicine.com/drug-topics/news/modernmedicine/modern-medicine-news/overview-pharmaceutical-excipients-used-tablets, Oct. 24, 2008.
Chalasani et al. Am J Gastroenterol 2012; 107: 811-826, May 29, 2012.
Al-masri, et al. J Enzyme Inhib & Med Chem, 24:5, 1061-1066, Jul. 29, 2009.
Liu, et al. Evidence-Based Complementary and Alternative Medicine, 2013(5):308134, Jun. 2013.
Xiang, et al. MBC Gastroenterology 2013, 13:140, Sep. 23, 2013.

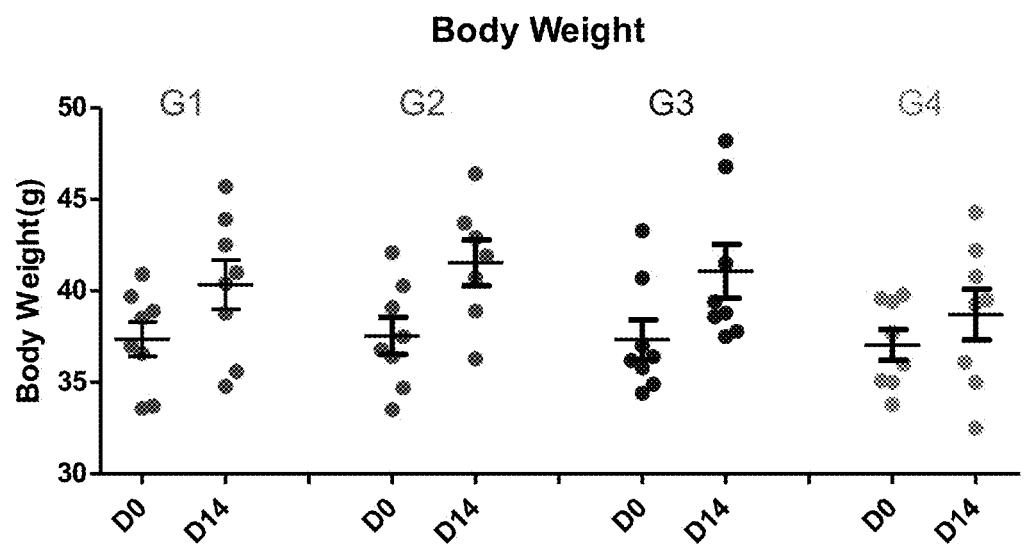
FIG. 1. Body weight of each treatment group at day 0 and day 14.
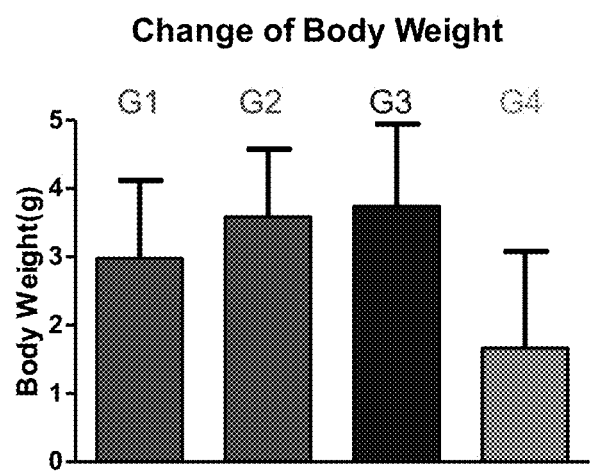
FIG. 2. Change of body weight of each treatment group after 14 days of treatment.

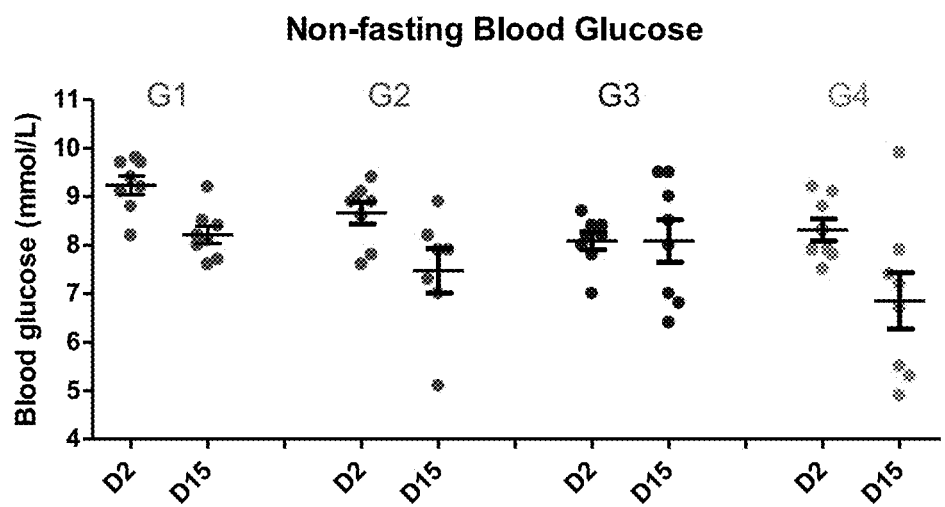
FIG. 3. Blood glucose of each treatment group at day 2 and day 15.
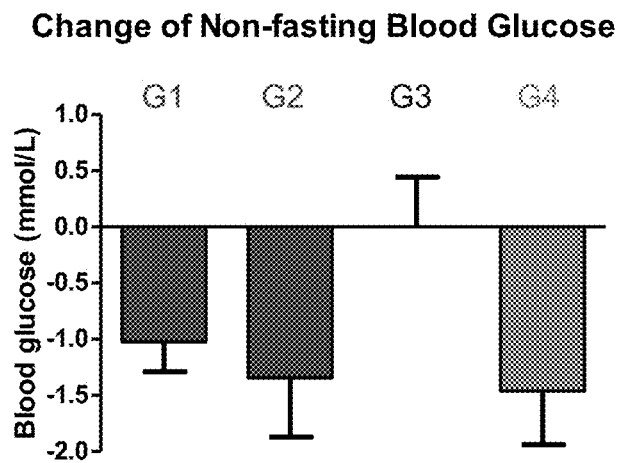
FIG. 4. Change of blood glucose of each treatment group at day 2 and day 15.

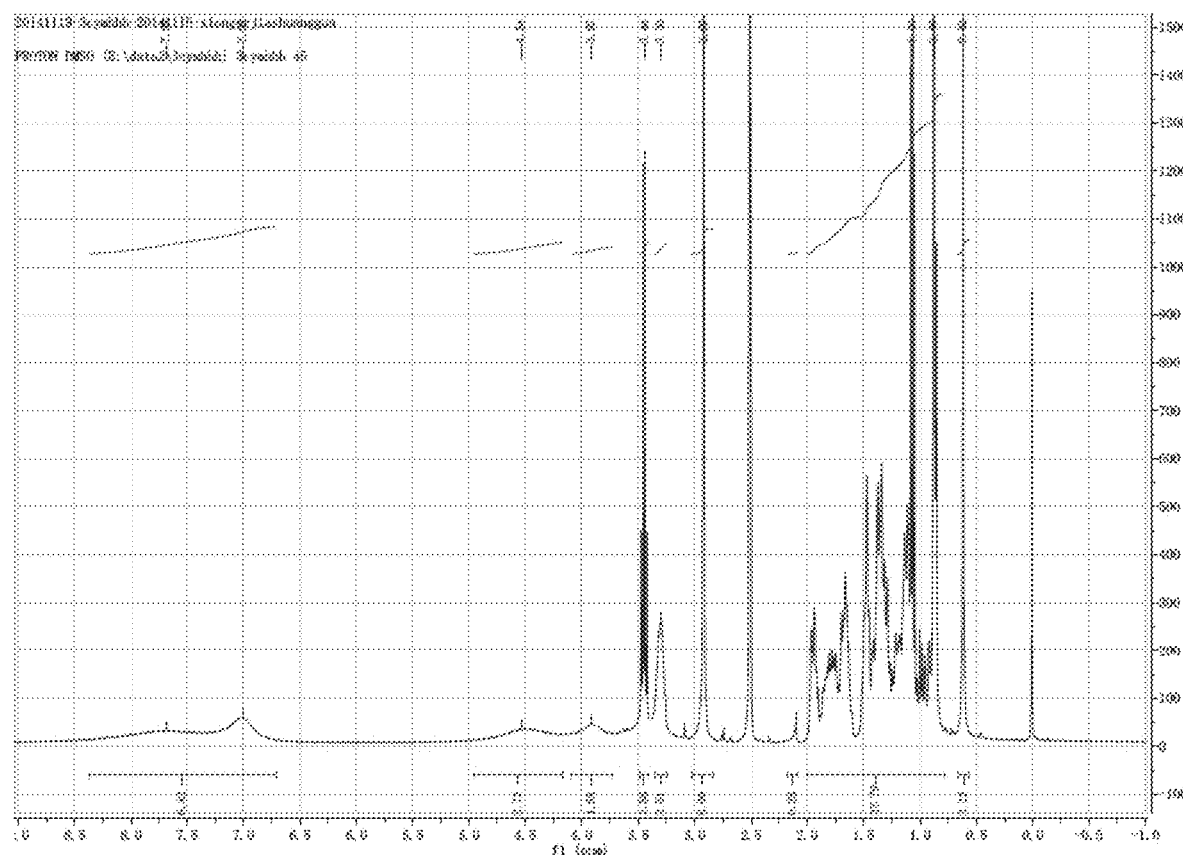
FIG. 5. $^1$H NMR of metformin ursodeoxycholate in DMSO-D6.

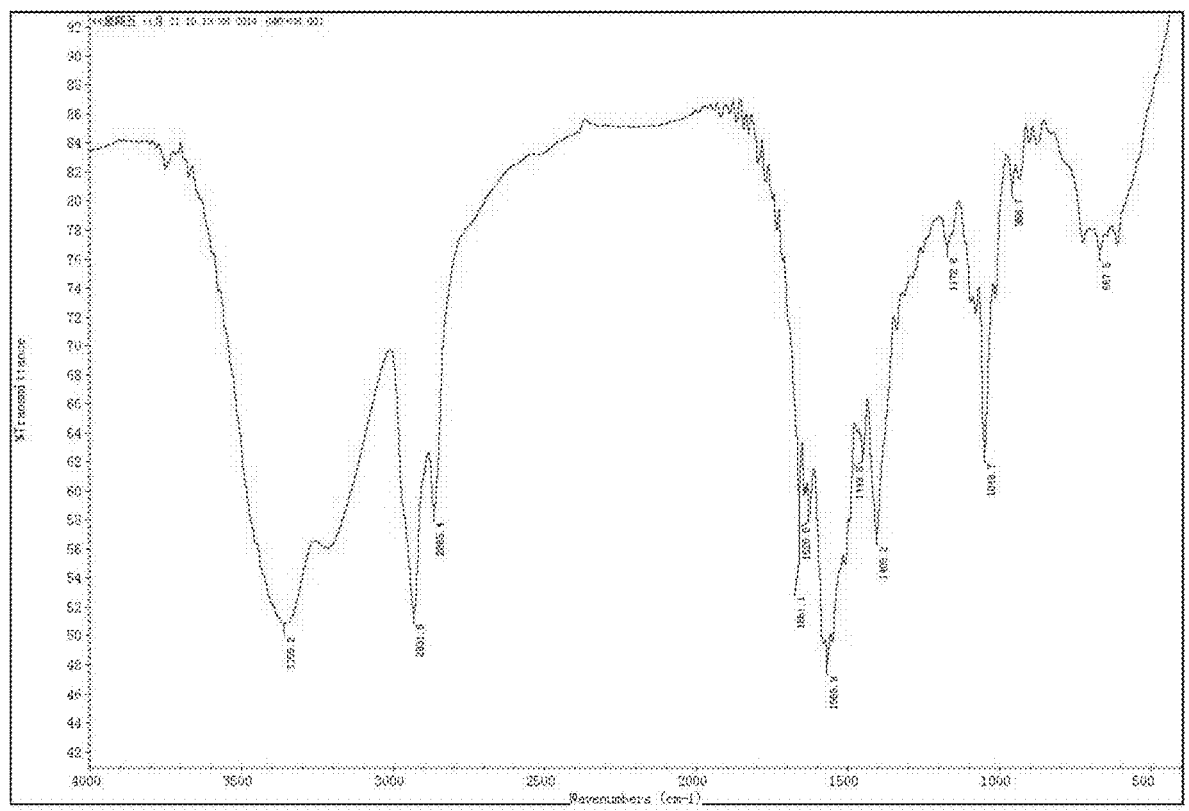
FIG. 6. IR spectrum of metformin ursodeoxycholate.

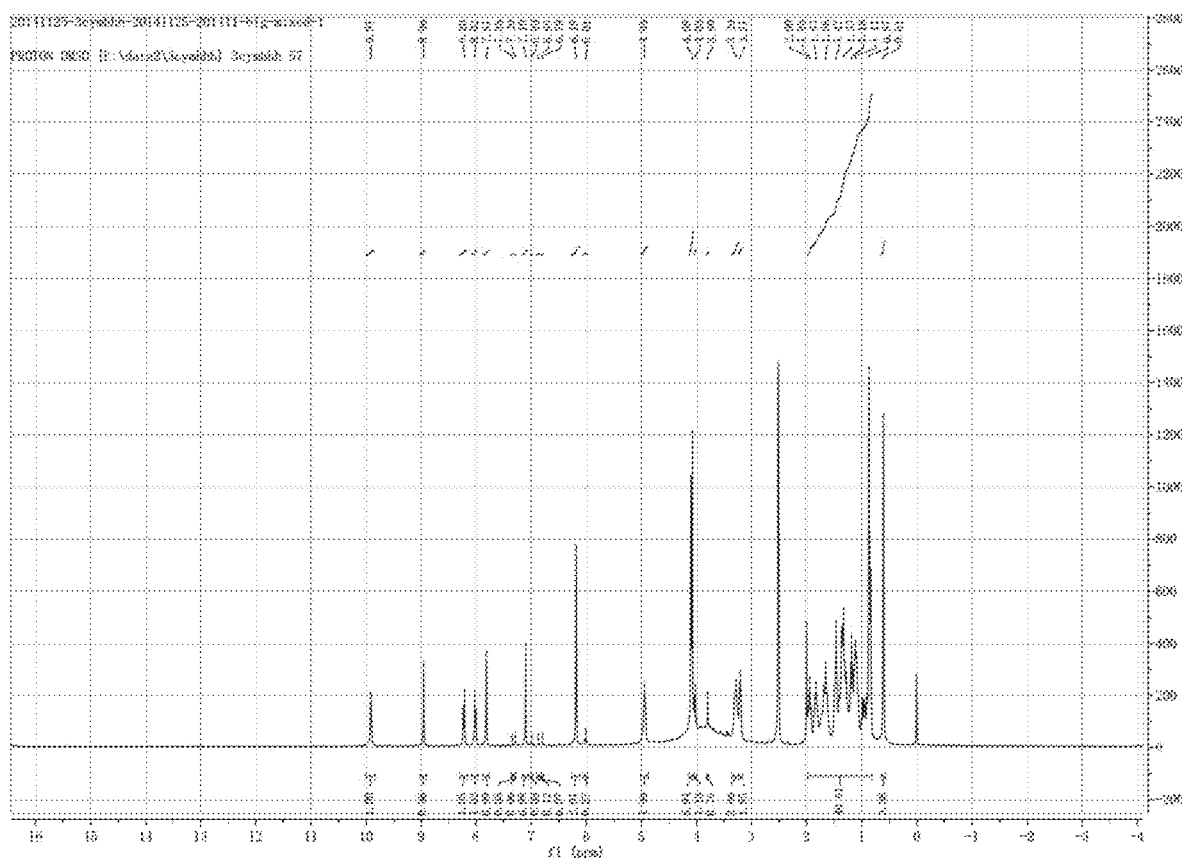
FIG. 7. $^1$H NMR of berberine ursodeoxycholate (purified product).

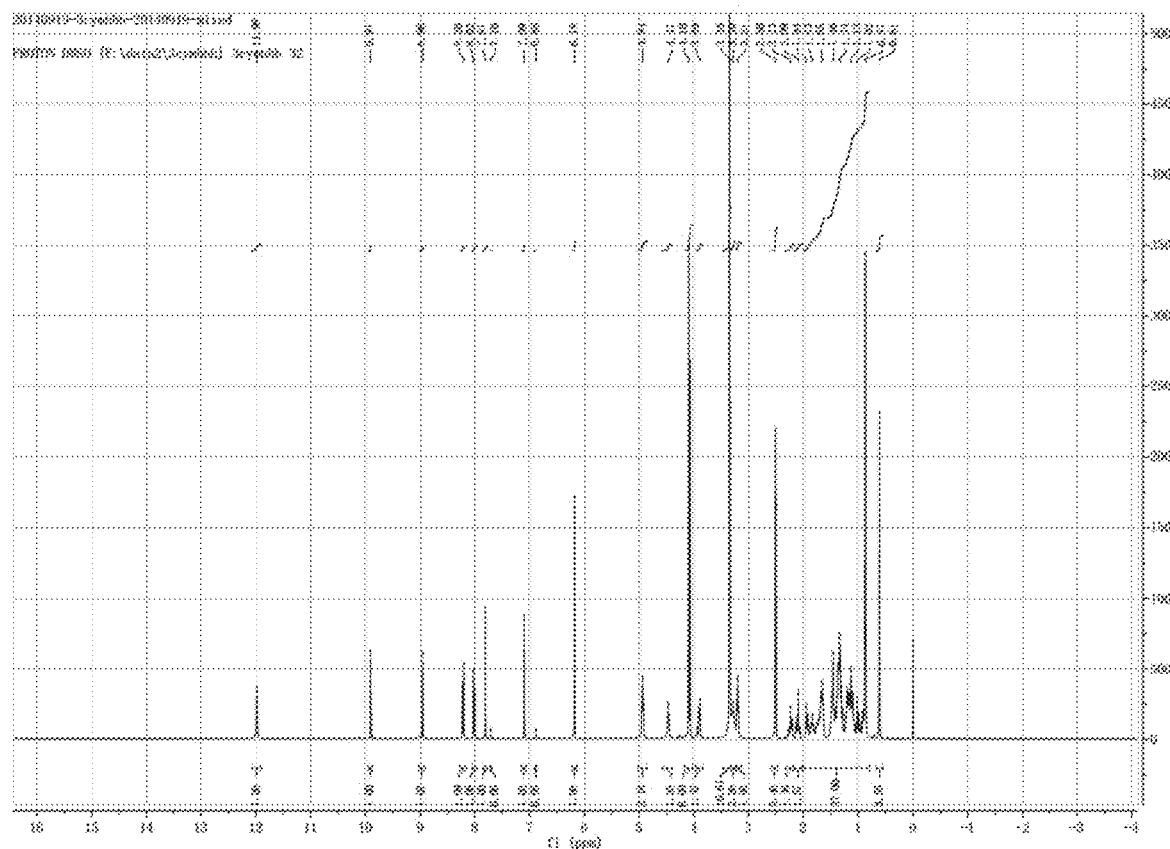
FIG. 8. $^1$H NMR of mixture of berberine hydrochloride (1.0 equiv.) and ursodeoxycholic acid (1.0 equiv.) in DMSO-D6.

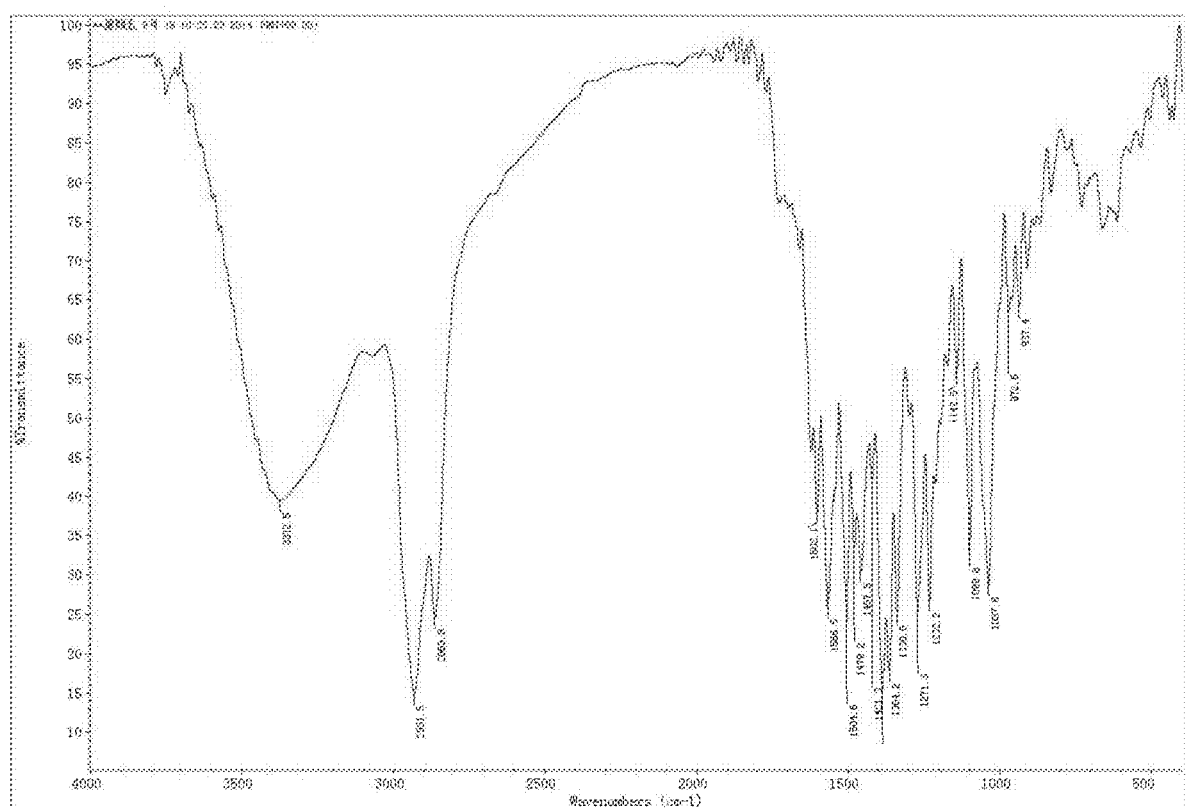
FIG. 9. IR spectrum of berberine ursodeoxycholate (crude product).
The carbonyl stretching vibration band C=O of ursodeoxycholic acid at about 1721 cm$^{-1}$ disappeared in IR spectrum of berberine ursodeoxycholate.

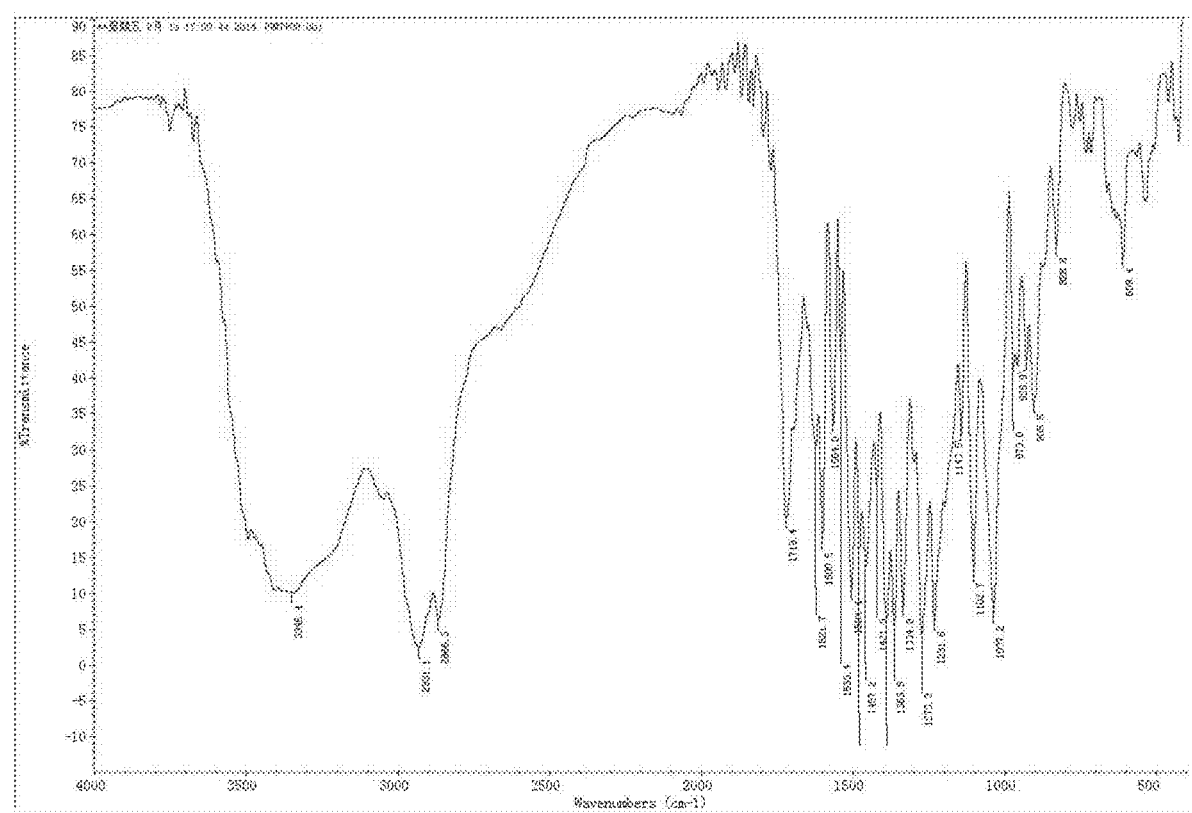
FIG. 10. IR spectrum of mixture of berberine hydrochloride (1.0 equiv.) and ursodeoxycholic acid (1.0 equiv.). The carbonyl stretching vibration band C=O of ursodeoxycholic acid appears at about 1719 cm$^{-1}$.

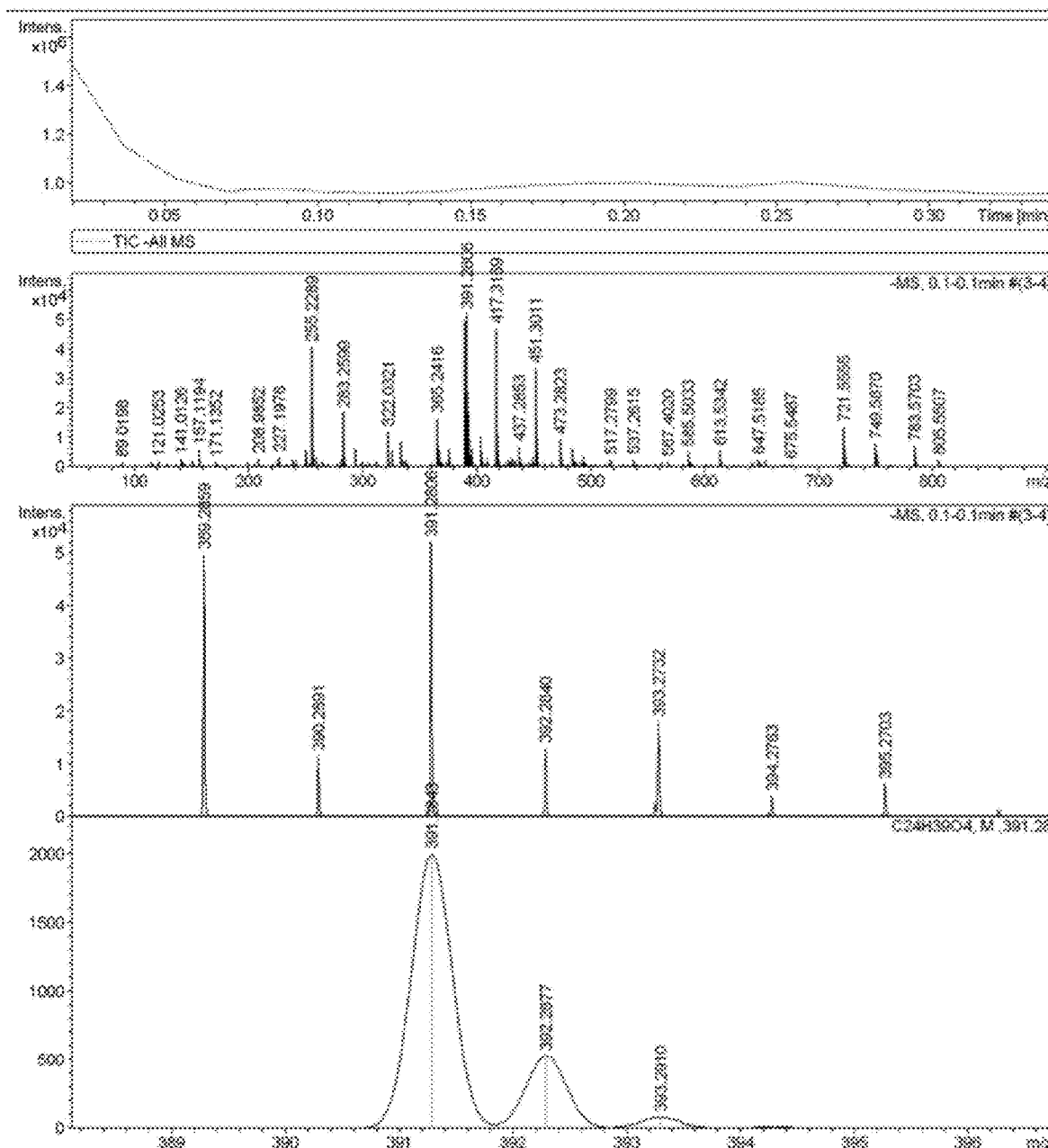
FIG. 11. Mass spectroscopy of berberine ursodeoxycholate: in negative MS mode, molecular mass of UDCA [M-H]⁻ 391.28 was identified.

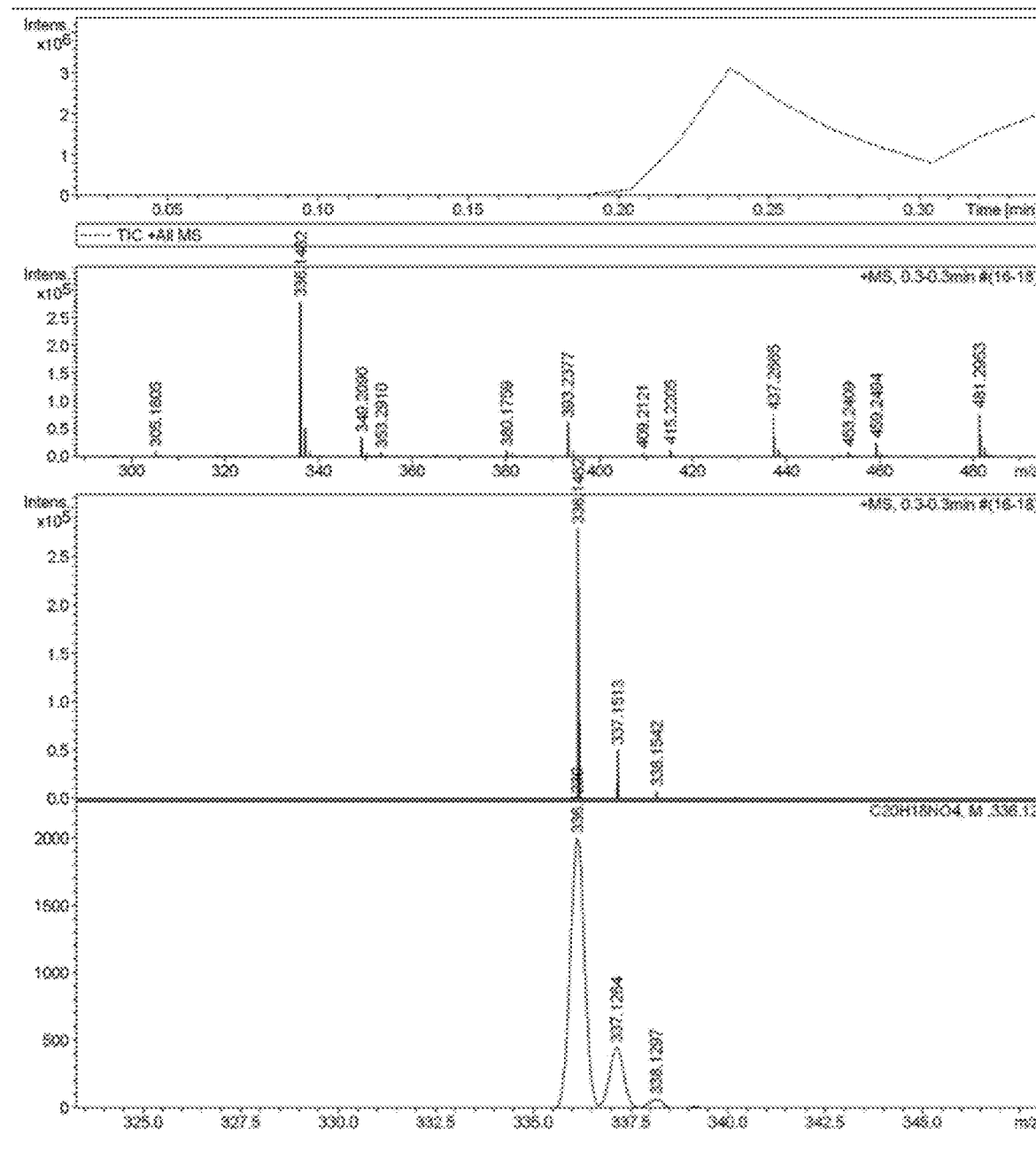
FIG. 12. Mass spectroscopy of berberine ursodeoxycholate: in positive MS mode, molecular mass of BBR[+] 336.14 was identified.

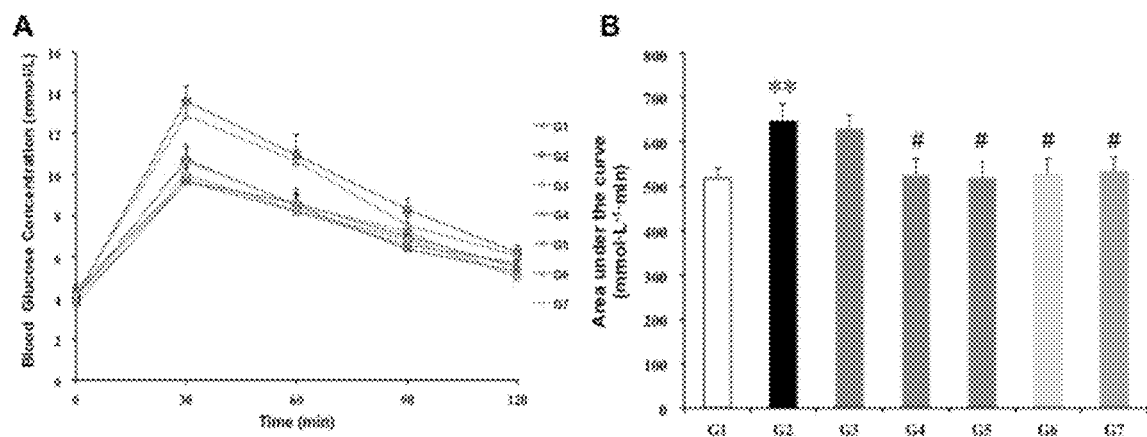
FIG. 13. (A) Plasma glucose concentrations during oral glucose tolerance test (OGTT) and (B) the area under the OGTT glucose curve. Data are expressed as the mean ±S.E.M (n=7~13). ** p<0.01 G2 vs. G1. # p<0.05 G4, G5, G6, or G7 vs. G2.

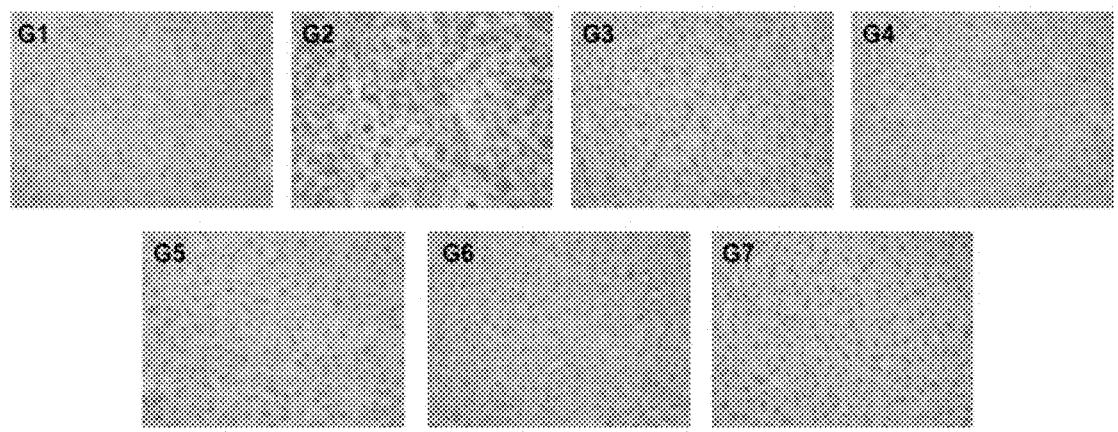
FIG. 14. Image of liver Sultan III staining in various groups (n=7~13).
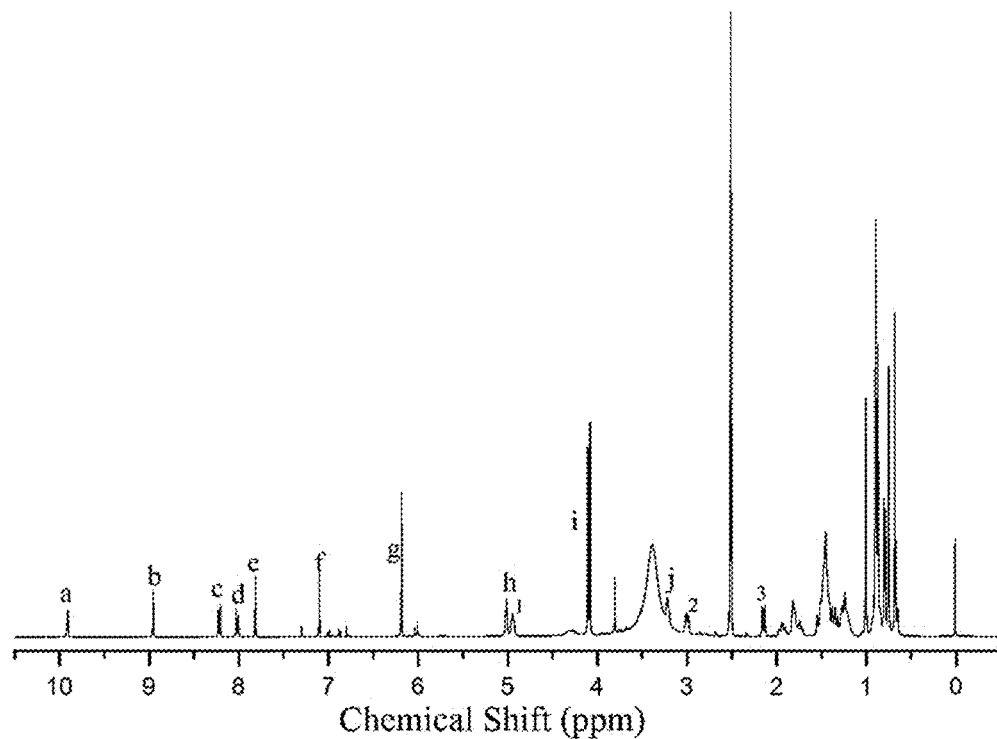
FIG. 15. $^1$H NMR of Berberine ursolic salt (400MHz, DMSO-$d_6$)

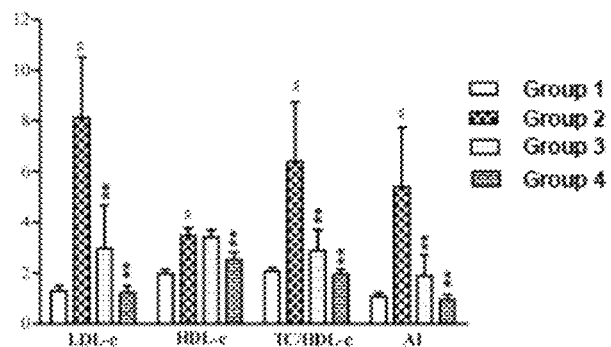
FIG.16. The Effect of BUDCA on Serum LDL-c level, Serum HDL-c level, TC/HDL-c and AI of Hyperlipidemic Hamsters
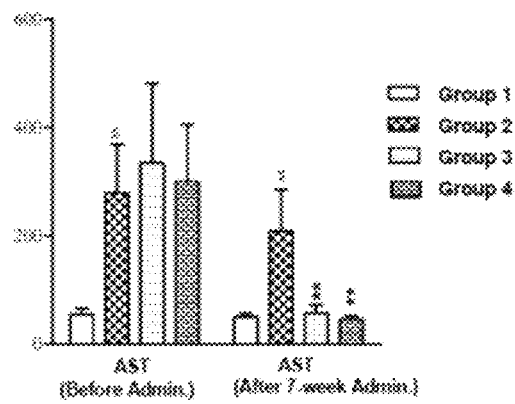
FIG.17. The Effect of BUDCA on Serum AST Level of Hyperlipidemic Hamsters
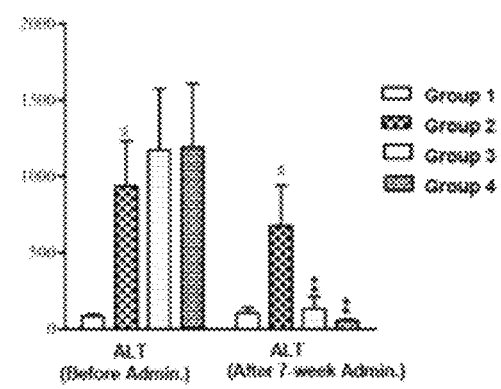
FIG.18. The Effect of BUDCA on Serum ALT Level of Hyperlipidemic Hamsters

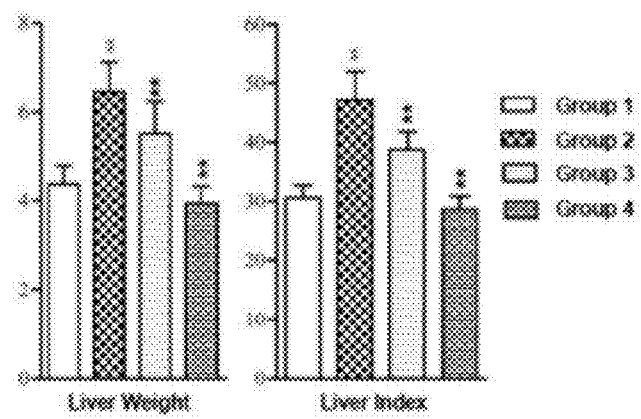
FIG.19. The Effect of BUDCA on Liver Weight and Liver Index of Hyperlipidemic Hamsters
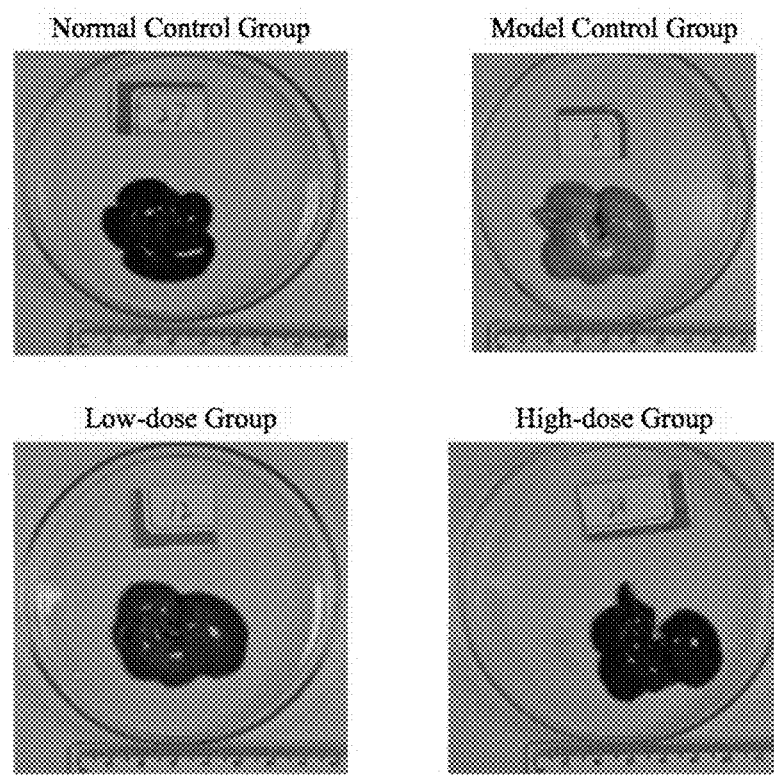
FIG.20. The General Observation of Lipid Deposition in Liver Tissue

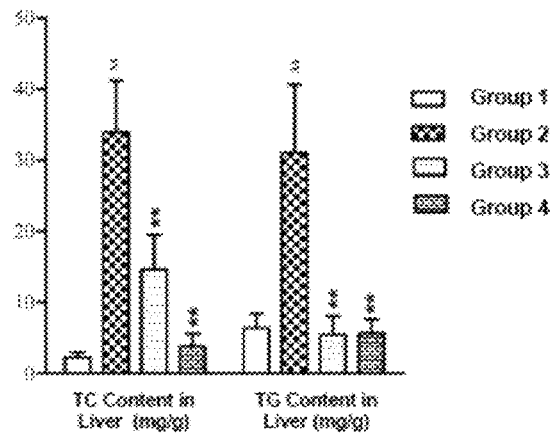
FIG. 21. The Effect of BUDCA on TC and TG Contetn in Livers of Hyperlipidemic Hamsters
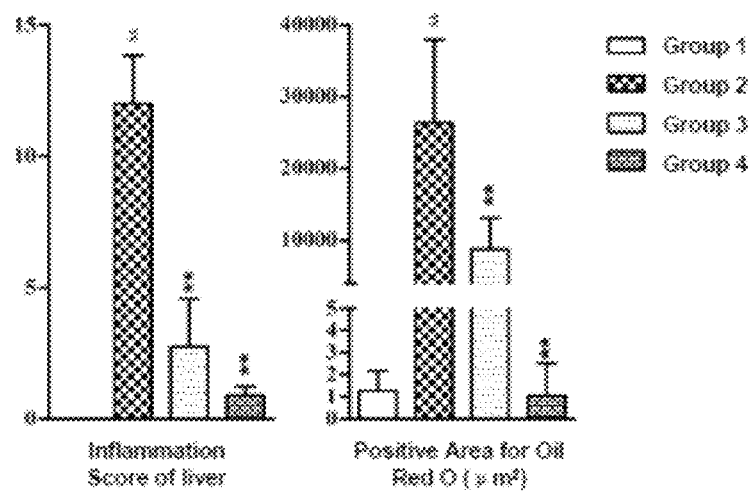
FIG. 22. The Effect of BUDCA on Inflammation Score and Positive Area for Oil Red O

PHARMACEUTICAL COMPOSITION COMPRISING BERBERINE SALTS FOR THE TREATMENT OF VARIOUS DISEASES OR DISORDERS

PRIORITY CLAIMS AND RELATED APPLICATIONS

This application is a continuation of and claims the benefit of priority to U.S. Ser. No. 16/351,819, filed Mar. 13, 2019, which is a divisional of and claims the benefit of priority to U.S. Ser. No. 15/303,468, filed Oct. 11, 2016, which in the national phase and claims priority to PCT/CN2015/085350, filed Jul. 28, 2015, which claims priority to U.S. Provisional Application Nos. 62/030,140 and 62/030,147, each filed Jul. 29, 2014, and U.S. Provisional Application No. 62/128,077, filed Mar. 4, 2015, the entire content of each of which is incorporated herein by reference.

TECHNICAL FIELD OF THE INVENTION

The invention generally relates to novel therapeutic compounds, pharmaceutical compositions, and methods of preparation and therapeutic use thereof.

In particular, the invention relates to novel compositions of berberine in combination with pharmacologically active organic acids, and methods of their use. In particular, the invention also relates to novel salts of berberine and organic acids and novel salts of ursodeoxycholic acid and organic bases, pharmaceutical compositions thereof, methods of their use. The compounds and pharmaceutical compositions of the invention are useful in treating and/or preventing various diseases or disorders, including metabolic diseases or disorders such as pre-diabetes, diabetes, diabetic complications, dyslipidemia, dyslipidemia in statin-intolerance patients, hyperlipidemia, hypercholesterolemia, hypertriglyceridemia, diabetic dyslipidemia, or obesity. Additionally, the compounds and pharmaceutical compositions of the invention are useful in treating and/or preventing atherosclerosis, heart diseases, neurodegenerative diseases, sarcopenia, muscle atrophy, inflammation, cancers, as well as various liver diseases or disorders, such as fatty liver, non-alcoholic fatty liver disease, non-alcoholic steatohepatitis, cholestatic liver diseases or graft-versus-host disease of the liver. Furthermore, the compounds and pharmaceutical compositions of the invention are useful in improving liver functions in chronic viral associated liver diseases and alcohol-related liver diseases.

BACKGROUND OF THE INVENTION

Diabetes mellitus is a disorder of metabolism. It has become pandemic with an estimate of over 300 million people worldwide living with diabetes today. Without effective prevention, this number will grow up to 500 million by 2030. There are three main types of diabetes: type 1 diabetes, type 2 diabetes, and gestational diabetes. Among them, type 2 diabetes, is the most common form of diabetes accounting for 90-95% of cases. Type 2 diabetes is characterized by impaired insulin secretion, increased hepatic glucose production, and decreased response of peripheral tissues to insulin, i.e., insulin resistance. Many therapeutic treatments are available for the management of type 2 diabetes, but they are often accompanied by various side effects. An optimal therapy should be safe and include early initiation of combination drugs with complimentary mechanisms of action.

Despite persistent efforts and meaningful progress over the past decades in the understanding and management of diabetes, people with diabetes continue to have an increased risk of, and many do suffer from, a number of serious complications inflicting the heart and blood vessels, eyes, kidneys, and nerves due to high blood glucose, high cholesterol, and high blood pressure. Cardiovascular diseases are the most common cause of death in people with diabetes. Diabetic nephropathy caused by damages to small blood vessels in the kidney leads to decreased kidney function or kidney failure altogether. Diabetic neuropathy is caused by damages to the nerves throughout the body when blood glucose level and blood pressure are too high. Most people with diabetes develop diabetic retinopathy causing reduced vision or blindness. Consistently high levels of blood glucose, together with high blood pressure and high cholesterol, are the main causes of diabetic retinopathy. Despite the development of a number of anti-diabetic agents, there are significant unmet needs for therapeutics that can be used effectively for the treatment and management of diabetic complications.

Metabolic syndrome is a term that refers to a group of risk factors that occur together (e.g., abdominal (central) obesity, elevated blood pressure, elevated fasting plasma glucose, high serum triglycerides, and low high-density cholesterol (HDL) levels). Metabolic syndrome has been demonstrated to increase the risk of developing cardiovascular diseases, particularly heart failure, and diabetes. Studies have estimated that the prevalence of metabolic syndromes in the US to be around 34% in the adult population. While therapeutics are available, the first line treatment is change of lifestyle. High-dose statins, recommended to reduce cardiovascular risks, have been linked to higher progression to diabetes, especially in patients with metabolic syndrome.

Dyslipidemia is a disorder of lipoprotein metabolism, including lipoprotein overproduction (hyperlipidemia) or deficiency. Dyslipidemias may be manifested by elevation of the total cholesterol, the "bad" low-density lipoprotein cholesterol and the triglyceride concentrations, and a decrease in the "good" high-density lipoprotein cholesterol concentration in the blood. Dyslipidemia comes under consideration in many situations including diabetes, a common cause of dyslipidemia. Hyperlipidemia is elevation of plasma cholesterol (hypercholesterolemia), triglycerides (hypertriglyceridemia), or both, or a low high-density lipoprotein level that contributes to the development of atherosclerosis. Causes may be primary (genetic) or secondary. Diagnosis is by measuring plasma levels of total cholesterol, TGs, and individual lipoproteins. Treatment involves dietary changes, exercise, and lipid-lowering drugs.

Cardiovascular disease (CV), often used interchangeably with the term 'heart disease', refers to a range of conditions that affect the heart such as coronary artery disease, arrhythmias, congestive heart failure, cerebrovascular disease etc. Many forms of CV can be prevented or treated with healthy lifestyle choices, by controlling conditions such as atherosclerosis, high blood pressure, diabetes or obesity with a verity of medicines such as antiplatelet drugs, anticoagulants, digitalis, angiotensin converting enzyme (ACE) inhibitors, beta blockers, and LDL cholesterol-lowering agents etc. Due to the comorbidity, patients often need to take multiple medicines, and it would be desirable if one pill can target multiple abnormalities.

With demonstrated ability to prevent cardiovascular disease, statins are among one of the most widely prescribed medications. Although statins are generally well tolerated, statin intolerance occurs in some patients and requires careful consideration. In addition, patients are sometimes concerned about the potential risk of statins causing diabetes mellitus, cancer, and memory loss and often question whether they should continue with their medication. For statin-intolerant patients, non-statin LDL-C-lowering drugs can be used; however, till the PCSK9 inhibitors are approved, none of the approved drugs has been nearly as effective as statins. Developing alternative and effective therapeutics for these patients is much needed.

Neurodegenerative disease is an umbrella term for a range of conditions that primarily affect the neurons in the human brain. Neurons are the building blocks of the nervous system that includes the brain and spinal cord. Neurons normally don't reproduce or replace themselves when they become damaged or die. Examples of neurodegenerative diseases include Parkinson's, Alzheimer's, and Huntington's disease. Neurodegenerative diseases are incurable and debilitating conditions that result in progressive degeneration and/or death of nerve cells. The unmet medical needs for neurodegenerative diseases desperately call for the development of effective therapeutics.

Muscle atrophy is a decrease in the mass of the muscle, which can involve a partial or complete wasting away of muscle. Muscle atrophy occurs due to changes in the balance between protein synthesis and degradation. Muscle atrophy can significantly affect a patient's quality of life as the patient becomes unable to perform certain tasks or risks accidents (e.g., falling). Muscle atrophy is associated with aging and can be a serious consequence of different diseases, including cancer, AIDS, and diabetes. Comparing to non-diabetic older adults, elderly with type 2 diabetes have lower skeletal muscle strength, and are often associated with excessive loss of skeletal muscle mass. Currently, there are no drugs approved for the treatment of skeletal muscle atrophy.

Sarcopenia is characterized first by a muscle atrophy, along with a reduction in muscle tissue quality, characterized by such factors as replacement of muscle fibers with fat, an increase in fibrosis, changes in muscle metabolism, oxidative stress, and degeneration of the neuromuscular junction and leading to progressive loss of muscle function and frailty, currently, there is no approved therapeutics for sarcopenia.

Cancer is a group of diseases involving abnormal cell growth with the potential to invade or spread to other parts of the body. In 2012, about 14 million new cases of cancer occurred globally. The most common types of cancer include lung cancer, prostate cancer, colorectal cancer and stomach cancer for men, and breast cancer, colorectal cancer, lung cancer and cervical cancer for women. While many treatment options for cancer exist, including surgery, chemotherapy, radiation therapy, hormonal therapy, targeted therapy and palliative care, cancer remains a top health threat and is responsible for about 15% of all human deaths.

Fatty liver is a reversible condition wherein large vacuoles of triglyceride fat accumulate in liver cells via the process of steatosis. Despite having multiple causes, fatty liver can be considered a single disease that occurs worldwide in those with excessive alcohol intake and the obese. Non-alcoholic fatty liver disease (NAFLD) is a form of fatty liver diseases that occurs when excessive fat is deposited in the liver of patients without excessive alcohol intake. NAFLD is generally recognized to be associated with metabolic syndrome such as insulin resistance, hypertension and obesity. NAFLD affects about a third of the adult population in developed countries. Non-alcoholic steatohepatitis (NASH) is the most extreme form of NAFLD with chronic inflammation that can lead to progressive fibrosis (scarring), cirrhosis, and eventual liver failure and death. NASH resembles alcoholic liver disease, but occurs in people who drink little or no alcohol. A major feature of NASH is fat in the liver, along with inflammation and damage. Most people with NASH, an often "silent" liver disease, feel well and are not aware that they have a liver problem. Nevertheless, NASH can be severe and can lead to cirrhosis, when the liver is permanently damaged and scarred and no longer work properly.

Currently, there are no drugs approved for the treatment of NASH, which occurs in about a quarter of patients with NAFLD. The current standard of care for NASH involves weight loss and increased physical activities. NASH affects 2-5% of Americans and is becoming more common, possibly because of the greater number of Americans with obesity. In the past 10 years, the rate of obesity has doubled in adults and tripled in children.

The therapeutics and methods currently available for the management of diseases or disorders such as diabetes, diabetic complications, dyslipidemia, obesity, metabolic syndromes, pre-diabetes, Heart diseases, neurodegenerative diseases, NAFLD, NASH, muscle atrophy, inflammation and cancers are suboptimal. There remains an ongoing and urgent need for novel and improved therapeutics and methods to treat such diseases or disorders.

SUMMARY OF THE INVENTION

The invention is based in part on various novel compositions of berberine in combination with pharmacologically active organic acids, and related methods of their use in treating and/or preventing various diseases or disorders.

The invention is also based in part on various novel compounds prepared from berberine and pharmacologically active organic acids, various novel compounds prepared from ursodeoxycholic acid and pharmacologically active organic bases, and pharmaceutical compositions thereof, and methods of their preparation and therapeutic use in treating and/or preventing various diseases or disorders.

The compounds and pharmaceutical compositions of the invention can be utilized to treat various diseases or disorders, such as diabetes, diabetic complications, dyslipidemia, dyslipidemia in statin-intolerance patients, hyperlipidemia, hypercholesterolemia, hypertriglyceridemia, diabetic dyslipidemia, obesity, metabolic syndromes, pre-diabetes, heart diseases, neurodegenerative diseases, sarcopenia, muscle atrophy, inflammation, and cancers as well as various liver diseases or disorders, such as fatty liver, non-alcoholic fatty liver disease, non-alcoholic steatohepatitis, cholestatic liver diseases or graft-versus-host disease of the liver. The compounds of this invention are also useful in improving liver functions in chronic viral associated liver diseases and alcohol-related liver diseases.

In one aspect, the invention generally relates to a composition comprising: (a) berberine or a derivative or analog thereof; (b) one or more pharmacologically active organic acids; and (c) optionally a pharmaceutically acceptable excipient, carrier, or diluent. The berberine and the pharmacologically active organic acid(s) are present in amounts that, when administered to a subject, are sufficient to treat, prevent, or reduce one or more diseases or disorders selected from metabolic disorders, heart diseases, neurodegenerative diseases, muscle atrophy, inflammation, and cancer, or a related disease or disorder thereof in a mammal, including a human.

In another aspect, the invention generally relates to a method for treating, reducing, or preventing a metabolic disorder. The method includes administering to a subject in need thereof a pharmaceutical composition, which includes: (a) berberine or a derivative or analog thereof; (b) one or more pharmacologically active organic acids, in a therapeutically effective amount, and (c) optionally a pharmaceutically acceptable excipient, carrier, or diluent.

In yet another aspect, the invention generally relates to a kit that includes: (i) a first agent of berberine or a derivative or analog thereof; (ii) one or more second agent(s) selected from -(+)-α-lipoic acid, hydroxycitric acid, eicosapentaenoic acid, docosahexaenoic acid, docosapentaenoic acid, ursolic acid, corosolic acid, cinnamic acid, cholic acid, obeticholic acid, ursodeoxycholic acid, oleanolic acid, salicylic acid, betulinic acid, chlorogenic acid, caffeic acid, bassic acid, acetyl L-carnitine, S-allyl cysteine sulphoxide, S-methyl cysteine sulfoxide, pantothenic acid, ascorbic acid, retinoic acid, rhein, nicotinic acid, biotin, and other organic acid that is generally recognized pharmacologically active for one or more diseases or disorders selected from metabolic disorders, heart diseases, neurodegenerative diseases, muscle atrophy, inflammation, and cancer, or a related disease or disorder thereof in a mammal, including a human by those of skill in the art. The first and second agents can be either be a purified active pharmaceutical ingredient or as an active ingredient from natural extract, for examples: bile acids (cholic acid, deoxycholic acid etc.), rhubarb extracts (rhein), cinnamon extract (cinnamic acid), banaba extract (corosolic acid) etc.; and (iii) instructions for administering the combined agents to a patient having or at risk of having one or more diseases or disorders selected from metabolic disorders, heart diseases, neurodegenerative diseases, muscle atrophy, and cancer.

In yet another aspect, the invention generally relates to an acid-base addition salt in substantially pure form, having the formula of:

$$(X^+)_m(U^-)_n \qquad (I)$$

wherein
(a) U⁻ is an anionic moiety of ursodeoxycholic acid or a derivative or analog thereof;
(b) X⁺ is a cationic moiety of a pharmacologically active organic base; and
(c) m and n are integers independently selected from 1, 2, 3, 4, 5 and 6 so as to arrive at a charge neutral salt.

In yet another aspect, the invention generally relates to a pharmaceutical composition comprising an amount of an acid-base addition salt having the formula of:

$$(X^+)_m(U^-)_n \qquad (I)$$

wherein
(a) U⁻ is an anionic moiety of ursodeoxycholic acid or a derivative or analog thereof;
(b) X⁺ is a cationic moiety of a pharmacologically active organic base; and
(c) m and n are integers independently selected from 1, 2, 3, 4, 5 and 6 so as to arrive at a charge neutral salt,
effective to treat, prevent, or reduce one or more diseases or disorders selected from fatty liver, NAFLD and NASH, cholestatic liver diseases, graft-versus-host disease of the liver, chronic viral associated liver diseases, alcohol-related liver diseases, metabolic diseases or disorders such as pre-diabetes, diabetes, diabetic dyslipidemia, dyslipidemia in statin-intolerance patients, hyperlipidemia, obesity or a related disease or disorder thereof in a mammal, including a human, and a pharmaceutically acceptable excipient, carrier, or diluent.

In yet another aspect, the invention generally relates to a method for treating, reducing, or preventing a disease or disorder. The method includes administering to a subject in need thereof a pharmaceutical composition comprising an amount of an acid-base addition salt having the formula of:

$$(X^+)_m(U^-)_n \qquad (I)$$

wherein
(a) U⁻ is an anionic moiety of ursodeoxycholic acid or a derivative or analog thereof;
(b) X⁺ is a cationic moiety of a pharmacologically active organic base; and
(c) m and n are integers independently selected from 1, 2, 3, 4, 5 and 6 so as to arrive at a charge neutral salt,
effective to treat, prevent, or reduce one or more diseases or disorders selected from fatty liver, NAFLD and NASH, cholestatic liver diseases, graft-versus-host disease of the liver, chronic viral associated liver diseases, alcohol-related liver diseases, metabolic diseases or disorders such as pre-diabetes, diabetes, diabetic dyslipidemia, dyslipidemia in statin-intolerance patients, hyperlipidemia, obesity or a related disease or disorder thereof in a mammal, including a human, and a pharmaceutically acceptable excipient, carrier, or diluent.

In yet another aspect, the invention generally relates to an acid-base addition salt in substantially pure form, having the formula of:

$$(B^+)_m(Y^-)_n \qquad (II)$$

wherein
(a) B⁺ is a cationic moiety of berberine or a derivative or analog thereof;
(b) Y⁻ is an anionic moiety of a pharmacologically active organic acid; and
(c) m and n are integers independently selected from 1, 2, 3, 4, 5 and 6 so as to arrive at a charge neutral salt.

In yet another aspect, the invention generally relates to a pharmaceutical composition comprising an amount of an acid-base addition salt having the formula of:

$$(B^+)_m(Y^-)_n \qquad (II)$$

wherein
(a) B⁺ is a cationic moiety of berberine or a derivative or analog thereof;
(b) Y⁻ is an anionic moiety of a pharmacologically active organic acid; and
(c) m and n are integers independently selected from 1, 2, 3, 4, 5 and 6 so as to arrive at a charge neutral salt,
effective to treat, prevent, or reduce one or more diseases or disorders selected from metabolic disorders, heart diseases, neurodegenerative diseases, sarcopenia, muscle atrophy, inflammation, and cancer, or a related disease or disorder thereof in a mammal, including a human, and a pharmaceutically acceptable excipient, carrier, or diluent.

In yet another aspect, the invention generally relates to a method for treating, reducing, or preventing a disease or disorder. The method includes administering to a subject in need thereof a pharmaceutical composition comprising an amount of an acid-base addition salt having the formula of:

$$(B^+)_m(Y^-)_n \qquad (II)$$

wherein
(a) B⁺ is a cationic moiety of berberine or a derivative or analog thereof;

(b) Y⁻ is an anionic moiety of a pharmacologically active organic acid; and (c) m and n are integers independently selected from 1, 2, 3, 4, 5 and 6 so as to arrive at a charge neutral salt, effective to treat, prevent, or reduce one or more diseases or disorders selected from metabolic disorders, heart diseases, neurodegenerative diseases, sarcopenia, muscle atrophy, inflammation, and cancer, or a related disease or disorder thereof in a mammal, including a human, and a pharmaceutically acceptable excipient, carrier, or diluent.

BRIEF DESCRIPTION OF THE DRAWINGS

FIG. 1. Body weight of each treatment group at day 0 and day 14.

FIG. 2. Change of body weight of each treatment group after 14 days of treatment.

FIG. 3. Blood glucose of each treatment group at day 2 and day 15.

FIG. 4. Change of blood glucose of each treatment group at day 2 and day 15.

FIG. 5. $^1$H NMR of metformin ursodeoxycholate in DMSO-$D_6$.

FIG. 6. IR spectrum of metformin ursodeoxycholate.

FIG. 7. $^1$H NMR of berberine ursodeoxycholate (purified product).

FIG. 8. $^1$H NMR of mixture of berberine hydrochloride (1.0 equiv.) and ursodeoxycholic acid (1.0 equiv.) in DMSO-$D_6$.

FIG. 9. IR spectrum of berberine ursodeoxycholate (crude product).
The carbonyl stretching vibration band C=O of ursodeoxycholic acid at about 1721 cm$^{-1}$ disappeared in IR spectrum of berberine ursodeoxycholate.

FIG. 10. IR spectrum of mixture of berberine hydrochloride (1.0 equiv.) and ursodeoxycholic acid (1.0 equiv.). The carbonyl stretching vibration band C=O of ursodeoxycholic acid appears at about 1719 cm$^{-1}$.

FIG. 11. Mass spectroscopy of berberine ursodeoxycholate: in negative MS mode, molecular mass of UDCA [M-H]⁻ 391.28 was identified.

FIG. 12. Mass spectroscopy of berberine ursodeoxycholate: in positive MS mode, molecular mass of BBR⁺ 336.14 was identified.

FIG. 13. (A) Plasma glucose concentrations during oral glucose tolerance test (OGTT) and (B) the area under the OGTT glucose curve. Data are expressed as the mean±S.E.M (n=7~13). ** $p<0.01$ G2 vs. G1; # $p<0.05$ G4, G5, G6, or G7 vs. G2.

FIG. 14. Image of liver Sultan III staining in various groups (n=7~13).

FIG. 15. $^1$H NMR of Berberine ursolic salt (400 MHz, DMSO-$D_6$).

FIG. 16. The Effect of BUDCA on Serum LDL-c level, Serum HDL-c level, TC/HDL-c and AI of Hyperlipidemic Hamsters.

FIG. 17. The Effect of BUDCA on Serum AST Level of Hyperlipidemic Hamsters.

FIG. 18. The Effect of BUDCA on Serum ALT Level of Hyperlipidemic Hamsters.

FIG. 19. The Effect of BUDCA on Liver Weight and Liver Index of Hyperlipidemic Hamsters.

FIG. 20. The General Observation of Lipid Deposition in Liver Tissue.

FIG. 21. The Effect of BUDCA on TC and TG Content in Livers of Hyperlipidemic Hamsters.

FIG. 22. The Effect of BUDCA on Inflammation Score and Positive Area for Oil Red O.

DEFINITIONS

Unless defined otherwise, all technical and scientific terms used herein have the same meaning as commonly understood by one of ordinary skill in the art to which this invention belongs. General principles of organic chemistry, as well as specific functional moieties and reactivity, are described in "Organic Chemistry", Thomas Sorrell, University Science Books, Sausalito: 2006.

Certain compounds of the present invention may exist in particular geometric or stereoisomeric forms. The present invention contemplates all such compounds, including cis- and trans-isomers, R- and S-enantiomers, diastereomers, (D)-isomers, (L)-isomers, the racemic mixtures thereof, and other mixtures thereof, as falling within the scope of the invention. Additional asymmetric carbon atoms may be present in a substituent such as an alkyl group. All such isomers, as well as mixtures thereof, are intended to be included in this invention.

Isomeric mixtures containing any of a variety of isomer ratios may be utilized in accordance with the present invention. For example, where only two isomers are combined, mixtures containing 50:50, 60:40, 70:30, 80:20, 90:10, 95:5, 96:4, 97:3, 98:2, 99:1, or 100:0 isomer ratios are contemplated by the present invention. Those of ordinary skill in the art will readily appreciate that analogous ratios are contemplated for more complex isomer mixtures.

If, for instance, a particular enantiomer of a compound of the present invention is desired, it may be prepared by asymmetric synthesis, or by derivation with a chiral auxiliary, where the resulting diastereomeric mixture is separated and the auxiliary group cleaved to provide the pure desired enantiomers. Alternatively, where the molecule contains a basic functional group, such as amino, or an acidic functional group, such as carboxyl, diastereomeric salts are formed with an appropriate optically-active acid or base, followed by resolution of the diastereomers thus formed by fractional crystallization or chromatographic methods well known in the art, and subsequent recovery of the pure enantiomers.

Given the benefit of this disclosure, one of ordinary skill in the art will appreciate that synthetic methods, as described herein, may utilize a variety of protecting groups. By the term "protecting group", as used herein, it is meant that a particular functional moiety, e.g., O, S, or N, is temporarily blocked so that a reaction can be carried out selectively at another reactive site in a multifunctional compound. In preferred embodiments, a protecting group reacts selectively in good yield to give a protected substrate that is stable to the projected reactions; the protecting group should be selectively removable in good yield by preferably readily available, non-toxic reagents that do not attack the other functional groups; the protecting group forms an easily separable derivative (more preferably without the generation of new stereogenic centers); and the protecting group has a minimum of additional functionality to avoid further sites of reaction. Oxygen, sulfur, nitrogen, and carbon protecting groups may be utilized. Examples of a variety of protecting groups can be found in Protective Groups in Organic Synthesis, Third Ed. Greene, T. W. and Wuts, P. G., Eds., John Wiley & Sons, New York: 1999.

It will be appreciated that the compounds, as described herein, may be substituted with any number of substituents or functional moieties. Throughout the specifications, groups and substituents thereof may be chosen to provide stable moieties and compounds.

As used herein, the term "effective amount" of an active agent refers to an amount sufficient to elicit the desired biological response. As will be appreciated by those of ordinary skill in this art, the effective amount of a compound of the invention may vary depending on such factors as the desired biological endpoint, the pharmacokinetics of the compound, the disease being treated, the mode of administration, and the patient.

As used herein, the term "treating, reducing, or preventing a disease or disorder" refers to ameliorating such a condition before or after it has occurred. As compared with an equivalent untreated control, such reduction or degree of prevention is at least 5%, 10%, 20%, 40%, 50%, 60%, 80%, 90%, 95%, or 100% as measured by any standard technique.

As used herein, the term "pharmaceutically acceptable excipient, carrier, or diluent" refers to a pharmaceutically acceptable material, composition or vehicle, such as a liquid or solid filler, diluent, excipient, solvent or encapsulating material, involved in carrying or transporting the subject pharmaceutical agent from one organ, or portion of the body, to another organ, or portion of the body. Each carrier must be "acceptable" in the sense of being compatible with the other ingredients of the formulation and not injurious to the patient. Some examples of materials which can serve as pharmaceutically-acceptable carriers include: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; alginic acid; pyrogen-free water; isotonic saline; Ringer's solution; ethyl alcohol; phosphate buffer solutions; and other non-toxic compatible substances employed in pharmaceutical formulations. Wetting agents, emulsifiers and lubricants, such as sodium lauryl sulfate, magnesium stearate, and polyethylene oxide-polypropylene oxide copolymer as well as coloring agents, release agents, coating agents, sweetening, flavoring and perfuming agents, preservatives and antioxidants can also be present in the compositions.

As used herein, the terms "isolated" or "purified" refer to a material that is substantially or essentially free from components that normally accompany it in its native state. Purity and homogeneity are typically determined using analytical chemistry techniques such as polyacrylamide gel electrophoresis or high performance liquid chromatography.

As used herein, the term "subject" refers to any animal (e.g., a mammal), including, but not limited to humans, non-human primates, rodents, and the like, which is to be the recipient of a particular treatment. Typically, the terms "subject" and "patient" are used interchangeably herein in reference to a human subject.

As used herein, the "an amount sufficient" refers to the amount of a compound, alone or in combination with another therapeutic regimen, required to treat, prevent, or reduce a metabolic disorder such as diabetes in a clinically relevant manner. A sufficient amount of an active compound used to practice the present invention for therapeutic treatment of conditions caused by or contributing to diabetes varies depending upon the manner of administration, the age, body weight, and general health of the mammal or patient. Ultimately, the prescribers will decide the appropriate amount and dosage regimen. Additionally, an effective amount may be an amount of compound in the combination of the invention that is safe and efficacious in the treatment of a patient having a metabolic disorder such as diabetes over each agent alone as determined and approved by a regulatory authority (such as the U.S. Food and Drug Administration).

As used herein, the "low dosage" refers to at least 5% less (e.g., at least 10%, 20%, 50%, 80%, 90%, or even 95%) than the lowest standard recommended dosage of a particular compound formulated for a given route of administration for treatment of any human disease or condition. For example, a low dosage of an agent that reduces glucose levels and that is formulated for administration by inhalation will differ from a low dosage of the same agent formulated for oral administration.

As used herein, the "high dosage" is meant at least 5% (e.g., at least 10%, 20%, 50%, 100%, 200%, or even 300%) more than the highest standard recommended dosage of a particular compound for treatment of any human disease or condition.

Isotopically-labeled compounds are also within the scope of the present disclosure. As used herein, an "isotopically-labeled compound" refers to a presently disclosed compound including pharmaceutical salts and prodrugs thereof, each as described herein, in which one or more atoms are replaced by an atom having an atomic mass or mass number different from the atomic mass or mass number usually found in nature. Examples of isotopes that can be incorporated into compounds presently disclosed include isotopes of hydrogen, carbon, nitrogen, oxygen, phosphorous, fluorine and chlorine, such as $^{2}H$, $^{3}H$, $^{13}C$, $^{14}C$, $^{15}N$, $^{18}O$, $^{17}O$, $^{31}P$, $^{32}P$, $^{35}S$, $^{18}F$, and $^{36}Cl$, respectively.

By isotopically-labeling the presently disclosed compounds, the compounds may be useful in drug and/or substrate tissue distribution assays. Tritiated ($^{3}H$) and carbon-14 ($^{14}C$) labeled compounds are particularly preferred for their ease of preparation and detectability. Further, substitution with heavier isotopes such as deuterium ($^{2}H$) can afford certain therapeutic advantages resulting from greater metabolic stability, for example increased in vivo half-life or reduced dosage requirements and, hence, may be preferred in some circumstances. Isotopically labeled compounds presently disclosed, including pharmaceutical salts, esters, and prodrugs thereof, can be prepared by any means known in the art.

Further, substitution of normally abundant hydrogen ($^{1}H$) with heavier isotopes such as deuterium can afford certain therapeutic advantages, e.g., resulting from improved absorption, distribution, metabolism and/or excretion (ADME) properties, creating drugs with improved efficacy, safety, and/or tolerability. Benefits may also be obtained from replacement of normally abundant $^{12}C$ with $^{13}C$. See, WO 2007/005643, WO 2007/005644, WO 2007/016361, and WO 2007/016431.

Stereoisomers (e.g., cis and trans isomers) and all optical isomers of a presently disclosed compound (e.g., R and S enantiomers), as well as racemic, diastereomeric and other mixtures of such isomers are within the scope of the present disclosure.

Compounds of the present invention are, subsequent to their preparation, preferably isolated and purified to obtain a composition containing an amount by weight equal to or greater than 95% ("substantially pure"), which is then used or formulated as described herein. In certain embodiments, the compounds of the present invention are more than 99% pure.

Solvates and polymorphs of the compounds of the invention are also contemplated herein. Solvates of the compounds of the present invention include, for example, hydrates.

Possible formulations include those suitable for oral, sublingual, buccal, parenteral (for example subcutaneous, intramuscular, or intravenous), rectal, topical including transdermal, intranasal and inhalation administration. Most suitable means of administration for a particular patient will depend on the nature and severity of the disease or condition being treated or the nature of the therapy being used and on the nature of the active compound.

DETAILED DESCRIPTION OF THE INVENTION

The invention provides various novel compositions of berberine in combination with pharmacologically active organic acids, and related methods of their use in treating and/or preventing various diseases or disorders. A noteworthy feature of the invention is the unique and synergistic effect given rise by the combinations of berberine and select pharmacologically active organic acids.

The invention also provides novel salts of ursodeoxycholic acid and organic bases, pharmaceutical compositions thereof, as well as related methods of preparation and use in treating and/or preventing various liver diseases or disorders. Salts of ursodeoxycholic acid include those with organic bases such as berberine, metformin, carnitine, coptisine, palmatine, jatrorrhizine.

The invention further provides salts of berberine and organic acids, pharmaceutical compositions thereof, as well as related methods of their use in treating various diseases or disorders. Salts of berberine include those with organic acids such as -(+)-α-lipoic acid, hydroxycitric acid, eicosapentaenoic acid, docosahexaenoic acid, docosapentaenoic acid, ursolic acid, corosolic acid, cinnamic acid, cholic acid, obeticholic acid, ursodeoxycholic acid, oleanolic acid, salicylic acid, betulinic acid, chlorogenic acid, caffeic acid, bassic acid, acetyl L-carnitine, S-allyl cysteine sulphoxide, S-methyl cysteine sulfoxide, pantothenic acid, ascorbic acid, retinoic acid, rhein, nicotinic acid, and biotin.

A central feature of the invention is the unique and synergistic effect given rise to by each of the two parts of the novel salts, i.e., a pharmaceutically active cationic portion and a pharmaceutically active anionic portion that collectively and synergistically target a disease or disorder with complementary mechanisms of actions and thereby providing improved efficacies.

Diseases and disorders that may be treated and/or prevented by the compounds, pharmaceutical compositions and methods disclosed herein include such as diabetes, diabetic complications, dyslipidemia, dyslipidemia in statin-intolerance patients, hyperlipidemia, hypercholesterolemia, hypertriglyceridemia, diabetic dyslipidemia, obesity, metabolic syndromes, pre-diabetes, atherosclerosis, heart diseases, neurodegenerative diseases, sarcopenia, muscle atrophy, inflammation, cancer and liver diseases and conditions such as fatty liver, non-alcoholic fatty liver disease, non-alcoholic steatohepatitis, cholestatic liver diseases or graft-versus-host disease of the liver. The compounds of this invention are also useful in improving liver functions in chronic viral associated liver diseases and alcohol-related liver diseases.

Combinations of Berberine or Derivative(s) and Pharmacologically Active Organic Acids The invention provides various novel compositions of berberine in combination with pharmacologically active organic acids, and related methods of their use in treating various diseases or disorders. The invention thus embodies a unique approach that uses berberine in synergistic combinations with select pharmacologically active organic acids.

In one aspect, the invention generally relates to a composition comprising: (a) berberine or a derivative or analog thereof; (b) one or more pharmacologically active organic acids; and (c) optionally a pharmaceutically acceptable excipient, carrier, or diluent. The berberine and the pharmacologically active organic acid(s) are present in amounts that, when administered to a subject, are sufficient to treat, prevent, or reduce one or more diseases or disorders selected from metabolic disorders, heart diseases, neurodegenerative diseases, muscle atrophy, liver diseases, inflammation, and cancer, or a related disease or disorder thereof in a mammal, including a human.

Berberine (5,6-dihydro-9,10-dimethoxybenzo[g]-1,3-benzodioxolo[5,6-a]quinolizinium), an isoquinoline alkaloid isolated from Rhizoma Coptidis, has had a long history of medicinal use in China to treat various gastrointestinal diseases. Berberine is found in a variety of plants as *Berberis*, *Hydrastis canadensis*, *Xanthorhiza simplicissima*, *Phellodendron amurense*, *Coptis chinensis*, *Tinospora cordifolia*, *Argemone mexicana*, and *Eschscholzia californica*. In the past two decades, in vitro and in vivo studies have demonstrated the efficacy of berberine when used alone or as a combination for diabetes, dyslipidemia, cancer, neuroprotection and cardiovascular diseases. Currently, berberine can be obtained commercially in the form of chloride, sulfate or tannate salt, with berberine hydrochloride having been used in almost all previous studies. The low bioavailability of berberine in the current available forms makes its applications for the treatment of chronic and systemic disease very challenging.

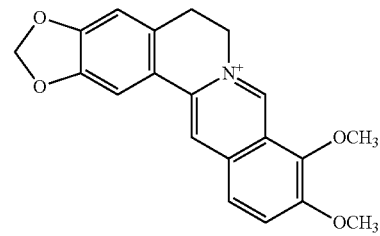

Berberine

-(+)-α-Lipoic acid ((R)-6,8-Dithiooctanoic acid, (R)-6,8-Thioctic acid, (R)-(+)-1,2-Dithiolane-3-pentanoic acid) was identified as a catalytic agent for oxidative decarboxylation of pyruvate and α-ketoglutarate. In human, R-(+)-α-lipoic acid exists in the body as a portion of several multi-enzyme complexes involved in energy formation and is an essential component of mitochondrial respiratory enzymes. R-(+)-α-Lipoic acid is best known for its potent anti-oxidant effects and has been used for the treatment of diabetic neuropathy, degenerative neuronal disease, atherosclerosis and other abnormalities related to oxidative stress.

-(+)-α-Lipoic acid

Hydroxycitric acid (1,2-dihydroxypropane-1,2,3-tricarboxylic acid) is a derivative of citric acid found in a variety of tropical plants including *Garcinia cambogia* and *Hibiscus subdariffa*. Hydroxycitric acid is the active component of *Garcinia cambogia* extract, which has been widely utilized as dietary supplement for weight loss. There have been reports on hydroxycitric acid's effects in improving glucose tolerance, providing liver protection against toxicity associated with ethanol and dexamethasone, and controlling blood pressure. In addition, the compound has been found to reduce markers of inflammation in brain, intestines, kidney and serum.

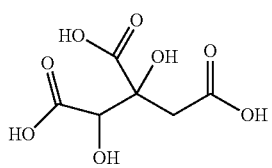

Hydroxycitric acid

Eicosapentaenoic acid (EPA or (5Z,8Z,11Z,14Z,17Z)-5,8,11,14,17-icosapentaenoic acid), and docosahexaenoic acid (DHA, 4Z,7Z,10Z,13Z,16Z,19Z)-docosa-4,7,10,13,16,19-hexaenoic acid), are two best-investigated omega-3 polyunsaturated fatty acids. EPA is the active molecule in two FDA-approved anti-hypertriglyceridemic agents. It has been demonstrated that EPA and DHA can reduce free fatty acid and triglyceride synthesis and increase their disposal. Effects of EPA and DHA have also been demonstrated in reducing chronic inflammation, improving insulin resistance, maintaining heart and vascular health and reducing the risk of coronary heart disease. In addition to EPA and DHA, many more omega-3 fatty acids existed in nature with a range of therapeutic benefits, include but not limited to Docosapentaenoic acid (DPA), α-Linolenic acid (ALA), Eicosatrienoic acid (ETE) etc.

Ursolic acid ((1S,2R,4aS,6aR,6aS,6bR,8aR,10S,12aR,14bS)-10-hydroxy-1,2,6a,6b,9,9,12a-heptamethyl-2,3,4,5,6,6a,7,8,8a,10,11,12,13,14b-tetradecahydro-1H-picene-4a-carboxylic acid) and corosolic acid ((1S,2R,4aS,6aR,6aS,6bR,8aR,10R, 11R,12aR,14bS)-10,11-Dihydroxy-1,2,6a,6b,9,9,12a-heptamethyl-2,3,4,5,6,6a,7,8,8a,10, 11,12,13,14b-tetradecahydro-1H-picene-4a-carboxylic acid) are members of the pentacyclic triterpene acid class of compounds widely distributed in the plant kingdom. They have been shown to exhibit favorable pharmacological effects both in vivo and in vitro, including glucose reduction, anti-obesity, anti-inflammatory, reduce muscle atrophy, anti-cancer, liver protection, anti-oxidative stress.

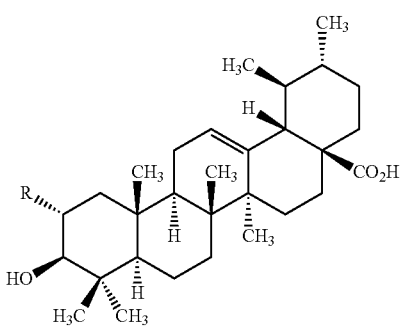

Ursolic acid, R = H
Corosolic acid, R = OH

Cinnamic acid, cholic acid, obeticholic acid, ursodeoxycholic acid, oleanolic acid, salicylic acid, betulinic acid, chlorogenic acid, caffeic acid, bassic acid, acetyl L-carnitine, S-allyl cysteine sulphoxide, S-methyl cysteine sulfoxide, pantothenic acid, ascorbic acid, retinoic acid, rhein, nicotinic acid and biotin in either a purified form or an active extract (Table 1) are additional organic acids with demonstrated pharmacologically activities in the treatment or prevention of diabetes, diabetic complications, dyslipidemia, obesity, metabolic syndromes, pre-diabetes, heart diseases, fatty liver, NAFLD, NASH, muscle atrophy, inflammation, and cancers.

Exemplary pharmacologically active organic acids are listed in Table 1.

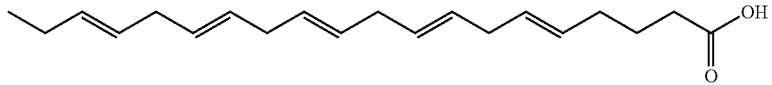

EPA

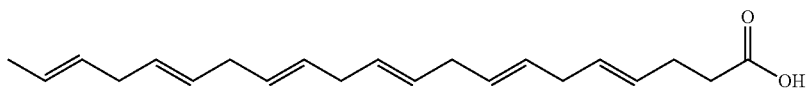

DHA

TABLE 1

Exemplary Pharmacologically Active Organic Acids

| Name | IUPAC Name | Structure |
| --- | --- | --- |
| Cinnamic acid | (E)-3-phenylprop-2-enoic acid | 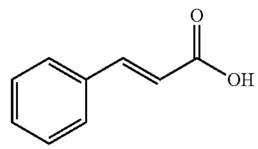 [SMILES: O=C(O)/C=C/c1ccccc1] |
| Cholic acid | (R)-4-((3R,5S,7R,8R,9S,10S,12S,13rR,14S,17R)-3,7,12-trihydroxy-10,13-dimethylhexadecahydro-1H-cyclopenta[α]phenanthren-17-yl)pentanoic acid | 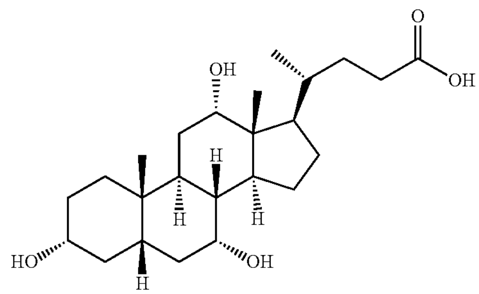 |
| Obeticholic acid | (3α,5β,6α,7α)-6-Ethyl-3,7-dihydroxycholan-24-oic acid | 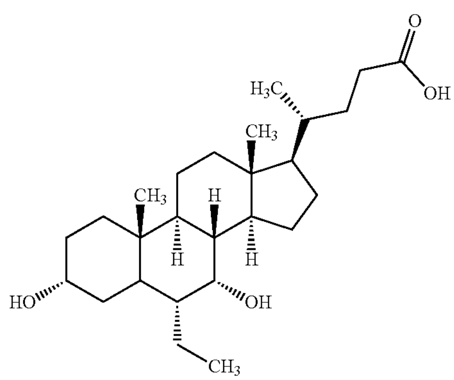 |
| Ursodeoxycholic acid | 3α,7β-dihydroxy-5β-cholan-24-oic acid<br>OR<br>(R)-4-((3R,5S,7S,8R,9S,10S,13R,14S,17R)-3,7-dihydroxy-10,13-dimethylhexadecahydro-1H-cyclopenta[a]phenanthren-17-yl)pentanoic acid | 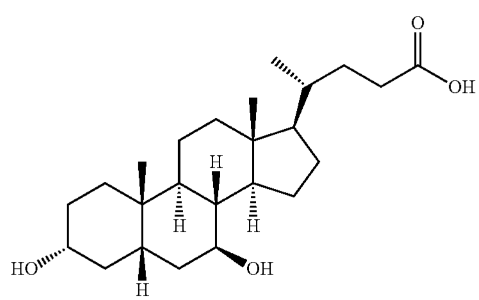 |
| Oleanolic acid | (4aS,6aR,6aS,6bR,8aR,10S,12aR,14bS)-10-hydroxy-2,2,6a,6b,9,9,12a-heptamethyl-1,3,4,5,6,6a,7,8,8a,10,11,12,13,14b-tetradecahydropicene-4a-carboxylic acid | 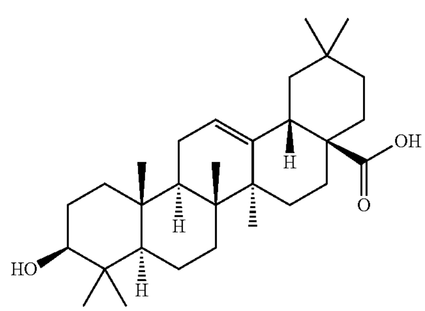 |

TABLE 1-continued

Exemplary Pharmacologically Active Organic Acids

| Name | IUPAC Name | Structure |
|---|---|---|
| Salicylic acid | 2-Hydroxybenzoic acid | 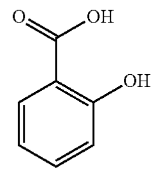 |
| Betulinic acid | (3β)-3-Hydroxy-lup-20(29)-en-28-oic acid | 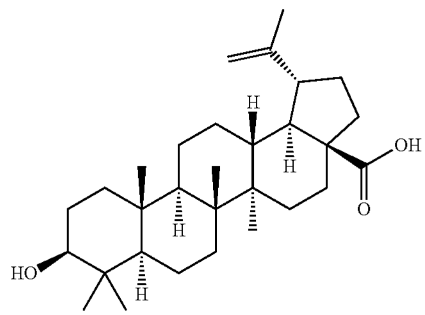 |
| Chlorogenic acid | (1S,3R,4R,5R)-3-{[(2Z)-3-(3,4-dihydroxyphenyl)prop-2-enoyl]oxy}-1,4,5-trihydroxycyclohexane-carboxylic acid | 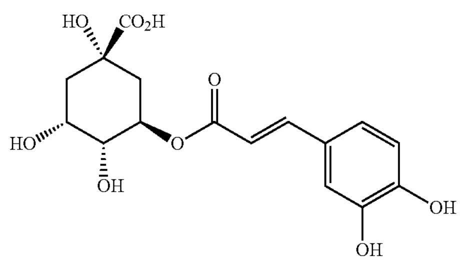 [SMILES: O=C(/C=C/c1ccc(O)c(O)c1)O[C@@H]1C[C@](O)(C(=O)O)C[C@@H](O)[C@H]1O] |
| Caffeic acid | 3-(3,4-Dihydroxyphenyl)-2-propenoic acid 3,4-Dihydroxy-cinnamic acid trans-Caffeate 3,4-Dihydroxy-trans-cinnamate) (E)-3-(3,4-dihydroxyphenyl)-2-propenoic acid 3,4-Dihydroxybenzeneacrylic-acid 3-(3,4-Dihydroxyphenyl)-2-propenoic acid | 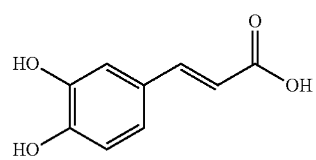 [SMILES: O=C(O)/C=C/c1ccc(O)c(O)c1] |
| Bassic acid | (4aR,6bS,9R,10R,11S,12aR,14bS)-10,11-dihydroxy-9-(hydroxymethyl)-2,2,6b,9,12a-pentamethyl-1,2,3,4,4a,5,6,6a,6b,7,9,10,11,12,12a,12b,13,14b-octadecahydropicene-4a-carboxylic acid | 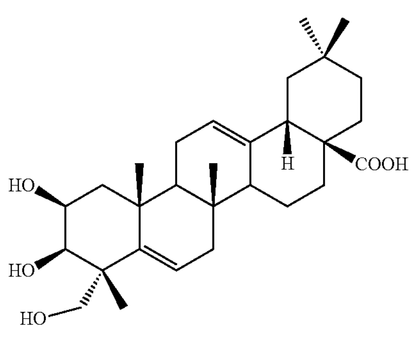 |
| Acetyl L-carnitine | (R)-3-Acetyloxy-4-trimethylammonio-butanoate | 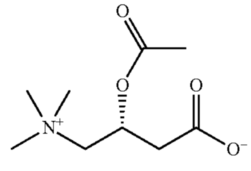 |

TABLE 1-continued

Exemplary Pharmacologically Active Organic Acids

| Name | IUPAC Name | Structure |
| --- | --- | --- |
| S-allyl-L-cysteine sulphoxide | (2R)-2-amino-3-[(S)-prop-2-enylsulfinyl]propanoic acid | 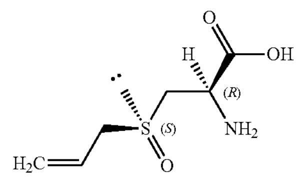 |
| S-methyl-L-cysteine sulfoxide | 3-(methylsulfinyl)-L-alanine | 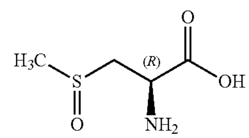 |
| Pantothenic acid | 3-[(2,4-Dihydroxy-3,3-dimethylbutanoyl)amino] propanoic acid | 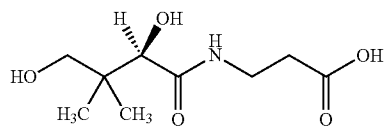 |
| Ascorbic acid | (5R)-[(1S)-1,2-dihydroxyethyl]-3,4-dihydroxyfuran-2(5H)-one | 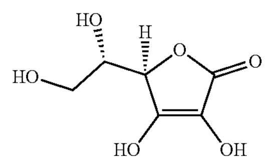 [SMILES: O=C1O[C@H]([C@@H](O)CO)C(O)=C1O] |
| Retinoic acid | (2E,4E,6E,8E)-3,7-dimethyl-9-(2,6,6-trimethylcyclohexen-1-yl)nona-2,4,6,8-tetraenoic acid | 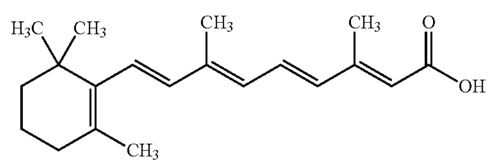 [SMILES: CC1=C(/C=C/C(C)=C/C=C/C(C)=C/C(=O)O)C(C)(C)CCC1] |
| Rhein | 4,5-dihydroxy-9,10-dioxoanthracene-2-carboxylic acid | 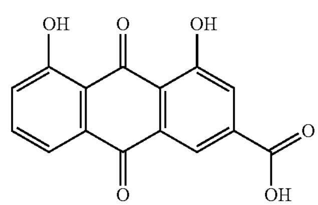 [SMILES: O=C(O)c1cc(O)c2c(c1)C(=O)c1cccc(O)c1C2=O] |
| Nicotinic acid | pyridine-3-carboxylic acid | 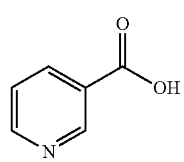 |
| Biotin | 5-[(3aS,4S,6aR)-2-oxohexahydro-1H-thieno[3,4-d]imidazol-4-yl]pentanoic acid | 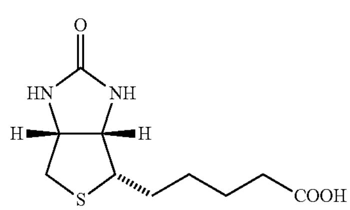 [SMILES: O=C(O)CCCC[C@@H]1SC[C@@H]2NC(=O)N[C@@H]21] |

Exemplary berberine derivatives or analogs are listed in Table 2.
TABLE 2
Berberine Derivatives or Analogs
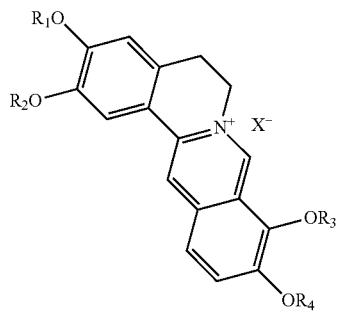
$R_1 = R_2 = R_3 = R_4 = CH_3$
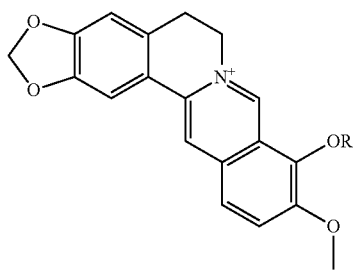
$R = H$
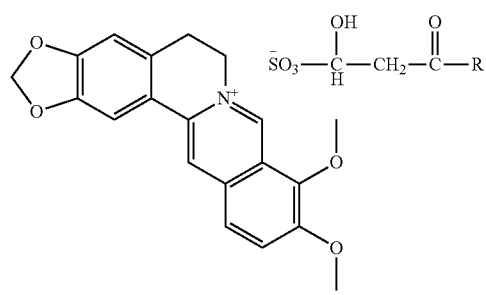
$R = C_8\text{-}C_{12}$ alkyl
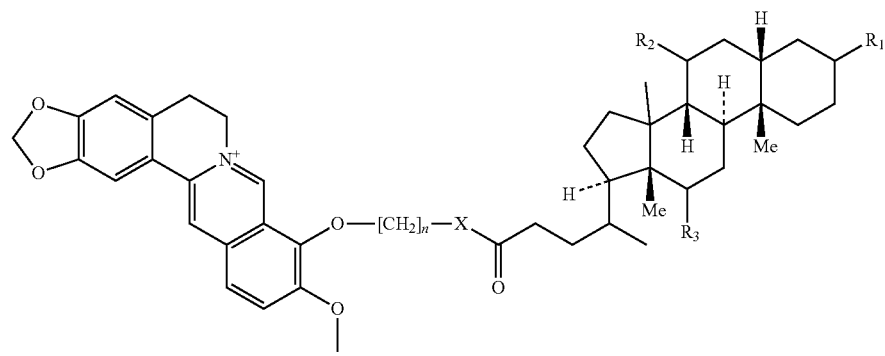
$R_1 = OH$, carbonyl; $R_2$, $R_3 = H$, carbonyl; $n = 2\text{-}6$; $X = O$
$R_1 = OH$, carbonyl; $R_2$, $R_3 = H$, OH, carbonyl; $n = 2\text{-}6$; $X = NH$

TABLE 2-continued

Berberine Derivatives or Analogs

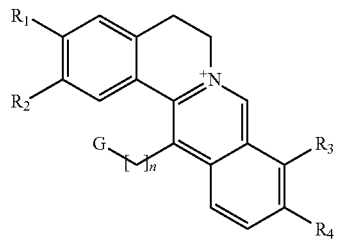

$R_1$, $R_3$, $R_2$, $R_4$ = OH, $C_1$-$C_6$ alkoxy, $OCH_2O$
G = Z—Ar, Y—$Ar_2$
Z = $O(CH_2)_m$, $CONH(CH_2)_m$, $NHCO(CH_2)_m$
Y = $O(CH_2)_mCH$, $CONH(CH_2)_mCH$, $NHCO(CH_2)_mCH$
n = 1-5; m = 1-3; Ar = 5-15 membered unsaturated or aromatic ring

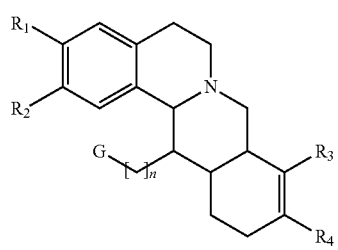

$R_1$, $R_3$, $R_2$, $R_4$ = OH, $C_1$-$C_6$ alkoxy, $OCH_2O$
G = Z—Ar, Y—$Ar_2$
Z = $O(CH_2)_m$, $CONH(CH_2)_m$, $NHCO(CH_2)_m$
Y = $O(CH_2)_mCH$, $CONH(CH_2)_mCH$, $NHCO(CH_2)_mCH$
n = 1-5; m = 1-3; Ar = 5-15 membered unsaturated or aromatic ring

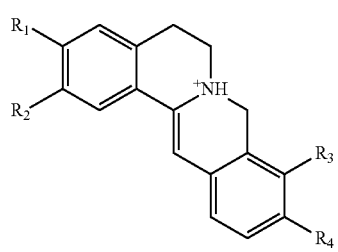

$R_1$, $R_3$, $R_2$, $R_4$ = OH, $C_1$-$C_6$ alkoxy, $OCH_2O$
G = Z—Ar, Y—$Ar_2$
Z = $O(CH_2)_m$, $CONH(CH_2)_m$, $NHCO(CH_2)_m$
Y = $O(CH_2)_mCH$, $CONH(CH_2)_mCH$, $NHCO(CH_2)_mCH$
n = 1-5; m = 1-3; Ar = 5-15 membered unsaturated or aromatic ring

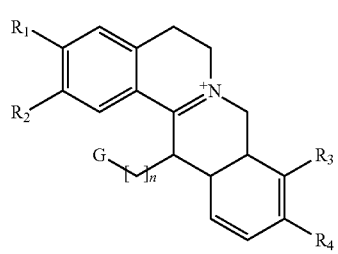

$R_1$, $R_3$, $R_2$, $R_4$ = OH, $C_1$-$C_6$ alkoxy, $OCH_2O$
G = Z—Ar, Y—$Ar_2$
Z = $O(CH_2)_m$, $CONH(CH_2)_m$, $NHCO(CH_2)_m$
Y = $O(CH_2)_mCH$, $CONH(CH_2)_mCH$, $NHCO(CH_2)_mCH$
n = 1-5; m = 1-3; Ar = 5-15 membered unsaturated or aromatic ring TABLE 2-continued
Berberine Derivatives or Analogs
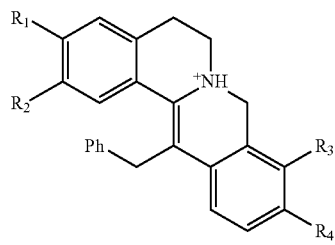
R$_1$, R$_3$, R$_2$, R$_4$ = OH, C$_1$-C$_6$ alkoxy, OCH$_2$O
G = Z—Ar, Y—Ar$_2$
Z = O(CH$_2$)$_m$, CONH(CH$_2$)$_m$, NHCO(CH$_2$)$_m$
Y = O(CH$_2$)$_m$CH, CONH(CH$_2$)$_m$CH, NHCO(CH$_2$)$_m$CH
n = 1-5; m = 1-3; Ar = 5-15 membered unsaturated or aromatic ring
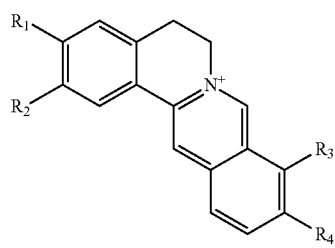
R$_1$, R$_2$, R$_3$, R$_4$ = OCH$_3$, OH, OCH$_2$O
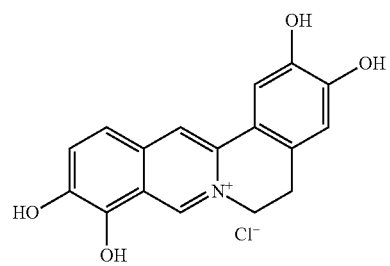 [SMILES: Oc1cc2c(cc1O)-c1cc3ccc(O)c(O)c3c[n+]1CC2 ; [Cl-]]
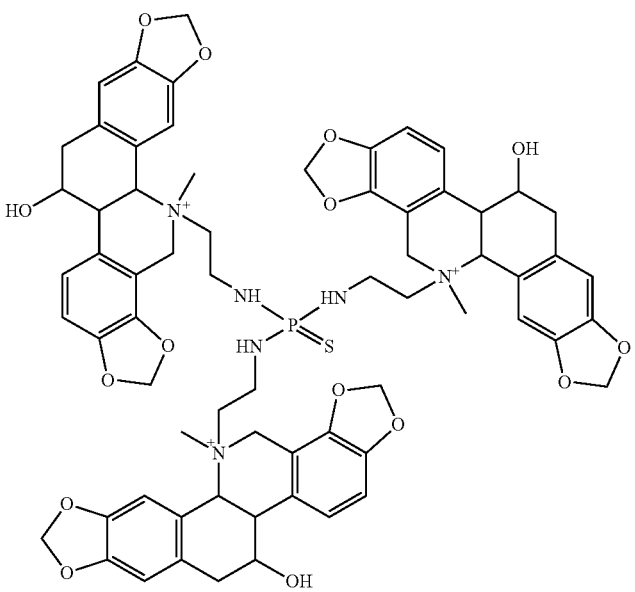

TABLE 2-continued
Berberine Derivatives or Analogs
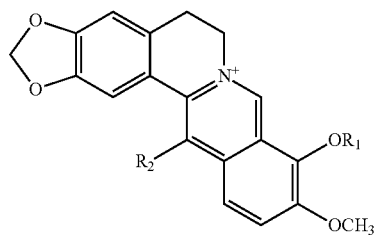
R₁ = H, Me
R₂ = Bn, 3,5-dinitrobenzyl
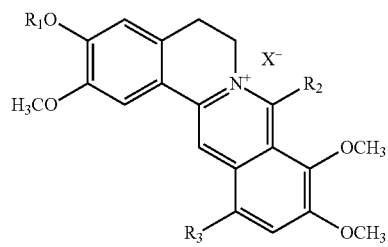
X = F, Cl, Br, I, SO₄, NO₃, PO₄, citrate, acetate, lactate
R₁ and R₂ = independently alkyl; R₃ = H, F, Cl, Br, or I
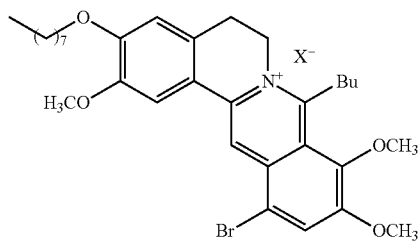
X = F, Cl, Br, I, SO₄, NO₃, PO₄, citrate, acetate, lactate
R₁ and R₂ = independently alkyl; R₃ = H, F, Cl, Br, or I
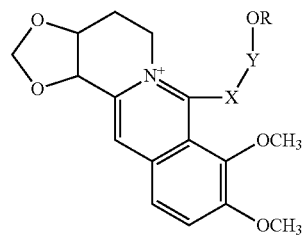
Y = CH₂, —C═O, —C═S; X = C having a linear, branched,
saturated/unsaturated linear structure; n = 1-10
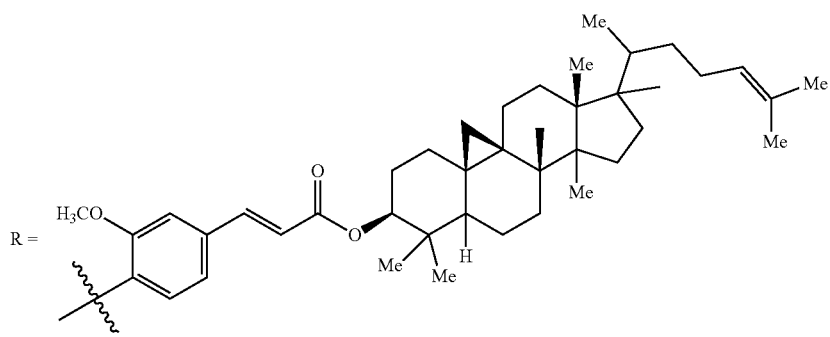

TABLE 2-continued
Berberine Derivatives or Analogs
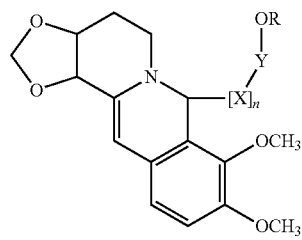
Y = CH$_2$, —C═O, —C═S; X = C having a linear, branched,
saturated/unsaturated linear structure; n = 1-10
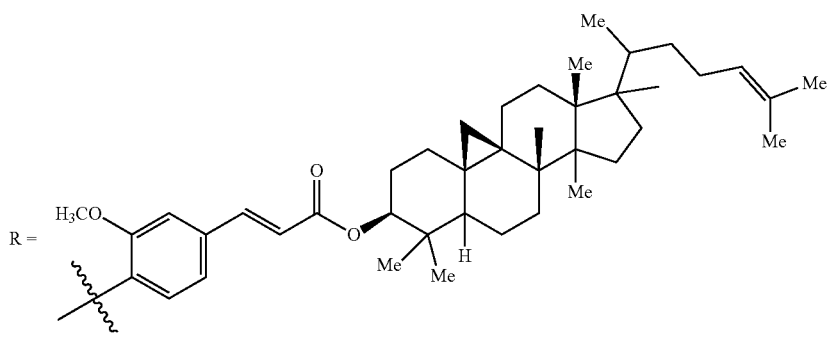
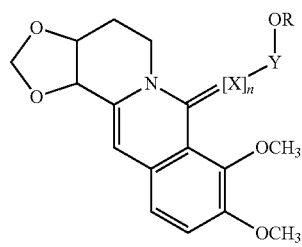
Y = CH$_2$, —C═O, —C═S; X = C having a linear, branched,
saturated/unsaturated linear structure; n = 1-10
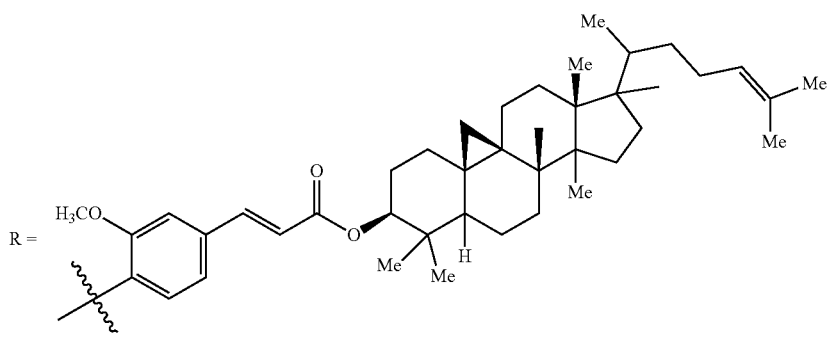
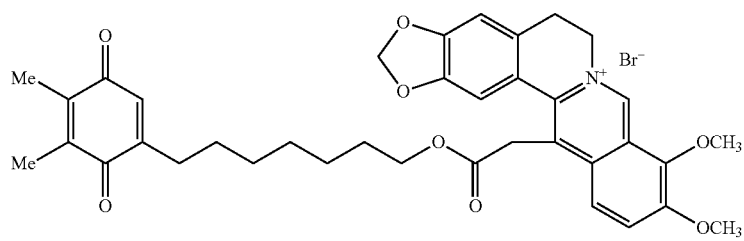 [SMILES: COc1ccc2c(CC(=O)OCCCCCCCC3=CC(=O)C(C)=C(C)C3=O)c3[n+](cc2c1OC)CCc1cc2c(cc1-3)OCO2 ; [Br-]]

TABLE 2-continued

Berberine Derivatives or Analogs

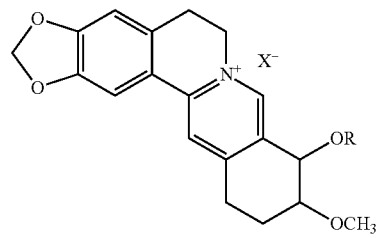

R = glucosyl, mannosyl, maltosyl, lactosyl,
galactosyl, fructosyl, xylosyl, arabinosyl
X = Cl, Br, I

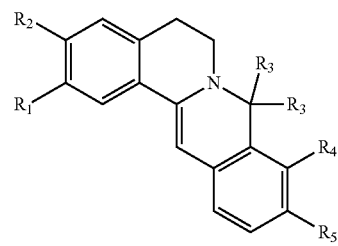

$R_1$, $R_2$ = H, $C_1$-$C_4$ alkoxy, $OCH_2O$
$R_3$ = $C_1$-$C_8$ alkyl
$R_4$, $R_5$ = $C_1$-$C_2$ alkoxy

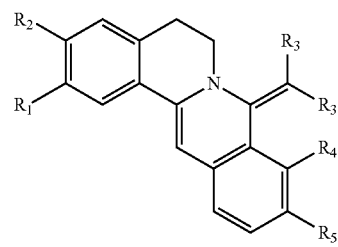

$R_1$, $R_2$ = H, $C_1$-$C_4$ alkoxy, $OCH_2O$
$R_3$ = CN, $COOR_6$ ($R_6$ = $C_1$-$C_2$ alkyl)
$R_4$, $R_5$ = $C_1$-$C_2$ alkoxy

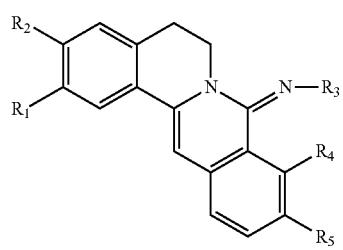

$R_1$, $R_2$ = H, $C_1$-$C_4$ alkoxy, OCH2O
$R_3$ = $C_1$-$C_2$ alkyl, phenyl
$R_4$, $R_5$ = $C_1$-$C_2$ alkoxy

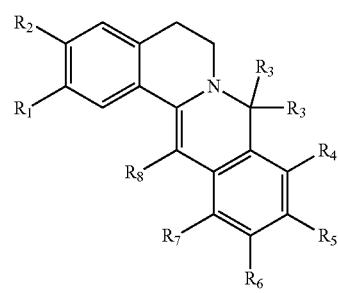

$R_1$, $R_2$ = H, $(CH_2)_{n-6}CO_2R'$, C(O)R'', OR', $NR_{10}R_{11}$, $C(O)NR_{10}R_{11}$, alkyl
$R_1R_2$ = $OCH_2CH_2O$; $R_3$, $R_8$ = H, OH, Cl, Br, F, I, CN, $NH_2$, $(O)NH_2$, $CO_2H$,
alkyl; $R_3'$ = H; $R_3R_3'$= O, $R_4$ = H, halogen, OR', $OSO_2R''$, OC(O)R'', $OCO_2R''$
OC(O)NR'R'', O-alkylene-NR'R'', O-alkylene-$OSO_2R''$, O-alkylene-NR'$SO_2R''$,

TABLE 2-continued
Berberine Derivatives or Analogs
O-alkylene-NR'COR', alkyl; $R_5$, $R_6$ = H, halogen, OH, alkoxy
$R_4R_5$ = $OCH_2O$; $R_5R_6$ = $OCH_2O$; $R_7$ = H, OH, halogen, alkyl or alkoxy
$R_{10}$, $R_{11}$ = H, $CO_2R''$, alkyl
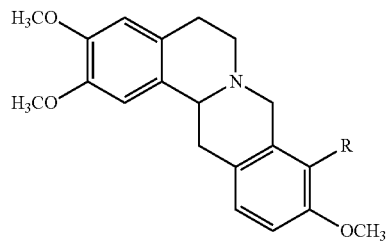
R = $SO_2C_6H_4$-3-F
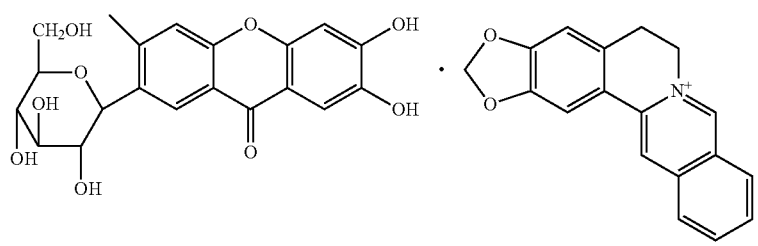
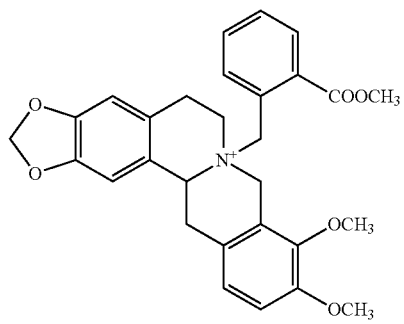 [SMILES: COC(=O)c1ccccc1C[N+]12CCc3cc4c(cc3C1Cc1ccc(OC)c(OC)c1C2)OCO4]
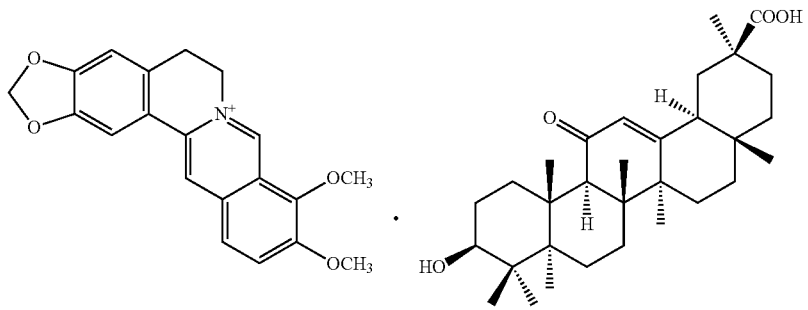
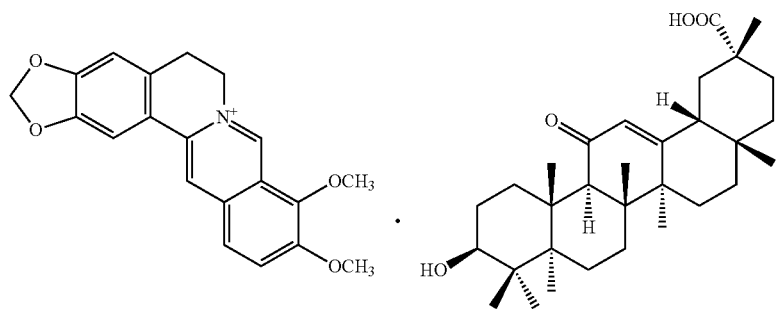

TABLE 2-continued

Berberine Derivatives or Analogs

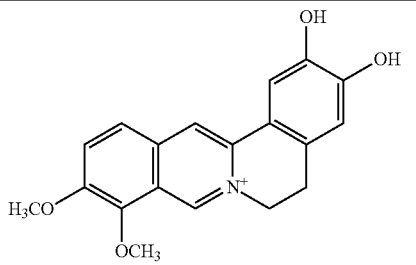

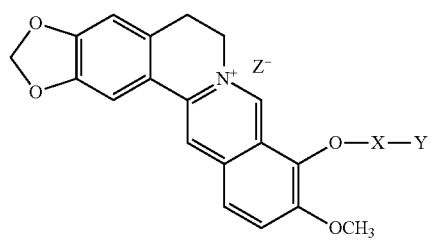

X = (CH$_2$)$_m$, (CH$_2$)$_m$CO; n = 2-10; m = 1-9
Y = NR$_1$Ar, OAr; Ar = substituted aryl
R$_1$ = H, Me, Et, Pr, i-Pr; Z = F, Cl, Br, I

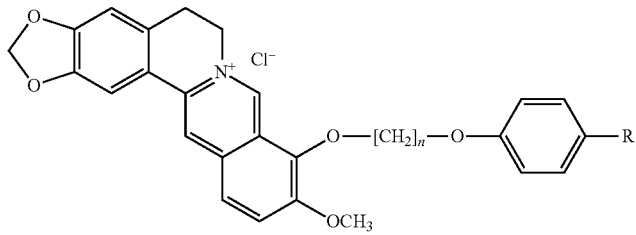

R = 2-acetic acid Me ester, 3-acetic Me ester, 4-acetic Me ester, 2-acetic Me Et ester, 3-acetic Me Et ester, 4-acetic Me Et ester, 2-acetate, 3-acetate, 4-acetate, 2-acetate potassium, 3-acetate potassium, 4-acetate potassium; n = 2-6

In certain embodiments, the pharmacologically active organic acid(s) is one or more agents selected from the group consisting of -(+)-α-lipoic acid, hydroxycitric acid, eicosapentaenoic acid, docosahexaenoic acid, docosapentaenoic acid, ursolic acid, corosolic acid, cinnamic acid, cholic acid, obeticholic acid, ursodeoxycholic acid, oleanolic acid, salicylic acid, betulinic acid, chlorogenic acid, caffeic acid, bassic acid, acetyl L-carnitine, S-allyl cysteine sulphoxide, S-methyl cysteine sulfoxide, pantothenic acid, ascorbic acid, retinoic acid, rhein, nicotinic acid, biotin and other organic acid that is generally recognized pharmacologically active for one or more diseases or disorders selected from metabolic disorders, heart diseases, neurodegenerative diseases, liver diseases, muscle atrophy, inflammation, and cancer, or a related disease or disorder thereof in a mammal, including a human by those of skill in the art.

In certain embodiments, the composition further includes one or more additional agent(s) selected from the group consisting of vitamin D, vitamin C, vitamin E, vitamin B12, vitamin A, benfotiamine, chromium picolinate and vanadium.

In certain embodiments, the disease or disorder is a metabolic disorder and is selected from diabetes, diabetic complications, dyslipidemia, obesity, metabolic syndromes, pre-diabetes, fatty liver, NAFLD and NASH. In certain embodiments, the disease or disorder is heart diseases. In certain embodiments, the disease or disorder is neurodegenerative diseases. In certain embodiments, the disease or disorder is cancer. In certain embodiments, the cancer is selected from the group consisting of breast cancer, prostate cancer, lung cancer, hepatocellular carcinoma, pancreatic cancer, gastric carcinoma, colorectal cancer, leukemia, multiple myeloma, melanoma and glioblastoma. In certain embodiments, the disease or disorder is muscle atrophy. In certain embodiments, the disease or disorder is muscle atrophy is selected from skeletal muscle atrophy.

In certain embodiments, the composition further includes a pharmaceutically acceptable excipient, carrier, or diluent.

In certain preferred embodiments, the composition includes berberine and -(+)-α-Lipoic acid. In certain preferred embodiments, the composition includes berberine, -(+)-α-Lipoic acid and vitamin D. In certain preferred embodiments, the composition includes berberine, -(+)-α-Lipoic acid and vitamin B12. In certain preferred embodiments, the composition includes berberine, -(+)-α-Lipoic acid, vitamin B12 and benfotiamine. In certain preferred embodiments, the composition includes berberine, -(+)-α-Lipoic acid, vitamin B12, benfotiamine and omega-3 polyunsaturated fatty acids.

In certain preferred embodiments, the composition includes berberine and hydroxycitric acid. In certain preferred embodiments, the composition includes berberine, hydroxycitric acid and vitamin D. In certain preferred embodiments, the composition includes berberine, hydroxycitric acid, vitamin D and omega-3 polyunsaturated fatty acids. In certain preferred embodiments, the composition includes berberine, extracts from *Garcinia cambogia* or *Hibiscus subdariffa* (hydroxycitric acid), vitamin D and omega-3 polyunsaturated fatty acids.

In certain preferred embodiments, the composition includes berberine and one or both of EPA and DHA. In certain preferred embodiments, the composition includes berberine, one or both of EPA and DHA and vitamin D.

In certain preferred embodiments, the composition includes berberine and ursolic acid. In certain preferred embodiments, the composition includes berberine, ursolic acid and/or corosolic acid and vitamin D. In certain preferred embodiments, the composition includes berberine, ursolic acid and/or corosolic acid, vitamin D and omega-3 polyunsaturated fatty acids. In certain preferred embodiments, the composition includes berberine, banaba extracts (corosolic acid), Holy Basil or apple peels extracts (ursolic acid), vitamin D and omega-3 polyunsaturated fatty acids.

In certain preferred embodiments, the composition includes berberine and cinnamic acid. In certain preferred embodiments, the composition includes berberine, cinnamic acid and vitamin D. In certain preferred embodiments, the composition includes berberine, cinnamic acid, vitamin D and omega-3 polyunsaturated fatty acids.

In certain preferred embodiments, the composition includes berberine and bile acid(s) (e.g., cholic acid, obeticholic acid and/or ursodeoxycholic acid). In certain preferred embodiments, the composition includes berberine, bile acid(s) (e.g., cholic acid, obeticholic acid and/or ursodeoxycholic acid) and vitamin D. In certain preferred embodiments, the composition includes berberine, bile acid(s) (e.g., cholic acid, obeticholic acid and/or ursodeoxycholic acid), vitamin D and omega-3 polyunsaturated fatty acids.

In certain preferred embodiments, the composition includes berberine and oleanolic acid. In certain preferred embodiments, the composition includes berberine, oleanolic acid and vitamin D. In certain preferred embodiments, the composition includes berberine, oleanolic acid, vitamin D and omega-3 polyunsaturated fatty acids.

In certain preferred embodiments, the composition includes berberine and salicylic acid. In certain preferred embodiments, the composition includes berberine, salicylic acid and vitamin D. In certain preferred embodiments, the composition includes berberine, salicylic acid, vitamin D and omega-3 polyunsaturated fatty acids.

In certain preferred embodiments, the composition includes berberine and betulinic acid. In certain preferred embodiments, the composition includes berberine, betulinic acid and vitamin D. In certain preferred embodiments, the composition includes berberine, betulinic acid, vitamin D and omega-3 polyunsaturated fatty acids.

In certain preferred embodiments, the composition includes berberine and chlorogenic acid. In certain preferred embodiments, the composition includes berberine, chlorogenic acid and vitamin D. In certain preferred embodiments, the composition includes berberine, chlorogenic acid, vitamin D and omega-3 polyunsaturated fatty acids.

In certain preferred embodiments, the composition includes berberine and caffeic acid. In certain preferred embodiments, the composition includes berberine, caffeic acid and vitamin D. In certain preferred embodiments, the composition includes berberine, caffeic acid, vitamin D and omega-3 polyunsaturated fatty acids.

In certain preferred embodiments, the composition includes berberine and bassic acid. In certain preferred embodiments, the composition includes berberine, bassic acid and vitamin D. In certain preferred embodiments, the composition includes berberine, bassic acid, vitamin D and omega-3 polyunsaturated fatty acids.

In certain preferred embodiments, the composition includes berberine and acetyl L-carnitine. In certain preferred embodiments, the composition includes berberine, acetyl L-carnitine and vitamin D. In certain preferred embodiments, the composition includes berberine, acetyl L-carnitine, vitamin D and omega-3 polyunsaturated fatty acids.

In certain preferred embodiments, the composition includes berberine and S-allyl cysteine sulphoxide and/or S-methyl cysteine sulfoxide. In certain preferred embodiments, the composition includes berberine, S-allyl cysteine sulphoxide and/or S-methyl cysteine sulfoxide and vitamin D. In certain preferred embodiments, the composition includes berberine, S-allyl cysteine sulphoxide and/or S-methyl cysteine sulfoxide, vitamin D and omega-3 polyunsaturated fatty acids.

In certain preferred embodiments, the composition includes berberine and pantothenic acid. In certain preferred embodiments, the composition includes berberine, pantothenic acid and vitamin D. In certain preferred embodiments, the composition includes berberine, pantothenic acid, vitamin D and omega-3 polyunsaturated fatty acids.

In certain preferred embodiments, the composition includes berberine and ascorbic acid. In certain preferred embodiments, the composition includes berberine, ascorbic acid and vitamin D. In certain preferred embodiments, the composition includes berberine, ascorbic acid, vitamin D and omega-3 polyunsaturated fatty acids.

In certain preferred embodiments, the composition includes berberine and retinoic acid. In certain preferred embodiments, the composition includes berberine, retinoic acid and vitamin D. In certain preferred embodiments, the composition includes berberine, retinoic acid, vitamin D and omega-3 polyunsaturated fatty acids.

In certain preferred embodiments, the composition includes berberine and rhein. In certain preferred embodiments, the composition includes berberine, rhein and vitamin D. In certain preferred embodiments, the composition includes berberine, rhein, vitamin D and omega-3 polyunsaturated fatty acids. In certain preferred embodiments, the composition includes berberine, rhubarb extracts (rhein), vitamin D and omega-3 polyunsaturated fatty acids.

In certain preferred embodiments, the composition includes berberine and nicotinic acid. In certain preferred embodiments, the composition includes berberine, nicotinic acid and vitamin D. In certain preferred embodiments, the composition includes berberine, nicotinic acid, vitamin D and omega-3 polyunsaturated fatty acids.

In certain preferred embodiments, the composition includes berberine and biotin. In certain preferred embodiments, the composition includes berberine, biotin and vitamin D. In certain preferred embodiments, the composition includes berberine, biotin, vitamin D and omega-3 polyunsaturated fatty acids.

In another aspect, the invention generally relates to a method for treating, reducing, or preventing a metabolic disorder. The method includes administering to a subject in need thereof a pharmaceutical composition, which includes: (a) berberine or a derivative or analog thereof; (b) one or more pharmacologically active organic acids, in a therapeutically effective amount, and (c) optionally a pharmaceutically acceptable excipient, carrier, or diluent.

In certain embodiments, the metabolic disorder is selected from diabetes, diabetic complications, dyslipidemia, diabetic dyslipidemia, dyslipidemia in statin-intolerance patients, hyperlipidemia, obesity, metabolic syndromes, pre-diabetes, fatty liver, NAFLD and NASH.

In certain preferred embodiments, the metabolic disorder is type 2 diabetes.

In certain preferred embodiments, the diabetic complications are diabetic neuropathy, diabetic retinopathy or diabetic nephropathy.

In certain preferred embodiments, the hyperlipidemia is hypercholesterolemia, hypertriglyceridemia, or both.

In certain preferred embodiments, the pharmacologically active organic acid is selected from the group consisting of -(+)-α-lipoic acid, hydroxycitric acid, eicosapentaenoic acid, docosahexaenoic acid, docosapentaenoic acid, ursolic acid, corosolic acid, cinnamic acid, cholic acid, obeticholic acid, ursodeoxycholic acid, oleanolic acid, salicylic acid, betulinic acid, chlorogenic acid, caffeic acid, bassic acid, acetyl L-carnitine, S-allyl cysteine sulphoxide, S-methyl cysteine sulfoxide, pantothenic acid, ascorbic acid, retinoic acid, rhein, nicotinic acid and biotin. In certain embodiments, the pharmaceutical composition further comprises a third agent selected from the group consisting of vitamin D, vitamin C, vitamin E, vitamin B12, vitamin A, benfotiamine, chromium picolinate and vanadium.

In certain preferred embodiments of the method, the subject suffers from diabetes and diabetic complications and the pharmaceutical composition comprises berberine and -(+)-α-lipoic acid. In certain preferred embodiments of the method, the subject suffers from diabetic nephropathy and the pharmaceutical composition comprises berberine and rhein (or rhubarb extracts). In certain preferred embodiments of the method, the subject suffers from diabetes and obesity and the pharmaceutical composition comprises berberine and hydroxycitric acid (or *Garcinia cambogia* extracts). In certain preferred embodiments of the method, the subject suffers from diabetes and dyslipidemia and the pharmaceutical composition comprises berberine and one or more of EPA, DHA and DPA.

In certain preferred embodiments of the method, the subject suffers from diabetes and muscle atrophy and the pharmaceutical composition comprises berberine and one or both of ursolic acid and corosolic acid. In certain preferred embodiments of the method, the subject suffers from diabetes and muscle atrophy, and the pharmaceutical composition comprises berberine and one or both of Holy Basil or apple peels extracts (ursolic acid) and banaba extracts (corosolic acid).

In certain preferred embodiments of the method, the subject suffers from fatty liver, NAFLD and NSAH, and the pharmaceutical composition comprises berberine and one or more of cholic acid, obeticholic acid and ursodeoxycholic acid. In certain preferred embodiments of the method, the subject suffers from fatty liver, NAFLD and NSAH, and the pharmaceutical composition comprises berberine and bile acids.

In certain preferred embodiments of the method, the pharmaceutical composition includes further comprises vitamin D.

In certain preferred embodiments of the method, the pharmaceutical composition further includes vitamin E.

In certain preferred embodiments of the method, the pharmaceutical composition further includes vitamin B12.

In certain preferred embodiments of the method, the pharmaceutical composition further includes benfotiamine.

In certain preferred embodiments of the method, the pharmaceutical composition further includes vitamin C.

In certain preferred embodiments of the method, the pharmaceutical composition further includes vitamin A.

In certain preferred embodiments of the method, the pharmaceutical composition further includes benfotiamine.

In certain preferred embodiments of the method, the pharmaceutical composition further includes chromium picolinate.

In certain preferred embodiments of the method, the pharmaceutical composition further includes vanadium.

In certain preferred embodiments of the method, treating, reducing, or preventing a metabolic disorder is by reducing blood glucose levels of the subject. In certain preferred embodiments of the method, treating, reducing, or preventing a metabolic disorder is by reducing total cholesterol (TC), triglyceride (TG) and low-density lipoprotein cholesterol (LDL-c) levels, increasing high-density lipoprotein cholesterol (HDL-c) levels of the subject. In certain preferred embodiments of the method, treating, reducing, or preventing a metabolic disorder is by normalizing liver enzyme levels of the subject. In certain preferred embodiments of the method, treating, reducing, or preventing a metabolic disorder is by altering insulin signaling pathway such that glucose levels are reduced. In certain preferred embodiments of the method, treating, reducing, or preventing a metabolic disorder is by regulating multiple metabolic pathways such as increasing secretion of insulin, improving insulin sensitivity, reducing gluconeogenesis in liver, reducing glucose absorption, ameliorating dyslipidemia, anti-inflammation to achieve the desired pharmacological effects.

In yet another aspect, the invention generally relates to a kit that includes: (i) an agent of berberine or a derivative or analog thereof; (ii) one or more agent(s) selected from pharmaceutically active organic acids; and (iii) instructions for administering the combined agents to a patient having or at risk of having one or more diseases or disorders selected from metabolic disorders, heart diseases, neurodegenerative diseases, liver diseases, muscle atrophy, and cancer.

In certain embodiments, the derivative or analog of berberine is selected Table 2. In certain embodiments, additional agent is selected from any one or more of the agents of -(+)-α-lipoic acid, hydroxycitric acid, eicosapentaenoic acid, docosahexaenoic acid, docosapentaenoic acid, ursolic acid, corosolic acid, cholic, ursodeoxycholic acid or the others listed in Table 1.

Salts of Ursodeoxycholic Acid or Derivatives

The invention also provides novel salts of ursodeoxycholic acid and organic bases, pharmaceutical compositions thereof, as well as related methods of preparation and use in treating and/or preventing various liver diseases or disorders, and metabolic disorders. Salts of ursodeoxycholic acid include those with organic bases such as berberine, metformin, carnitine, coptisine, palmatine, jatrorrhizine.

In yet another aspect, the present invention generally relates to an acid-base addition salt in substantially pure form, having the formula of:

$$(X^+)_m(U^-)_n \qquad (I)$$

wherein (a) U⁻ is an anionic moiety of ursodeoxycholic acid or a derivative or analog thereof;

(b) X⁺ is a cationic moiety of a pharmacologically active organic base; and (c) m and n are integers independently selected from 1, 2, 3, 4, 5 and 6 so as to arrive at a charge neutral salt.

U⁻ can be an anionic moiety of any suitable derivative or analog of ursodeoxycholic, for example, selected from Table 3.

X+ can be a cationic moiety of any suitable pharmacologically active organic base. In certain embodiments, for example, the pharmacologically active organic base may be selected from the group consisting of berberine, metformin, carnitine and coptisine, palmatine, jatrorrhizine. In certain embodiments, X+ can also be a cationic moiety of other organic base that is generally recognized pharmacologically active for one or more diseases or disorders selected from various liver diseases or disorders such as fatty liver, NAFLD, NASH, cholestatic liver diseases, graft-versus-host disease of the liver, chronic viral associated liver diseases, alcohol-related liver diseases, metabolic diseases or disorders such as pre-diabetes, diabetes, dyslipidemia, diabetic dyslipidemia, hyperlipidemia, obesity, or a related disease or disorder thereof in a mammal, including a human.

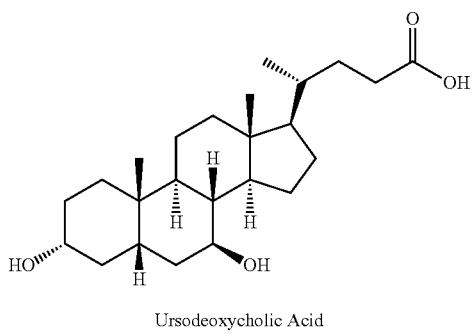

Ursodeoxycholic Acid

Ursodeoxycholic acid (UDCA or ursodiol, with the chemical names of 3α,7β-dihydroxy-5β-cholan-24-oic acid or (R)-4-((3R,5S,7S,8R,9S,10S,13R,14S,17R)-3,7-dihydroxy-10,13-dimethylhexadecahydro-1H-cyclopenta[a]phenanthren-17-yl)pentanoic acid) is a secondary bile acid, a substance naturally produced by the body that is stored in the gallbladder. Ursodiol is used to dissolve gallstones in patients as an alternative to surgery. Ursodiol is also used to prevent the formation of gallstones in overweight patients who are losing weight very quickly. Ursodiol works by decreasing the production of cholesterol and by dissolving the cholesterol in bile so that it cannot form stones. Ursodiol is also the first-line therapy for the treatment of PBC, PSC and cholestatic liver diseases. There have been limited studies of ursodiol on NASH, but the results were contradictory and inconclusive. Thus, the effect of ursodiol on NASH remains unclear.

Metformin (N,N-Dimethylimidodicarbonimidic diamide) is a potent anti-hyperglycemic agent now recommended as the first line oral therapy for type 2 diabetes (T2D). The main effect of this drug is to acutely decrease hepatic glucose production, mostly through a mild and transient inhibition of the mitochondrial respiratory-chain complex 1. In addition, the resulting decrease in hepatic energy status activates the AMP-activated protein kinase (AMPK), a cellular metabolic sensor, providing a generally accepted mechanism for metformin action on hepatic gluconeogenic program. Beyond its effect on glucose metabolism, metformin was reported to restore ovarian function in polycystic ovary syndrome, to reduce fatty liver and to lower microvascular and macrovascular complications associated with T2D. Its use was also recently suggested as an adjuvant treatment for cancer or gestational diabetes, and for the prevention in pre-diabetic populations. Studies of metformin for NAFLD and NASH have multiplied in the past few years, however, its efficacy for NAFLD and NASH remains to be approved.

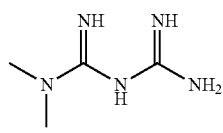

Metformin

Coptisine [6,7-Dihydro-bis(1,3)benzodioxolo (5,6-a:4',5'-g)quinolizinium], palmatine [2,3,9,10-tetramethoxy-5,6-dihydroisoquinolino[2,1-b]isoquinolin-7-ium], and jatrorrhizine [2,9,10-trimethoxy-5,6-dihydroisoquinolino[2,1-b]isoquinolin-7-ium-3-ol] are naturally alkaloids that have demonstrated similar pharmacological properties as berberine in previous studies.

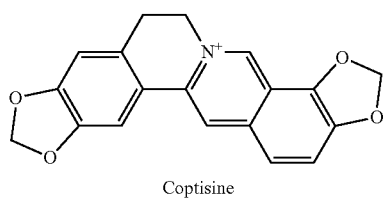

Coptisine

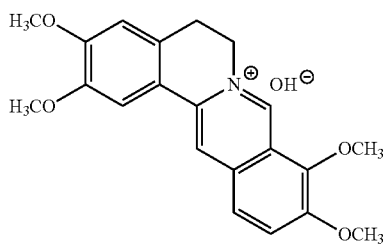

Palmatine

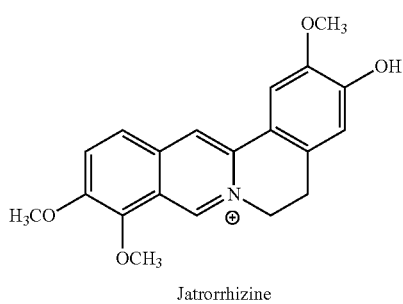

Jatrorrhizine

L-Carnitine is a naturally occurring amino acid. It is biosynthesized in the liver and kidneys from lysine and methionine. L-Carnitine plays an important role in the metabolism of fat, functioning as a transporter of fatty acids into the mitochondria.

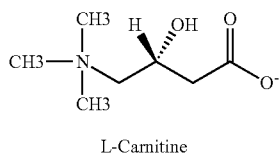

L-Carnitine

Exemplary derivatives or analogs of ursodeoxycholic acid are listed in Table 3.

TABLE 3
Ursodeoxycholic acid Derivatives or Analogs
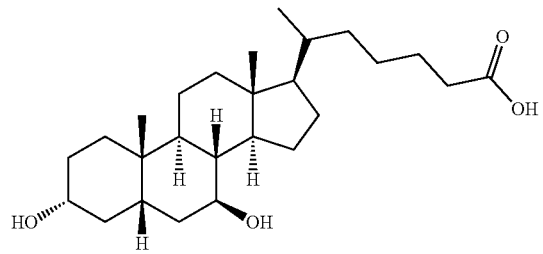
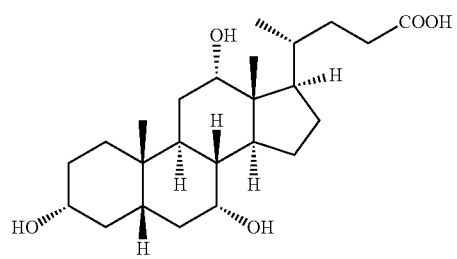
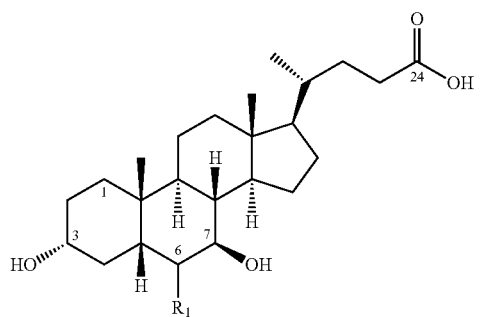
R₁ is selected from the group consisting of $C_1$-$C_4$ alkyl or a halogen; or an ester
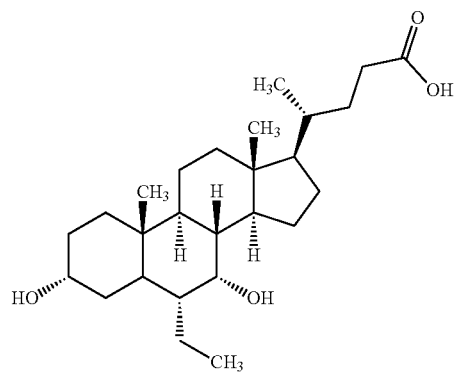

TABLE 3-continued
Ursodeoxycholic acid Derivatives or Analogs
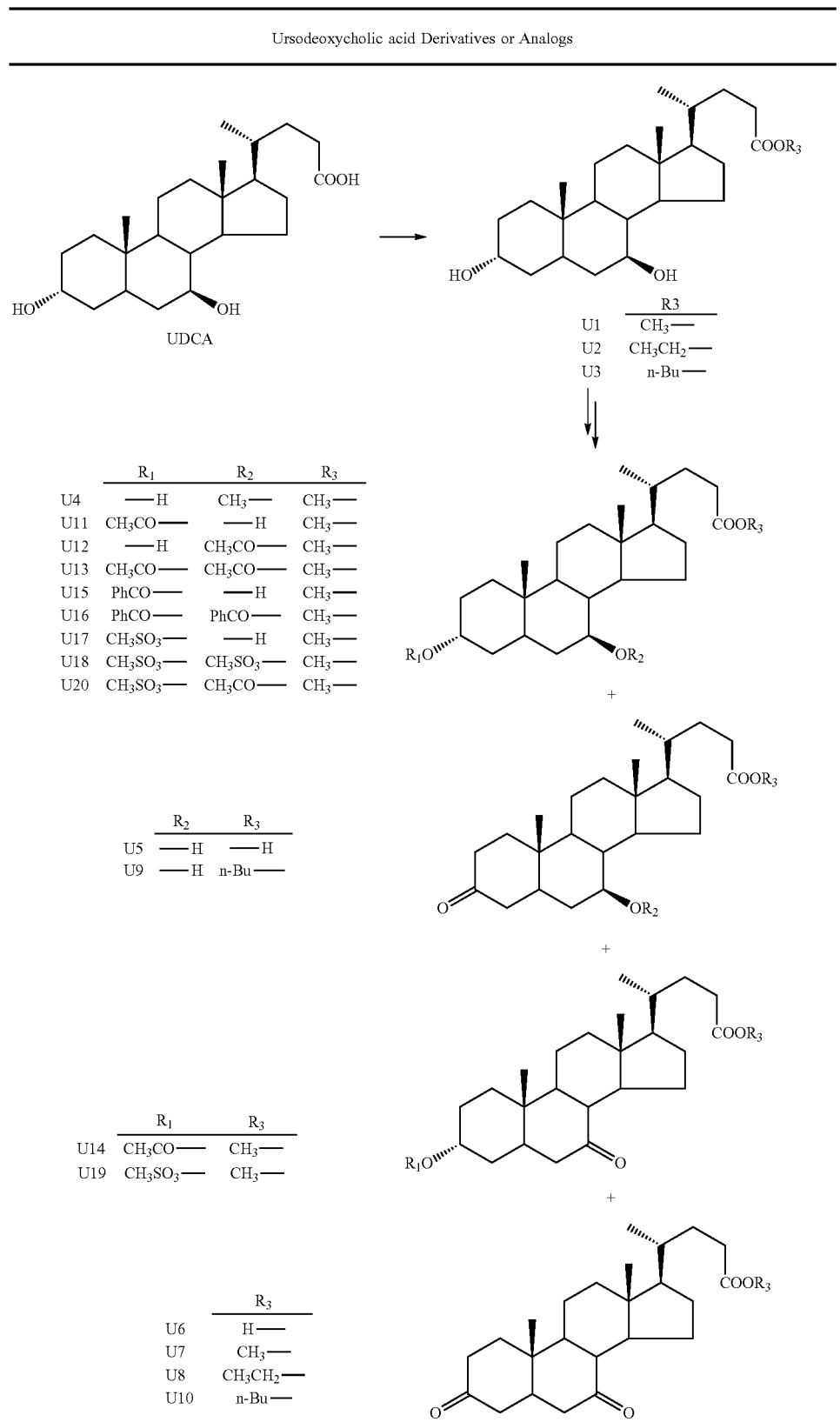
|    | R₁     | R₂     | R₃    |
|----|--------|--------|-------|
| U4 | —H     | CH₃—   | CH₃—  |
| U11| CH₃CO— | —H     | CH₃—  |
| U12| —H     | CH₃CO— | CH₃—  |
| U13| CH₃CO— | CH₃CO— | CH₃—  |
| U15| PhCO—  | —H     | CH₃—  |
| U16| PhCO—  | PhCO—  | CH₃—  |
| U17| CH₃SO₃—| —H     | CH₃—  |
| U18| CH₃SO₃—| CH₃SO₃—| CH₃—  |
| U20| CH₃SO₃—| CH₃CO— | CH₃—  |
|    | R₂  | R₃    |
|----|-----|-------|
| U5 | —H  | —H    |
| U9 | —H  | n-Bu— |
|    | R₁     | R₃   |
|----|--------|------|
| U14| CH₃CO— | CH₃— |
| U19| CH₃SO₃—| CH₃— |
|    | R₃       |
|----|----------|
| U6 | H—       |
| U7 | CH₃—     |
| U8 | CH₃CH₂—  |
| U10| n-Bu—    |

TABLE 3-continued
Ursodeoxycholic acid Derivatives or Analogs
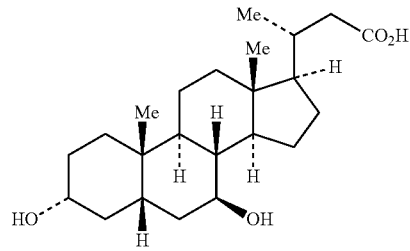
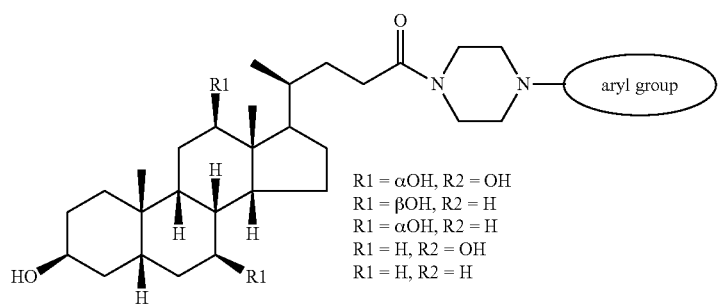
R1 = αOH, R2 = OH
R1 = βOH, R2 = H
R1 = αOH, R2 = H
R1 = H, R2 = OH
R1 = H, R2 = H
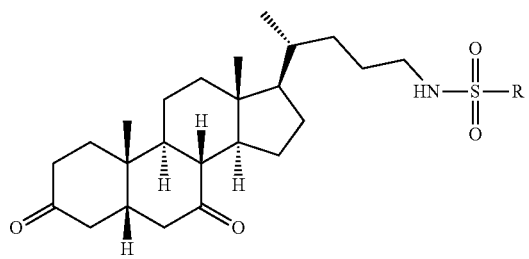
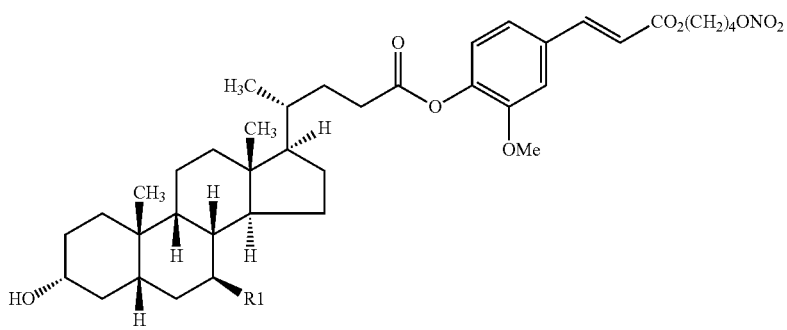
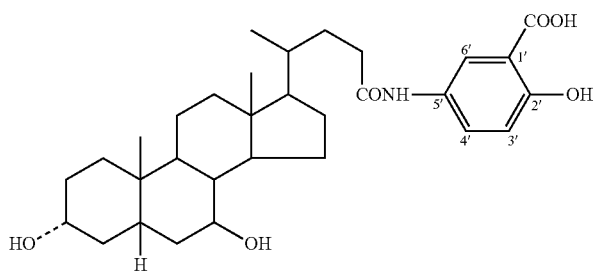

TABLE 3-continued

Ursodeoxycholic acid Derivatives or Analogs

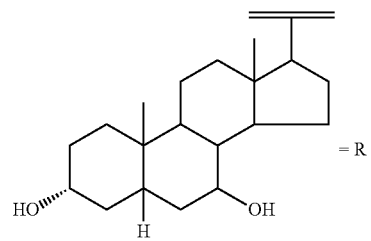

a: 7α   b: 7β

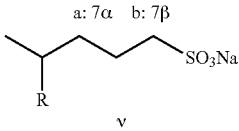

v

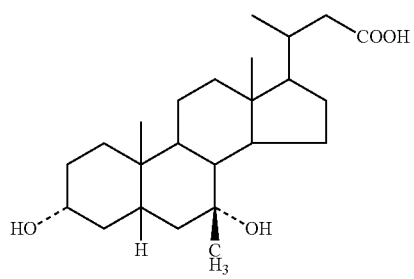

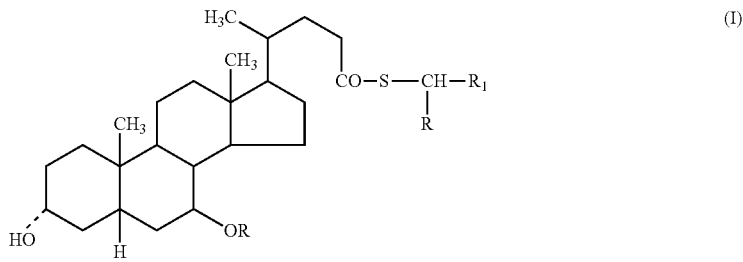

wherein R represents —H —CH3 or —COCH and $R_1$ represents —CONHCH$_2$COOH, —CH$_2$COOH or —CH—COCH | NH—COCH$_3$

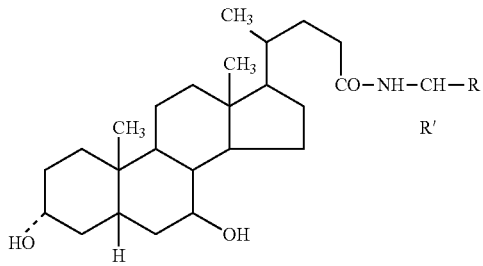

R is a radical selected from —CH2—SO$_3$H and —COOH and R' is a radical selected from —H and —(CH$_2$)$_2$—CONH, —CH$_2$—CONH$_1$, —(CH$_2$)$_2$—SCH$_3$, —CH$_2$—S—CH$_2$—COOH, respectively In certain preferred embodiments, U⁻ is an anionic moiety of ursodeoxycholic acid, X⁺ is a cationic moiety of berberine or a derivative or analog thereof, and m=1 and n=1. Exemplary derivatives or analogs of berberine are listed in Table 2. In certain preferred embodiments, U⁻ is an anionic moiety of ursodeoxycholic acid, X⁺ is a cationic moiety of berberine, and m=1 and n=1.

In certain preferred embodiments, U⁻ is an anionic moiety of ursodeoxycholic acid, X⁺ is a cationic moiety of metformin or a derivative or analog thereof, and m=1 and n=1.

Exemplary derivatives or analogs of metformin are listed in Table 4. In certain preferred embodiments, U⁻ is an anionic moiety of ursodeoxycholic acid, X⁺ is a cationic moiety of metformin, and m=1 and n=1.

In certain preferred embodiments, U⁻ is an anionic moiety of ursodeoxycholic acid, X⁺ is a cationic moiety of carnitine or a derivative or analog thereof, and m=1 and n=1. Exemplary derivatives or analogs of carnitine are listed in Table 5. In certain preferred embodiments, U⁻ is an anionic moiety of ursodeoxycholic acid, X⁺ is a cationic moiety of carnitine, and m=1 and n=1.

In certain preferred embodiments, U⁻ is an anionic moiety of ursodeoxycholic acid, X⁺ is a cationic moiety of coptisine or a derivative or analog thereof, and m=1 and n=1.

In certain preferred embodiments, U⁻ is an anionic moiety of ursodeoxycholic acid, X⁺ is a cationic moiety of palmatine or a derivative or analog thereof, and m=1 and n=1.

In certain preferred embodiments, U⁻ is an anionic moiety of ursodeoxycholic acid, X⁺ is a cationic moiety of jatrorrhizine or a derivative or analog thereof, and m=1 and n=1.

In certain preferred embodiments, U⁻ is an anionic moiety of obeticholic acid, X⁺ is a cationic moiety of berberine or a derivative or analog thereof, and m=1 and n=1. Exemplary derivatives or analogs of berberine are listed in Table 2. In certain preferred embodiments, U⁻ is an anionic moiety of obeticholic acid, X⁺ is a cationic moiety of berberine, and m=1 and n=1.

In certain preferred embodiments, U⁻ is an anionic moiety of obeticholic acid, X⁺ is a cationic moiety of metformin or a derivative or analog thereof, and m=1 and n=1. Exemplary derivatives or analogs of metformin are listed in Table 4. In certain preferred embodiments, U⁻ is an anionic moiety of obeticholic acid, X⁺ is a cationic moiety of metformin, and m=1 and n=1.

In certain preferred embodiments, U⁻ is an anionic moiety of obeticholic acid, X⁺ is a cationic moiety of carnitine or a derivative or analog thereof, and m=1 and n=1. Exemplary derivatives or analogs of carnitine are listed in Table 5. In certain preferred embodiments, U⁻ is an anionic moiety of obeticholic acid, X⁺ is a cationic moiety of carnitine, and m=1 and n=1.

In certain preferred embodiments, U⁻ is an anionic moiety of obeticholic acid, X⁺ is a cationic moiety of coptisine or a derivative or analog thereof, and m=1 and n=1.

In certain preferred embodiments, U⁻ is an anionic moiety of obeticholic acid, X⁺ is a cationic moiety of palmatine or a derivative or analog thereof, and m=1 and n=1.

In certain preferred embodiments, U⁻ is an anionic moiety of obeticholic acid, X⁺ is a cationic moiety of jatrorrhizine or a derivative or analog thereof, and m=1 and n=1.

TABLE 4

Metformin Derivatives or Analogs

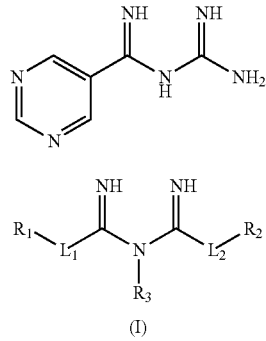

(I)

$L^1$ and $L^2$ are independently a bond or —NH—C(NH)—;

$R^1$ is —NR$^{1A}$R$^{1B}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl, wherein R$^{1A}$ and R$^{1B}$ are optionally joined together to form a substituted or unsubstituted heterocycloalkyl;

$R^2$ is —NR$^{1A}$R$^{1B}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl, wherein R$^{2A}$ and R$^{2B}$ are optionally joined together to form a substituted or unsubstituted heterocycloalkyl;

R$^{1A}$, R$^{1B}$, R$^{2A}$, and R$^{2B}$ are independently hydrogen, —OR$_4$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^3$ is hydrogen or unsubstituted $C_1$-$C_5$ alkyl; and $R^4$ is hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

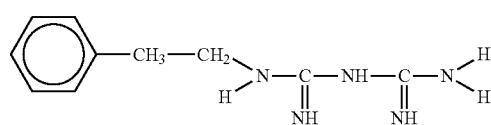

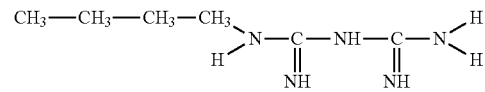

TABLE 4-continued

Metformin Derivatives or Analogs $$\begin{array}{c} CH_3 \\ CH_3 \end{array} C=CH-CH_2-NH-\underset{\underset{NH}{\parallel}}{C}-N\begin{array}{c} H \\ H \end{array}$$

$$R\underset{R'}{\overset{|}{N}}\underset{\parallel}{\overset{NH}{C}}\underset{H}{\overset{|}{N}}\underset{\parallel}{\overset{NH}{C}}NH_2$$

R' = —H, —Ph, substituted —Ph
R = $R_1$ substituted —Ph
$R_1$ = $C_1$-$C_6$ alkyl, $C_1$-$C_4$ alkyl, fluorinated alkyl, acyl, ester, aryl, halogen, $NO_2$, $NH_2$, —H, —$OR_2$, —$SR_2$
$R_2$ = $C_1$-$C_6$ alkyl, $C_1$-$C_4$ fluorinated alkyl, acyl

TABLE 5

L-carnitine Derivatives or Analogs

[Structure of acetyl-L-carnitine]

[Structure of propionyl-L-carnitine]

[Structure of Analog 2: phosphonate derivative with I⁻ⁱNMe₃]

Analog 2

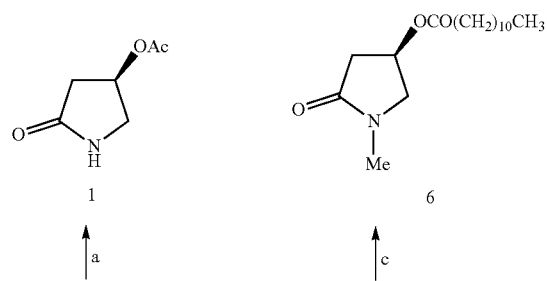

1        6

↑a        ↑c

TABLE 5-continued

L-carnitine Derivatives or Analogs

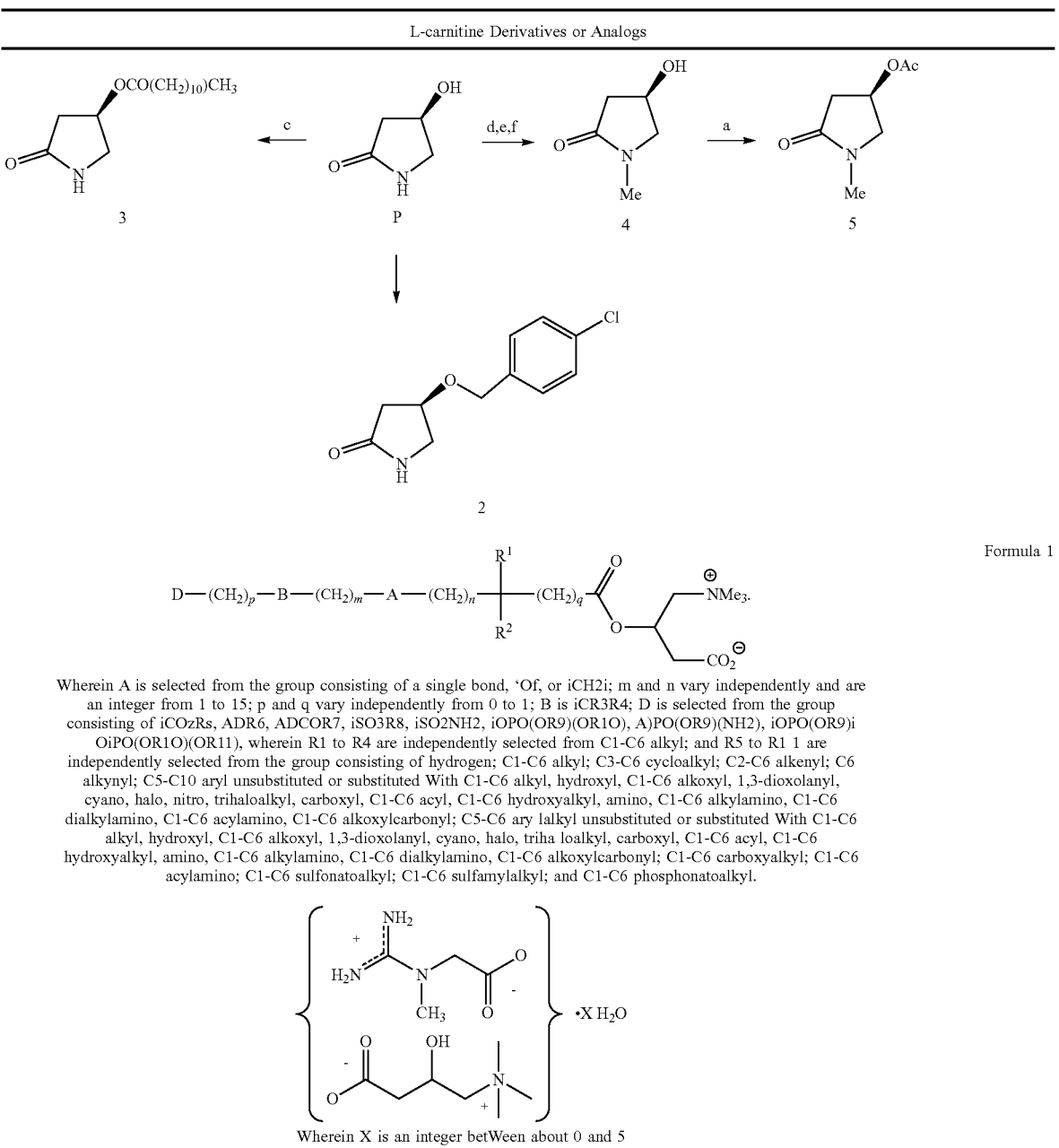

Wherein A is selected from the group consisting of a single bond, 'Of, or iCH2i; m and n vary independently and are an integer from 1 to 15; p and q vary independently from 0 to 1; B is iCR3R4; D is selected from the group consisting of iCOzRs, ADR6, ADCOR7, iSO3R8, iSO2NH2, iOPO(OR9)(OR1O), A)PO(OR9)(NH2), iOPO(OR9)i OiPO(OR1O)(OR11), wherein R1 to R4 are independently selected from C1-C6 alkyl; and R5 to R1 1 are independently selected from the group consisting of hydrogen; C1-C6 alkyl; C3-C6 cycloalkyl; C2-C6 alkenyl; C6 alkynyl; C5-C10 aryl unsubstituted or substituted With C1-C6 alkyl, hydroxyl, C1-C6 alkoxyl, 1,3-dioxolanyl, cyano, halo, nitro, trihaloalkyl, carboxyl, C1-C6 acyl, C1-C6 hydroxyalkyl, amino, C1-C6 alkylamino, C1-C6 dialkylamino, C1-C6 acylamino, C1-C6 alkoxylcarbonyl; C5-C6 ary lalkyl unsubstituted or substituted With C1-C6 alkyl, hydroxyl, C1-C6 alkoxyl, 1,3-dioxolanyl, cyano, halo, triha loalkyl, carboxyl, C1-C6 acyl, C1-C6 hydroxyalkyl, amino, C1-C6 alkylamino, C1-C6 dialkylamino, C1-C6 alkoxylcarbonyl; C1-C6 carboxyalkyl; C1-C6 acylamino; C1-C6 sulfonatoalkyl; C1-C6 sulfamylalkyl; and C1-C6 phosphonatoalkyl.

Wherein X is an integer betWeen about 0 and 5

In yet another aspect, the invention generally relates to a pharmaceutical composition comprising an amount of an acid-base addition salt having the formula of:

$$(X^+)_m (U^-)_n \quad (I)$$

wherein (a) $U^-$ is an anionic moiety of ursodeoxycholic acid or a derivative or analog thereof, (b) $X^+$ is a cationic moiety of a pharmacologically active organic base; and (c) m and n are integers independently selected from 1, 2, 3, 4, 5 and 6 so as to arrive at a charge neutral salt, effective to treat, prevent, or reduce one or more diseases or disorders selected from fatty liver, NAFLD and NASH, cholestatic liver diseases, graft-versus-host disease of the liver, chronic viral associated liver diseases, alcohol-related liver diseases, metabolic diseases or disorders such as pre-diabetes, diabetes, diabetic dyslipidemia, dyslipidemia in statin-intolerant patients, hyperlipidemia, obesity, or a related disease or disorder thereof in a mammal, including a human, and a pharmaceutically acceptable excipient, carrier, or diluent.

In certain preferred embodiments, the pharmaceutical composition of the invention is used to treat, prevent, or reduce NASH. In certain preferred embodiments, the pharmaceutical composition of the invention is used to treat, prevent, or reduce NAFLD. In certain preferred embodiments, the pharmaceutical composition of the invention is used to treat, prevent, or reduce fatty liver. In certain preferred embodiments, the pharmaceutical composition of the invention is used to treat, prevent, or reduce a disease or disorder selected from cholestatic liver diseases, graft-versus-host disease of the liver, chronic viral associated liver diseases, alcohol-related liver diseases, metabolic diseases or disorders such as pre-diabetes, diabetes, diabetic dyslipidemia, dyslipidemia in statin-intolerant patients, hyperlipidemia, or obesity.

In the context of the pharmaceutical composition of the invention, U⁻ can be an anionic moiety of any suitable derivative or analog of ursodeoxycholic, for example, selected from Table 3. X⁺ can be a cationic moiety of any suitable pharmacologically active organic base. In certain embodiments, for example, the pharmacologically active organic base may be selected from the group consisting of berberine, metformin, carnitine, coptisine, palmatine, and jatrorrhizine. In certain embodiments, X⁺ can also be a cationic moiety of other organic base that is generally recognized pharmacologically active for one or more diseases or disorders selected from fatty liver, NAFLD, NASH, cholestatic liver diseases or graft-versus-host disease of the liver, chronic viral associated liver diseases, alcohol-related liver diseases, metabolic diseases or disorders such as pre-diabetes, diabetes, diabetic dyslipidemia, dyslipidemia in statin-intolerant patients, hyperlipidemia, obesity, or a related disease or disorder thereof in a mammal, including a human.

In the context of the pharmaceutical composition of the invention, in certain preferred embodiments, U⁻ is an anionic moiety of ursodeoxycholic acid, X⁺ is a cationic moiety of berberine or a derivative or analog thereof, and m=1 and n=1. Exemplary derivatives or analogs of berberine are listed in Table 2. In certain preferred embodiments, U⁻ is an anionic moiety of ursodeoxycholic acid, X⁺ is a cationic moiety of berberine, and m=1 and n=1. In certain preferred embodiments, U⁻ is an anionic moiety of ursodeoxycholic acid, X⁺ is a cationic moiety of metformin or a derivative or analog thereof, and m=1 and n=1. Exemplary derivatives or analogs of metformin are listed in Table 4. In certain preferred embodiments, U⁻ is an anionic moiety of ursodeoxycholic acid, X⁺ is a cationic moiety of metformin, and m=1 and n=1. In certain preferred embodiments, U⁻ is an anionic moiety of ursodeoxycholic acid, X⁺ is a cationic moiety of coptisine, and m=1 and n=1. In certain preferred embodiments, U⁻ is an anionic moiety of ursodeoxycholic acid, X⁺ is a cationic moiety of palmatine, and m=1 and n=1. In certain preferred embodiments, U⁻ is an anionic moiety of ursodeoxycholic acid, X⁺ is a cationic moiety of jatrorrhizine, and m=1 and n=1.

In the context of the pharmaceutical composition of the invention, in certain preferred embodiments, U⁻ is an anionic moiety of obeticholic acid, X⁺ is a cationic moiety of berberine or a derivative or analog thereof, and m=1 and n=1. Exemplary derivatives or analogs of berberine are listed in Table 2. In certain preferred embodiments, U⁻ is an anionic moiety of obeticholic acid, X⁺ is a cationic moiety of berberine, and m=1 and n=1. In certain preferred embodiments, U⁻ is an anionic moiety of obeticholic acid, X⁺ is a cationic moiety of metformin or a derivative or analog thereof, and m=1 and n=1. Exemplary derivatives or analogs of metformin are listed in Table 4. In certain preferred embodiments, U⁻ is an anionic moiety of obeticholic acid, X⁺ is a cationic moiety of metformin, and m=1 and n=1. In certain preferred embodiments, U⁻ is an anionic moiety of obeticholic acid, X⁺ is a cationic moiety of coptisine, and m=1 and n=1. In certain preferred embodiments, U⁻ is an anionic moiety of obeticholic acid, X⁺ is a cationic moiety of palmatine, and m=1 and n=1. In certain preferred embodiments, U⁻ is an anionic moiety of obeticholic acid, X⁺ is a cationic moiety of jatrorrhizine, and m=1 and n=1.

In certain preferred embodiments, the pharmaceutical composition further includes a compound selected from the group consisting of vitamin E, omega-3 fatty acids, S-adenosylmethionine, N-acetyl cysteine, silymarin, polyenylphosphatidylcholine, resveratrol or vitamin D.

In yet another aspect, the invention generally relates to a method for treating, reducing, or preventing a disease or disorder. The method includes administering to a subject in need thereof a pharmaceutical composition comprising an amount of an acid-base addition salt having the formula of:

$$(X^+)_m(U^-)_n \qquad (I)$$

wherein
(a) U⁻ is an anionic moiety of ursodeoxycholic acid or a derivative or analog thereof;
(b) X⁺ is a cationic moiety of a pharmacologically active organic base; and
(c) m and n are integers independently selected from 1, 2, 3, 4, 5 and 6 so as to arrive at a charge neutral salt,
effective to treat, prevent, or reduce one or more diseases or disorders selected from fatty liver, NAFLD, NASH, cholestatic liver diseases, graft-versus-host disease of the liver, chronic viral associated liver diseases, alcohol-related liver diseases, metabolic diseases or disorders such as pre-diabetes, diabetes, diabetic dyslipidemia, dyslipidemia in statin-intolerant patients, hyperlipidemia, obesity, or a related disease or disorder thereof in a mammal, including a human, and a pharmaceutically acceptable excipient, carrier, or diluent.

In certain preferred embodiments, the method is to treat, prevent, or reduce NASH. In certain preferred embodiments, the method is to treat, prevent, or reduce NAFLD. In certain preferred embodiments, the method is to treat, prevent, or reduce fatty liver. In certain preferred embodiments, the method is to treat, prevent, or reduce a disease or disorder selected from cholestatic liver diseases, graft-versus-host disease of the liver, chronic viral associated liver diseases, alcohol-related liver diseases, metabolic diseases or disorders such as pre-diabetes, diabetes, diabetic dyslipidemia, dyslipidemia in statin-intolerant patients, hyperlipidemia, obesity, or a related disease or disorder.

In the context of the method of the invention, U⁻ can be an anionic moiety of any suitable derivative or analog of ursodeoxycholic, for example, selected from Table 3. X⁺ can be a cationic moiety of any suitable pharmacologically active organic base. In certain embodiments, for example, the pharmacologically active organic base may be selected from the group consisting of berberine, metformin, carnitine and coptisine, palmatine, and jatrorrhizine. In certain embodiments, X⁺ can also be a cationic moiety of other organic base that is generally recognized pharmacologically active for one or more diseases or disorders selected from fatty liver, NAFLD and NASH, cholestatic liver diseases, graft-versus-host disease of the liver, chronic viral associated liver diseases, alcohol-related liver diseases, metabolic diseases or disorders such as pre-diabetes, diabetes, diabetic dyslipidemia, dyslipidemia in statin-intolerant patients, hyperlipidemia, obesity, or a related disease or disorder thereof in a mammal, including a human.

In the context of the method of the invention, in certain preferred embodiments, U⁻ is an anionic moiety of ursodeoxycholic acid, X⁺ is a cationic moiety of berberine or a derivative or analog thereof, and m=1 and n=1. Exemplary derivatives or analogs of berberine are listed in Table 2. In certain preferred embodiments, U⁻ is an anionic moiety of ursodeoxycholic acid, X⁺ is a cationic moiety of berberine, and m=1 and n=1. In certain preferred embodiments, U⁻ is an anionic moiety of ursodeoxycholic acid, X⁺ is a cationic moiety of metformin or a derivative or analog thereof, and m=1 and n=1. Exemplary derivatives or analogs of metformin are listed in Table 4. In certain preferred embodiments, U⁻ is an anionic moiety of ursodeoxycholic acid, X⁺ is a cationic moiety of metformin, and m=1 and n=1. In certain preferred embodiments, U⁻ is an anionic moiety of ursodeoxycholic acid, X⁺ is a cationic moiety of carnitine or a derivative or analog thereof, and m=1 and n=1. Exemplary derivatives or analogs of carnitine are listed in Table 5. In certain preferred embodiments, U⁻ is an anionic moiety of ursodeoxycholic acid, X⁺ is a cationic moiety of carnitine, and m=1 and n=1. In certain preferred embodiments, U⁻ is an anionic moiety of ursodeoxycholic acid, X⁺ is a cationic moiety of coptisine, and m=1 and n=1. In certain preferred embodiments, U⁻ is an anionic moiety of ursodeoxycholic acid, X⁺ is a cationic moiety of palmatine, and m=1 and n=1. In certain preferred embodiments, U⁻ is an anionic moiety of ursodeoxycholic acid, X⁺ is a cationic moiety of jatrorrhizine, and m=1 and n=1. In certain preferred embodiments, the pharmaceutical composition further includes a compound selected from the group consisting of vitamin E, omega-3 fatty acids, S-adenosylmethionine, N-acetyl cysteine, silymarin, polyenylphosphatidylcholine, resveratrol or vitamin D. In certain preferred embodiments, treating, reducing, or preventing a disease or disorder is by normalizing liver enzyme levels of the subject.

In the context of the method of the invention, in certain preferred embodiments, U⁻ is an anionic moiety of obeticholic acid, X⁺ is a cationic moiety of berberine or a derivative or analog thereof, and m=1 and n=1. Exemplary derivatives or analogs of berberine are listed in Table 2. In certain preferred embodiments, U⁻ is an anionic moiety of obeticholic acid, X⁺ is a cationic moiety of berberine, and m=1 and n=1. In certain preferred embodiments, U⁻ is an anionic moiety of obeticholic acid, X⁺ is a cationic moiety of metformin or a derivative or analog thereof, and m=1 and n=1. Exemplary derivatives or analogs of metformin are listed in Table 4. In certain preferred embodiments, U⁻ is an anionic moiety of obeticholic acid, X⁺ is a cationic moiety of metformin, and m=1 and n=1. In certain preferred embodiments, U⁻ is an anionic moiety of obeticholic acid, X⁺ is a cationic moiety of carnitine or a derivative or analog thereof, and m=1 and n=1. Exemplary derivatives or analogs of carnitine are listed in Table 5. In certain preferred embodiments, U⁻ is an anionic moiety of obeticholic acid, X⁺ is a cationic moiety of carnitine, and m=1 and n=1. In certain preferred embodiments, U⁻ is an anionic moiety of obeticholic acid, X⁺ is a cationic moiety of coptisine, and m=1 and n=1. In certain preferred embodiments, U⁻ is an anionic moiety of obeticholic acid, X⁺ is a cationic moiety of palmatine, and m=1 and n=1. In certain preferred embodiments, U⁻ is an anionic moiety of obeticholic acid, X⁺ is a cationic moiety of jatrorrhizine, and m=1 and n=1. In certain preferred embodiments, the pharmaceutical composition further includes a compound selected from the group consisting of vitamin E, omega-3 fatty acids, S-adenosylmethionine, N-acetyl cysteine, silymarin, polyenylphosphatidylcholine, resveratrol or vitamin D. In certain preferred embodiments, treating, reducing, or preventing a disease or disorder is by normalizing liver enzyme levels of the subject.

Salts of Berberine or Derivatives

The invention further provides salts of berberine and organic acids, pharmaceutical compositions thereof, as well as related methods of their use in treating various diseases or disorders.

Salts of berberine includes those with organic acids such as -(+)-α-lipoic acid, hydroxycitric acid, eicosapentaenoic acid, docosahexaenoic acidursolic acid, corosolic acid, cinnamic acid, cholic acid, obeticholic acid, ursodeoxycholic acid, oleanolic acid, salicylic acid, betulinic acid, chlorogenic acid, caffeic acid, bassic acid, acetyl L-carnitine, S-allyl cysteine sulphoxide, S-methyl cysteine sulfoxide, pantothenic acid, ascorbic acid, retinoic acid, nicotinic acid, and biotin.

In yet another aspect, the invention generally relates to an acid-base addition salt in substantially pure form, having the formula of:

$$(B^+)_m(Y^-)_n \qquad (II)$$

wherein
(a) B⁺ is a cationic moiety of berberine or a derivative or analog thereof;
(b) Y⁻ is an anionic moiety of a pharmacologically active organic acid; and
(c) m and n are integers independently selected from 1, 2, 3, 4, 5 and 6 so as to arrive at a charge neutral salt.

In certain embodiments of the acid-base addition salt, the berberine derivative or analog is selected from Table 2.

In certain embodiments of the acid-base addition salt, the pharmacologically active organic acid is selected from the group consisting of -(+)-α-lipoic acid, hydroxycitric acid, eicosapentaenoic acid, docosahexaenoic acid, docosapentaenoic acid, ursolic acid, corosolic acid, cinnamic acid, cholic acid, obeticholic acid, ursodeoxycholic acid, oleanolic acid, salicylic acid, betulinic acid, chlorogenic acid, caffeic acid, bassic acid, acetyl L-carnitine, S-allyl cysteine sulphoxide, S-methyl cysteine sulfoxide, pantothenic acid, ascorbic acid, retinoic acid, nicotinic acid, biotin and other organic acid that is generally recognized pharmacologically active for one or more diseases or disorders selected from metabolic disorders, heart diseases, atherosclerosis, neurodegenerative diseases, liver diseases, sarcopenia, muscle atrophy, inflammation, and cancer, or a related disease or disorder thereof in a mammal, including a human by those of skill in the art.

In certain embodiments, B⁺ is a cationic moiety of berberine and Y⁻ is an anionic moiety of -(+)-α-lipoic acid, and m=1 and n=1.

In certain embodiments, B+ is a cationic moiety of berberine and Y⁻ is an anionic moiety of hydroxycitric acid, and m=1 and n=1, or m=2, n=1, or m=3, n=1.

In certain embodiments, B⁺ is a cationic moiety of berberine and Y⁻ is an anionic moiety of EPA, and m=1 and n=1.

In certain embodiments, B+ is a cationic moiety of berberine and Y⁻ is an anionic moiety of DHA, and m=1 and n=1.

In certain embodiments, B+ is a cationic moiety of berberine and Y⁻ is an anionic moiety of DPA, and m=1 and n=1.

In certain embodiments, B+ is a cationic moiety of berberine and Y⁻ is an anionic moiety of ursolic acid, and m=1 and n=1.

In certain embodiments, B+ is a cationic moiety of berberine and Y⁻ is an anionic moiety of corosolic acid, and m=1 and n=1.

In certain embodiments, B+ is a cationic moiety of berberine and Y⁻ is an anionic moiety of cholic acid, and m=1 and n=1.

In certain embodiments, B+ is a cationic moiety of berberine and Y⁻ is an anionic moiety of ursodeoxycholic acid, and m=1 and n=1.

In certain embodiments, B+ is a cationic moiety of berberine and Y⁻ is an anionic moiety of obeticholic acid, and m=1 and n=1.

In yet another aspect, the invention generally relates to a pharmaceutical composition comprising an amount of an acid-base addition salt having the formula of:

$$(B^+)_m(Y^-)_n \quad (II)$$

wherein
(a) B⁺ is a cationic moiety of berberine or a derivative or analog thereof;
(b) Y⁻ is an anionic moiety of a pharmacologically active organic acid; and
(c) m and n are integers independently selected from 1, 2, 3, 4, 5 and 6 so as to arrive at a charge neutral salt,
effective to treat, prevent, or reduce one or more diseases or disorders selected from metabolic disorders, heart diseases, atherosclerosis, neurodegenerative diseases, liver diseases, sarcopenia, muscle atrophy, inflammation, and cancer, or a related disease or disorder thereof in a mammal, including a human, and a pharmaceutically acceptable excipient, carrier, or diluent.

In certain embodiments, the disease or disorder is a metabolic disorder which is selected from diabetes, diabetic complications, dyslipidemia, diabetic dyslipidemia, dyslipidemia in statin-intolerance patients, hypercholesterolemia, hypertriglyceridemia, metabolic syndromes and pre-diabetes. In certain embodiments, the metabolic disorder is type 1 or type 2 diabetes.

In certain embodiments, the disease or disorder is cancer. In certain embodiments, the cancer is selected from the group consisting of breast cancer, prostate cancer, lung cancer, hepatocellular carcinoma, pancreatic cancer, gastric carcinoma, colorectal cancer, leukemia, multiple myeloma, melanoma and glioblastoma.

In certain embodiments, the disease or disorder is heart diseases.

In certain embodiments, the disease or disorder is atherosclerosis.

In certain embodiments, the disease or disorder is sarcopenia.

In certain embodiments, the disease or disorder is muscle atrophy. In certain embodiments, the disease or disorder is muscle atrophy which is selected from skeletal muscle atrophy.

In certain embodiments of the pharmaceutical composition, the berberine derivative or analog is selected from Table 2.

In certain embodiments of the pharmaceutical composition, the pharmacologically active organic acid is selected from the group consisting of -(+)-α-lipoic acid, hydroxycitric acid, eicosapentaenoic acid, docosahexaenoic acid, docosapentaenoic acid, ursolic acid, and corosolic acid, cinnamic acid, cholic acid, obeticholic acid, ursodeoxycholic acid, oleanolic acid, salicylic acid, betulinic acid, chlorogenic acid, caffeic acid, bassic acid, acetyl L-carnitine, S-allyl cysteine sulphoxide, S-methyl cysteine sulfoxide, pantothenic acid, ascorbic acid, retinoic acid, nicotinic acid, biotin and other organic acid that is generally recognized pharmacologically active for one or more diseases or disorders selected from metabolic disorders, heart diseases, atherosclerosis, neurodegenerative diseases, liver diseases, sarcopenia, muscle atrophy, inflammation, and cancer, or a related disease or disorder thereof in a mammal, including a human by those of skill in the art.

In certain embodiments, B⁺ is a cationic moiety of berberine and X⁻ is an anionic moiety of -(+)-α-Lipoic acid, and m=1 and n=1. In certain embodiments, B⁺ is a cationic moiety of berberine and X⁻ is an anionic moiety of hydroxycitric acid, and m=1 and n=1, or m=2, n=1, or m=3, n=1. In certain embodiments, B⁺ is a cationic moiety of berberine and X⁻ is an anionic moiety of EPA, and m=1 and n=1. In certain embodiments, B⁺ is a cationic moiety of berberine and X⁻ is an anionic moiety of DHA, and m=1 and n=1. In certain embodiments, B⁺ is a cationic moiety of berberine and X⁻ is an anionic moiety of DPA, and m=1 and n=1. In certain embodiments, B⁺ is a cationic moiety of berberine and X⁻ is an anionic moiety of ursolic acid, and m=1 and n=1.

In yet another aspect, the invention generally relates to a method for treating, reducing, or preventing a disease or disorder. The method includes administering to a subject in need thereof a pharmaceutical composition comprising an amount of an acid-base addition salt having the formula of:

$$(B^+)_m(Y^-)_n \quad (II)$$

wherein
(a) B⁺ is a cationic moiety of berberine or a derivative or analog thereof;
(b) Y⁻ is an anionic moiety of a pharmacologically active organic acid; and
(c) m and n are integers independently selected from 1, 2, 3, 4, 5 and 6 so as to arrive at a charge neutral salt,
effective to treat, prevent, or reduce one or more diseases or disorders selected from metabolic disorders, heart diseases, atherosclerosis, neurodegenerative diseases, liver diseases, sarcopenia, muscle atrophy, inflammation, and cancer, or a related disease or disorder thereof in a mammal, including a human, and a pharmaceutically acceptable excipient, carrier, or diluent In certain embodiments, the metabolic disorder is selected from diabetes, diabetic complications, dyslipidemia, diabetic dyslipidemia, dyslipidemia in statin-intolerant patients, obesity, metabolic syndromes, pre-diabetes, fatty liver, NAFLD, and NASH. In certain embodiments, the metabolic disorder is type 1 or type 2 diabetes.

In certain embodiments, the berberine derivative or analog is selected from Table 2.

In certain embodiments, the pharmacologically active organic acid is selected from the group consisting of -(+)-α-lipoic acid, hydroxycitric acid, eicosapentaenoic acid, docosahexaenoic acid, docosapentaenoic acid, ursolic acid, and corosolic acid, cinnamic acid, cholic acid, obeticholic acid, ursodeoxycholic acid, oleanolic acid, salicylic acid, betulinic acid, chlorogenic acid, caffeic acid, bassic acid, acetyl L-carnitine, S-allyl cysteine sulphoxide, S-methyl cysteine sulfoxide, pantothenic acid, ascorbic acid, retinoic acid, nicotinic acid, biotin and other organic acid that is generally recognized pharmacologically active for one or more diseases or disorders selected from metabolic disorders, heart diseases, atherosclerosis, neurodegenerative diseases, liver diseases, sarcopenia, muscle atrophy, inflammation, and cancer, or a related disease or disorder thereof in a mammal, including a human by those of skill in the art.

In certain embodiments of the method, B⁺ is a cationic moiety of berberine and Y⁻ is an anionic moiety of -(+)-α-lipoic acid, and m=1 and n=1, and the subject suffers from diabetes and diabetic complications.

In certain embodiments of the method, $B^+$ is a cationic moiety of berberine and $Y^-$ is an anionic moiety of hydroxycitric acid, and m=1 and n=1, or m=2, n=1, or m=3, n=1, and the subject suffers from diabetes and obesity.

In certain embodiments of the method, $B^+$ is a cationic moiety of berberine and $Y^-$ is an anionic moiety of EPA, and m=1 and n=1, and the subject suffers from diabetes and dyslipidemia, or heart diseases, atherosclerosis, or neurodegenerative diseases.

In certain embodiments of the method, $B^+$ is a cationic moiety of berberine and $Y^-$ is an anionic moiety of DHA, and m=1 and n=1, and the subject suffers from diabetes and dyslipidemia, or heart diseases, atherosclerosis, or neurodegenerative diseases.

In certain embodiments of the method, $B^+$ is a cationic moiety of berberine and $Y^-$ is an anionic moiety of DPA, and m=1 and n=1, and the subject suffers from diabetes and dyslipidemia, or heart diseases, atherosclerosis, or neurodegenerative diseases.

In certain embodiments of the method, $B^+$ is a cationic moiety of berberine and $Y^-$ is an anionic moiety of ursolic acid, and m=1 and n=1, and the subject suffers from diabetes and sarcopenia, or muscle atrophy.

In certain embodiments of the method, $B^+$ is a cationic moiety of berberine and $Y^-$ is an anionic moiety of corosolic acid, and m=1 and n=1, and the subject suffers from diabetes and sarcopenia, or muscle atrophy.

In certain embodiments of the method, $B^+$ is a cationic moiety of berberine and $Y^-$ is an anionic moiety of cholic acid, and m=1 and n=1, and the subject suffers from dyslipidemia, fatty liver, NAFLD or NASH.

In certain embodiments of the method, $B^+$ is a cationic moiety of berberine and $Y^-$ is an anionic moiety of obeticholic acid, and m=1 and n=1, and the subject suffers from dyslipidemia, fatty liver, NAFLD or NASH.

In certain embodiments of the method, $B^+$ is a cationic moiety of berberine and $Y^-$ is an anionic moiety of ursodeoxycholic acid, and m=1 and n=1, and the subject suffers from dyslipidemia, fatty liver, NAFLD or NASH.

In certain preferred embodiments of the method, treating, reducing, or preventing a metabolic disorder is by reducing blood glucose levels of the subject. In certain preferred embodiments of the method, treating, reducing, or preventing a metabolic disorder is by reducing total cholesterol (TC), triglyceride (TG) and low-density lipoprotein cholesterol (LDL-c) levels, increasing high-density lipoprotein cholesterol (HDL-c) levels of the subject. In certain preferred embodiments of the method, treating, reducing, or preventing a metabolic disorder is by normalizing liver enzyme levels of the subject. In certain preferred embodiments of the method, treating, reducing, or preventing a metabolic disorder is by normalizing liver lipid levels of the subject. In certain preferred embodiments of the method, treating, reducing, or preventing a metabolic disorder is by altering insulin signaling pathway such that glucose levels are reduced. In certain preferred embodiments of the method, treating, reducing, or preventing a metabolic disorder is by regulating multiple metabolic pathways such as increasing secretion of insulin, improving insulin sensitivity, reducing gluconeogenesis in liver, reducing glucose absorption, ameliorating dyslipidemia, anti-inflammation to achieve the desired pharmacological effects.

The following examples are meant to be illustrative of the practice of the invention, and not limiting in any way.

EXAMPLES

Example 1. Efficacy of the Combination of Berberine and Eicosapntemacnioc Acid (EPA), Docosahexaenoic Acid (DHA); or Berberine and Ursolic Acid (UA) in High Fat Diet Streptozocin Induced Diabetic Mice Model This example describes an in vivo efficacy study of the combinations disclosed in the present invention using a high fat diet (HFD) and streptozotocin (STZ) induced diabetic mice model.

Sixty NIH male mice of 4 weeks old were acquired from Guangzhou Institute of Laboratory Animal. After acclimatization for one week, five mice were selected as normal control group (Group 1), the rest fifty-five mice were administered single dose of STZ at the dose of 40 mg/kg, and fed with HFD (in which 40% of calories is from fat) for 7 days to establish a diabetic animal model resembling the pathophysiology of type 2 diabetes in human. Mice in the normal control group were not administered STZ, and fed with normal chow diet.

For the fifty-five mice induced with STZ and HFD, forty of them with fasting blood glucose greater than 12.0 mmol/L at the seventh day post of STZ administration were selected and randomized into 4 groups (n=10 per group):

Group 2: Vehicle control (Normal saline)

Group 3: Positive control (Metformin 300 mg/kg)

Group 4: Combination of berberine (150 mg/kg) and UA (150 mg/kg)

Group 5: Combination of berberine (150 mg/kg), EPA (75 mg/kg) and DHA (75 mg/kg)

The mice from Group 2 to 5 were treated with the corresponding testing articles indicated above once daily by intragastric gavage. HFD continued throughout the duration of the treatment of 28 days. The normal mice (Group 1) were treated with normal saline by intragastric gavage. Fasting blood glucose, total cholesterol (TC) and triglyceride (TG) levels, food intake, water intake and body weight were measured throughout the study.

On day 28 of the treatment, an oral glucose tolerance test (OGTT) was performed in 12-hour fasted animals. For the OGTT, after the measurement of the basal glucose concentration (T=−30 min), mice received an oral glucose challenge at 2.5 g/kg and glucose values were determined by glucometer (ACCU-CHEK Active, Roche) at 0, 30, 60 and 120 min.

After OGTT, blood samples were collected for the measurement of blood glucose, TC and TG. The mice were sacrificed, and the pancreas, liver, kidney and fat were harvested for histopathology analysis.

The experimental results were listed in Table 6 and Table 7.

TABLE 6

Average body weight, food intake and water intake in different treatment group*

| Group | Weight (g) Day 0 | Weight (g) Day 27 | Food Intake (g) Day 3 | Food Intake (g) Day 27 | Water intake (mL) Day 3 | Water intake (mL) Day 6 | Water intake (mL) Day 27 |
|---|---|---|---|---|---|---|---|
| No. 1 Normal | 27.80 ± 1.45 (n = 5) | 34.20 ± 2.84 (n = 5) | 3.69 (n = 5) | 4.88 (n = 5) | 7.60 (n = 5) | 8.40 (n = 5) | 7.20 (n = 5) |
| No. 2 Vehicle control | 27.20 ± 1.47 (n = 10) | 34.70 ± 3.32 (n = 10) | 7.46 (n = 10) | 13.78 (n = 10) | 19.20 (n = 10) | 24.40 (n = 10) | 32.00 (n = 10) |
| No. 3 Metformin | 26.30 ± 2.54 (n = 10) | 36.99 ± 3.90 (n = 10) | 8.66 (n = 10) | 9.37 (n = 10) | 19.40 (n = 10) | 23.60 (n = 10) | 34.40 (n = 10) |
| No. 4 Berberine + UA | 26.20 ± 1.77 (n = 10) | 26.13 ± 2.95 $(n = 8)^{a,b}$ | 9.08 (n = 10) | 6.59 $(n = 8)^e$ | 19.40 (n = 10) | 19.00 (n = 10) | 13.25 $(n = 8)^{a,b}$ |
| No. 5 Beberine + EPA/DHA | 25.90 ± 2.04 (n = 10) | 29.76 ± 4.89 $(n = 10)^{c,d}$ | 8.35 (n = 10) | 5.79 $(n = 10)^f$ | 19.40 (n = 10) | 20.00 (n = 10) | 14.20 $(n = 10)^{c,d}$ |

*1) Body weight was measured on day 0, and on day 27 the day prior to the sacrifice, to minimize the variations caused by 12-hour fasting.
2) Food intake and water intake were measured twice weekly throughout the study, representative data were presented here.
3) Two animals in Group 4 were found dead throughout the study. The autopsy results indicated inappropriate handling when dosing by intra-gavage.
$^{a,b}$significant difference between G4 and G2, G3 ($p < 0.001$)
$^{c,d}$significant difference between G5 and G2, G3 ($p < 0.01$)
$^e$significant difference between G4 and G2 ($p < 0.05$)
$^f$significant difference between G5 and G2 ($p < 0.01$)

TABLE 7

Average fasting blood glucose, total cholesterol and triglyceride in different treatment group

| Group | Fasting blood glucose (mmol/L) Day 0 | Fasting blood glucose (mmol/L) Day 28 | Total Cholesterol (mg/dL) Day 0 | Total Cholesterol (mg/dL) Day 28 | Triglyceride (mmol/L) Day 0 | Triglyceride (mmol/L) Day 28 |
|---|---|---|---|---|---|---|
| No. 1 Normal | 11.59 ± 1.12 (n = 5) | 3.84 ± 0.26 (n = 5) | 222.93 ± 16.17 (n = 5) | 234.63 ± 57.65 (n = 5) | 1.02 ± 0.31 (n = 5) | 1.94 ± 0.33 (n = 5) |
| No. 2 Vehicle control | 24.74 ± 8.47 (n = 10) | 24.58 ± 6.01 (n = 10) | 303.90 ± 65.51 (n = 10) | 335.49 ± 103.95 (n = 10) | 2.16 ± 0.78 (n = 10) | 4.99 ± 6.01 (n = 10) |
| No. 3 Metformin | 24.08 ± 5.44 (n = 10) | 21.66 ± 4.71 (n = 10) | 297.96 ± 67.09 (n = 10) | 436.99 ± 159.73 (n = 10) | 2.40 ± 1.03 (n = 10) | 6.06 ± 6.71 (n = 10) |
| No. 4 Berberine + UA | 23.78 ± 8.56 (n = 10) | 14.70 ± 7.22 $(n = 8)^a$ | 327.52 ± 55.60 (n = 10) | 264.30 ± 81.49 $(n = 8)^b$ | 2.15 ± 0.87 (n = 10) | 2.87 ± 1.28 $(n = 8)^d$ |
| No. 5 Beberine + EPA/DHA | 24.36 ± 7.43 (n = 10) | 18.20 ± 8.71 (n = 10) | 303.07 ± 47.27 (n = 10) | 242.39 ± 53.82 $(n = 10)^c$ | 2.56 ± 1.01 (n = 10) | 4.16 ± 3.66 (n = 10) |

$^a$significant difference between G4 and G2 ($p < 0.01$)
$^{b,c}$significant difference between G4, G5 and G3 ($p < 0.001$)
$^d$ significant difference between G4 and G3 ($p < 0.05$)

These results demonstrated that the combinations of berberine and EPA/DHA, and berberine and UA effectively ameliorated symptoms of diabetes HFD/STZ induced diabetic mice model. In contrast, although used at the suggested therapeutic dose, metformin, an oral anti-diabetic drug used as the first-line of choice for the treatment of type 2 diabetes did not demonstrate a clear efficacy in this study, further studies are being conducted to verify the observations made in this study.

Example 2. Synergistic Effects of the Combination of Berberine and Hydroxycitric Acid in a High Fat Diet Induced Obesity Mice Model This example describes an in vivo efficacy study of the combinations disclosed in the present invention using a high fat diet (HFD) induced obesity mice model.

Fifty NIH male mice of 4 weeks old were acquired (Guangzhou Institute of Laboratory Animal). After acclimatization for one week, eight mice were selected as normal control; the rest forty-two mice were fed with HFD (in which 40% of calories is from fat) for 14 days to establish a HFD induced obesity mice model resembling the pathophysiology of metabolic syndrome in human. Normal control mice were fed with normal chow diet. For the forty-two mice fed with HFD for 14 days, thirty-two of them with body weight 15-20% above the normal control mice were selected and randomized into 4 groups (n=8 per group):

Group 1: Vehicle control (1% Carboxymethyl Cellulose (CMC) solution)
Group 2: Berberine (50 mg/kg in 1% CMC solution)
Group 3: Hydroxycitric acid (50 mg/kg in 1% CMC solution)
Group 4: Combination (berberine (50 mg/kg), and hydroxycitric acid (50 mg/kg) in 1% CMC solution)

The mice from Group 1 to 4 were treated with the corresponding testing articles indicated above once daily by intragastric gavage. HFD continued throughout the duration of the treatment of 28 days. Blood glucose (fasting and non-fasting), total cholesterol (TC) and triglyceride (TG) levels, food intake, water intake and body weight were measured throughout the study.

On day 28 of the treatment, an oral glucose tolerance test (OGTT) was performed in 12-hour fasted animals. For the OGTT, after the measurement of the basal glucose concentration (T=−30 min), mice received an oral glucose challenge at 2.5 g/Kg and glucose values were determined by glucometer (ACCU-CHEK Active, Roche) at 0, 30, 60 and 120 min.

After OGTT, blood samples were collected for the measurement of blood glucose, TC and TG. The mice were sacrificed, and the pancreas, liver, kidney and fat were harvested for histopathology analysis.

The study has been carried out for 15 days, and the interim experimental results were presented in FIGS. 1-4.

These results demonstrated that the trend of synergistic effects of the berberine and hydroxycitric acid combination. In particular, when using individually at the dose of 50 mg/Kg, neither berberine (Group 2), nor hydroxycitric acid (Group 3) demonstrated any pharmacological effects comparing to the vehicle control group (Group 1); however, when using together (Group 4), reduction in the body weight gain and normalization of the blood glucose level were observed. Additional data will be collected upon the completion of the study.

Example 3. Synthesis and Analysis of Metformin Ursodeoxycholate Salt 5 mmol metformin hydrochloride was dissolved in NaOH aqueous solution and allowed to react at room temperature until a clear colorless solution was obtained. The solvent was evaporated to yield a white powder. The white powder was added into absolute ethanol and then the obtained suspension was filtered to remove white precipitate (NaCl). The filtrate was rotary evaporated and then dried in vacuo to yield a white powder of Met-OH. The Met-OH was dissolved in absolute ethanol and was reacted with UDCA at room temperature to yield a clear, light yellow solution. The solution was rotary evaporated and the residue dried under vacuum (room temp). The resulting white powder was then characterized with $^1$H NMR and IR (FIGS. 5-6), which indicated the formation of metformin ursodeoxycholate salt with 1:1 stoichiometry of Met:UDCA.

Example 4. Synthesis and Analysis of Berberine Ursodeoxycholate Salt

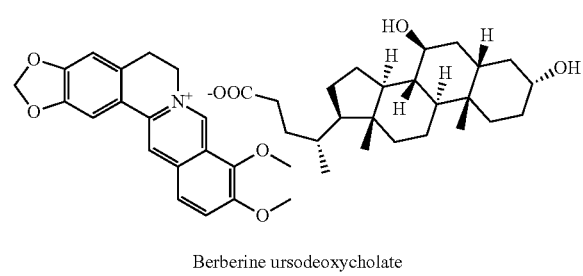

Berberine ursodeoxycholate

BBR-Cl (1.0 eq) was dissolved into hot distilled water and then the reaction mixture was cooled to room temperature. At the same time, ursodeoxycholic acid (0.9-1.5 eq.) was dissolved into anhydrous ethanol, The aqueous solution of $NaCO_3$ (0.9-1.5 eq) was added drop wise into the obtained ethanol solution of ursodeoxycholic acid. Then the resulting reaction mixture was stirred for 15-45 minutes and an ursodeoxycholic acid sodium salt solution was obtained.

The BBR-Cl solution was added drop wise to the above ursodeoxycholic acid sodium salt solution under 60-80° C. The mixture was allowed to stir at the same temperature for 2 hours, and then was cooled to room temperature. The precipitated solid was filtered and the wet cake was collected and dried under vacuum below a temperature of 40° C. to produce crude berberine ursodeoxycholate.

Crude berberine ursodeoxycholate was purified through crystallization with ethanol and ethyl acetate. The mixture was allowed to stir for 7-8 hours, and then was centrifuged to remove solvent and collect yellow powder. The yellow powder was rinsed with ethyl acetate again and repeated the above procedures twice. The final resulted yellow powder was dried under vacuum at a temperature of 40° C. to obtain purified berberine ursodeoxycholate.

The resulting yellow powder was then characterized with $^1$H-NMR, IR, and MS (FIG. 7-12). From the $^1$H-NMR (FIG. 7-8) and IR (FIG. 9-10) clear distinctions between the simple mixture of berberine and UDCA (1:1) versus berberine ursodeoxycholate can be seen which indicated the formation of berberine ursodeoxycholate salt with 1:1 stoichiometry of BBR:UDCA. The MS spectra (FIG. 11-12) indicated that in negative MS mode, molecular mass of UDCA $[M-H]^-$ 391.28 was identified. And in positive MS mode, molecular mass of $BBR^+$ 336.14 was identified.

An alternate synthetic method exploits the high EtOH solubility of berberine ursodeoxycholate coupled with the solubility of BBR in MeOH and the solubility of UDCA sodium in EtOH. For example:

1) Dissolve BBR (1.5 eq) in MeOH at RT. (Solution A)
2) Dissolve UDCA (0.9-1.5 eq) in EtOH at RT, add sodium ethoxide solution (Solution B)
3) Add Solution A to Solution B at RT and stir for 2-5 hrs. Remove NaCl by vacuum filtration, and concentrate filtrate (T<40° C.).
4) Purify crude berberine ursodeoxycholate by dissolving the crude product in EtOH (or other suitable solvent) and removing residual NaCl by filtration. Alternately, it may be possible to purify the crude product by "crystallization" from a suitable solvent.

Example 5. Efficacy of Berberine Ursodeoxycholate (BUDCA) in High Fat Diet Induced Non-Alcoholic Fatty Liver Mice Model This example describes an in vivo efficacy study of BUDCA disclosed in the present invention using a high fat diet (HFD) induced non-alcoholic fatty liver mice model.

91 NIH male mice of 4 weeks old were obtained from Vital River Laboratories (Beijing, China). After acclimatization for one week, 13 mice were selected as control group (Group 1, G1) with normal chow diet fed, and the other 78 mice were fed with HFD (in which 40% of calories is from fat) for 4 weeks to establish an animal model resembling the pathophysiology of non-alcoholic fatty liver in human.

Following 4 weeks of high fat dietary intervention, the 78 mice were divided into 6 groups according to body weight (n=13 per group):

Group 2, G2: Vehicle control (0.5% CMC-Na solution)
Group 3, G3: Low-dose group of BUDCA (30 mg/kg)
Group 4, G4: Middle-dose group of BUDCA (100 mg/kg)
Group 5, G5: High-dose group of BUDCA (300 mg/kg)
Group 6, G6: BBR control group (Berberine HCl, 150 mg/Kg)
Group 7, G7: UDCA control group (Ursodeoxycholic acid, 150 mg/Kg)

The mice from G2 to G7 were administered with the corresponding testing articles indicated above once daily by intragastric gavage. HFD continued throughout the duration of the treatment of 6 weeks. The normal mice (G1) were treated with vehicle (0.5% CMC-Na solution) via intragastric gavage. At the end of experiment, the following biochemical parameters were measured and tests were carried out:

Body weight, the weight ratio of liver
Total cholesterol (TC) and triglyceride (TG) levels, high density lipoprotein cholesterol (HDL-C) and low density lipoprotein cholesterol (LDL-C) levels
Alanine aminotransferase (ALT) and aspartate aminotransferase (AST) levels
Superoxide dismutase (SOD) activity and malondialdehyde (MDA) level
Oral glucose tolerance test (OGTT)
Histopathological examination of liver (Sultan III staining)

After 6 weeks treatment, blood was collected via retro-orbital bleeding of each 12-hour fasted animal. Liver was harvested by surgery for histopathology analysis after weight measurement. Then the serum was isolated for the determination of TC, TG, HDL-C, LDL-C, ALT, AST, SOD and MD A.

One week before sacrifice (Week 5 of treatment), an oral glucose tolerance test (OGTT) was performed in 12-hour fasted animals. For the OGTT, all mice received an oral glucose challenge at 2.0 g/Kg and the blood glucose concentrations were determined by glucometer (ACCU-CHEK Active, Roche) at 0, 30, 60, 90 and 120 min.

The liver tissue was histopathologically evaluated by Sultan III staining after frozen section.

The experimental results were listed as following.

TABLE 8

Body weight and biochemical parameters in various groups

| GROUP | Body weight (g) | Weight ratio of liver (%) | TC (mmol/L) | TG (mmol/L) | HDL-C (mmol/L) | LDL-C (mmol/L) |
|---|---|---|---|---|---|---|
| G1 | 42.6 ± 0.82 | 3.77 ± 0.12 | 4.76 ± 0.18 | 0.75 ± 0.07 | 2.74 ± 0.11 | 0.61 ± 0.05 |
| G2 | 45.7 ± 0.68** | 4.41 ± 0.15** | 7.60 ± 0.76** | 2.03 ± 0.19** | 2.65 ± 0.26 | 1.79 ± 0.24** |
| G3 | 40.3 ± 1.18## | 4.33 ± 0.13 | 5.49 ± 0.25# | 1.18 ± 0.20## | 2.33 ± 0.15 | 1.05 ± 0.09## |
| G4 | 41.7 ± 1.59# | 4.15 ± 0.09 | 5.28 ± 0.50# | 0.92 ± 0.06## | 2.26 ± 0.22 | 1.06 ± 0.11# |
| G5 | 41.5 ± 1.16## | 4.27 ± 0.10 | 5.95 ± 0.54 | 0.85 ± 0.06## | 2.48 ± 0.15 | 1.03 ± 0.22# |
| G6 | 42.4 ± 1.37# | 4.26 ± 0.12 | 5.97 ± 0.47 | 1.00 ± 0.08## | 2.47 ± 0.20 | 1.42 ± 0.21 |
| G7 | 42.0 ± 1.16# | 4.77 ± 0.26 | 4.77 ± 0.70# | 1.20 ± 0.22# | 2.13 ± 0.33 | 1.37 ± 0.26 |

Data are expressed as the mean ± S.E.M (n = 7~13).
*p < 0.05,
**p < 0.01 G2 vs. G1
p < 0.05,
p < 0.01 G3, G4, G5, G6, or G7 vs. G2

TABLE 9

Liver function in various groups

| GROUP | ALT (U/L) | AST (U/L) |
|---|---|---|
| G1 | 32.7 ± 2.88 | 154.6 ± 10.01 |
| G2 | 37.4 ± 7.28 | 250.4 ± 36.73* |
| G3 | 30.6 ± 4.37 | 148.3 ± 7.15# |
| G4 | 29.0 ± 3.95 | 140.2 ± 16.32# |
| G5 | 27.8 ± 3.08 | 163.5 ± 11.63# |
| G6 | 37.1 ± 4.08 | 198.7 ± 18.93 |
| G7 | 30.6 ± 5.73 | 162.86 ± 29.42 |

Data are expressed as the mean ± S.E.M (n = 7~13).
*p < 0.05 G2 vs. G1
p < 0.05 G3, G4, or G5 vs. G2

TABLE 10

Oxidative stress index in various groups

| GROUP | SOD (U/mL) | MDA (mmol/L) |
|---|---|---|
| G1 | 84.53 ± 5.64 | 5.67 ± 0.70 |
| G2 | 38.23 ± 11.61** | 24.11 ± 6.50** |
| G3 | 61.05 ± 11.59 | 12.34 ± 2.89 |
| G4 | 91.83 ± 4.90## | 8.02 ± 1.08# |
| G5 | 97.54 ± 4.88## | 7.78 ± 1.66# |
| G6 | 77.03 ± 8.98# | 9.30 ± 2.14# |
| G7 | 44.75 ± 11.99 | 18.94 ± 4.42 |

Data are expressed as the mean ± S.E.M (n = 7~13).
**p < 0.01 G2 vs. G1
p < 0.05,
p < 0.01 G4, G5, or G6 vs. G2

These results demonstrated that the ionic compound berberine ursodeoxycholate dose-dependently ameliorated symptoms of non-alcoholic fatty liver in the mice model induced by HFD. In contrast, although used at the typically suggested therapeutic dose, berberine or ursodeoxycholic acid monotherapy was not as effective as berberine ursodeoxycholate. It was also noted that, at the time of sacrifice, no gastrointestinal side effects were observed in berberine ursodeoxycholate treated animals, whereas 50% of animals in the berberine treatment group showed gastrointestinal side effects.

Example 6. Efficacy of BUDCA in High Fat Diet-Induced Fatty Liver Golden Hamster Model This example describes an in vivo efficacy study of BUDCA salt disclosed in the present invention using a high fat diet (HFD) induced fatty liver golden hamster model.

Forty-two SPF golden hamsters with the body weight of 90-100 g were acquired from Vital River Laboratory Animal Technology Co., Ltd. After acclimatization for one week, eight hamsters were selected as normal control group (Group 1), which were fed with normal chow diet. The rest thirty-four hamsters were fed with HFD for two weeks to establish a fatty liver animal model resembling the pathophysiology of NAFLD in human.

For the thirty-four hamsters induced with HFD, twenty-four of them with TC level of 17.96±1.70 mmol/L at the fourteenth day post of HFD were selected and randomized into three groups (n=8 per group):

Group 2: Model control (0.5% tragacanth solution 10 ml/kg);

Group 3: Low-dose (BUDCA 50 mg/kg);
Group 4: High-dose (BUDCA 200 mg/kg)

The hamsters from Group 2 to 4 were treated with corresponding testing articles indicated above once a day by intragastric gavage, and HFD continued throughout the duration of the 7-week administration. The normal hamsters in Group 1 were treated with 0.5% tragacanth solution (10 ml/kg) by intragastric gavage. Serum lipid and blood glucose level, liver function index, food intake and body weight were measured throughout the study. After the 7-week administration, the hamsters were sacrificed and dissected for the general observation and histopathological analysis of liver tissue. The experimental results were shown as following:

Food Intake and Body Weight: There is no significant difference on food intake between the model control group and the medicated groups (P>0.05). The body weight of the high-dose group significantly reduced in the first week of treatment (P<0.05) and no significant changes were observed in the rest time of treatment (P>0.05). No significant changes were observed in the body weight of the low-dose group throughout the study (P>0.05).

Serum Lipid and Blood Glucose Level: In the model control group, the TC level, TG level, LDL-c level, value of TC/HDL-c and arterial stiffness index (AI) were increased significantly comparing with those of the normal control group (P<0.01), and the compensatory rising of HDL-c level was observed significantly too (P<0.01) while there was no significant difference in blood glucose level between the model control group and the normal control group (P>0.05). Comparing with the model control group, the TC level of both low-dose group and high-dose group were significantly declined (P<0.01), and the decreasing amplitude in high-dose group was greater than that in low-dose group (Table 11).

TABLE 11

The Effect of BUDCA on Serum TC Level of Hyperlipidemic Hamsters (mmol · $L^{-1}$, X ± s, n = 8)

| Group | Dosage | Serum TC level on Day 0 | Treatment Period | | | |
|---|---|---|---|---|---|---|
| | | | Week 1 | Week 3 | Week 5 | Week 7 |
| Group 1 | 10 ml · $kg^{-1}$ 0.5% tragacanth solution | 4.17 ± 0.30 | 3.03 ± 0.94 | 4.14 ± 0.32 | 4.21 ± 0.34 | 4.05 ± 0.33 |
| Group 2 | 10 ml · $kg^{-1}$, 0.5% tragacanth solution | 17.56 ± 2.59ΔΔ | 15.98 ± 2.93ΔΔ | 14.21 ± 4.56ΔΔ | 17.01 ± 4.65ΔΔ | 21.74 ± 6.44ΔΔ |
| Group 3 | 50 mg · $kg^{-1}$ BUDCA | 18.14 ± 1.13 | 9.33 ± 1.52** | 7.58 ± 2.01** | 10.50 ± 2.89** | 9.78 ± 2.58** |
| Group 4 | 200 mg · $kg^{-1}$ BUDCA | 18.18 ± 1.10 | 7.51 ± 0.71** | 6.75 ± 1.00** | 5.38 ± 1.24** | 4.95 ± 0.84** |

Note:
Comparing with the normal control group,
Δ = P < 0.05,
ΔΔ = P < 0.01;
Comparing with the model control group,
* = P < 0.05,
** = P < 0.01.

Comparing with the model control group, the TG level of low-dose group in Week 1 and the TG level of high-dose group in Week 1 and Week 7 were significantly declined (P<0.01), and the decreasing amplitude in high-dose group was greater than that in low-dose group too (Table 12).

TABLE 12

The Effect of BUDCA on Serum TG Level of Hyperlipidemic Hamsters (mmol · $L^{-1}$, X ± s, n = 8)

| Group | Dosage | Serum TG level on Day 0 | Treatment Period | | | |
|---|---|---|---|---|---|---|
| | | | Week 1 | Week 3 | Week 5 | Week 7 |
| Group 1 | 10 ml · $kg^{-1}$ 0.5% tragacanth solution | 2.21 ± 0.27 | 2.04 ± 0.85 | 1.13 ± 0.27 | 1.47 ± 0.47 | 1.07 ± 0.20 |
| Group 2 | 10 ml · $kg^{-1}$, 0.5% tragacanth solution | 5.87 ± 1.38ΔΔ | 5.77 ± 1.17ΔΔ | 2.74 ± 0.94Δ | 3.98 ± 1.35ΔΔ | 4.79 ± 2.21ΔΔ |
| Group 3 | 50 mg · $kg^{-1}$ BUDCA | 5.97 ± 1.19 | 3.60 ± 0.78** | 2.98 ± 1.31 | 4.51 ± 3.10 | 3.88 ± 1.21 |
| Group 4 | 200 mg · $kg^{-1}$ BUDCA | 6.31 ± 1.75 | 3.00 ± 0.67** | 2.68 ± 1.09 | 3.04 ± 1.68 | 1.90 ± 0.66** |

Note:
Comparing with the normal control group,
Δ = P < 0.05,
ΔΔ = P < 0.01;
Comparing with the model control group,
* = P < 0.05,
** = P < 0.01

Comparing with the model control group, the serum LDL-c level, the value of TC/HDL-c and the AI value of both high-dose group and low-dose group were significantly decreased (P<0.01), and the HDL-c level of high-dose group was significantly declined too (P<0.01). Moreover, the serum LDL-c level, value of TC/HDL-c and AI value of high-dose group were very similar to those of normal control group after 7-week administration (FIG. 16).

Liver Function Index: In the model control group, the serum AST and ALT level were significantly risen comparing with those of the normal control group (P<0.01), and the serum ALP had a trend of increasing too (P>0.05). Comparing with the model control group, the AST level was significantly declined (P<0.01) in both medicated groups after 7-week administration (FIG. 17). Comparing with the model control group, the ALT level was significantly declined (P<0.01) in both medicated groups after 7-week administration (FIG. 18).

General Observation of Liver Tissue, Liver Index and Fat Index: In the model control group, it was observed that the liver volume of the hamsters increased obviously and the liver surface was greasy. The color of the livers was also abnormal, which was grayish yellow or grayish white. The liver shape became blunt. The lipid deposition could be clearly observed. Moreover, both the liver weight and liver index significantly increased (P<0.01).

Comparing with the model control group, there was no significant change observed in the body weight of either low-dose group or high-dose group (P>0.05). However, the liver weight of both the medicated groups significantly decreased (P<0.01). The detailed results were shown in FIG. 19.

Comparing with the model control group, the color of livers was improved in both medicated groups. Especially in high-dose group the color of livers was ruddy, which was similar to the case of normal control group. The detailed results were shown in FIG. 20.

Based on the results of pathological observation, the content of TC and TG in liver, the inflammation score of liver tissue and the positive area for oil red significantly increased in the model control group comparing with those of the normal control group (P<0.01). Comparing with the model control group, the content of TC and TG, the inflammation score of liver tissue and the positive area for oil red significantly decreased in both medicated group (P<0.01). The detailed results were shown in FIG. 21-22.

Above experimental results indicated that BUDCA could significantly decrease the level of TG, TC, LDL-c in serum, and could reduce the TC/HDL-c and the ambulatory arterial stiffness index (AI). It could reduce the risk of atherosclerosis. It could significantly reduce the fatty deposits and improve the inflammation in liver. The effects of BUDCA were relatively dose-dependent. And BUDCA would be a potential candidate to be applied in the treatment or prevention of NAFLD/NASH and hyperlipidemia.

Example 7. Synthesis Schemes of Exemplary Berberine Salts (1) Berberine-(+)-α-Lipoic Acid Salt

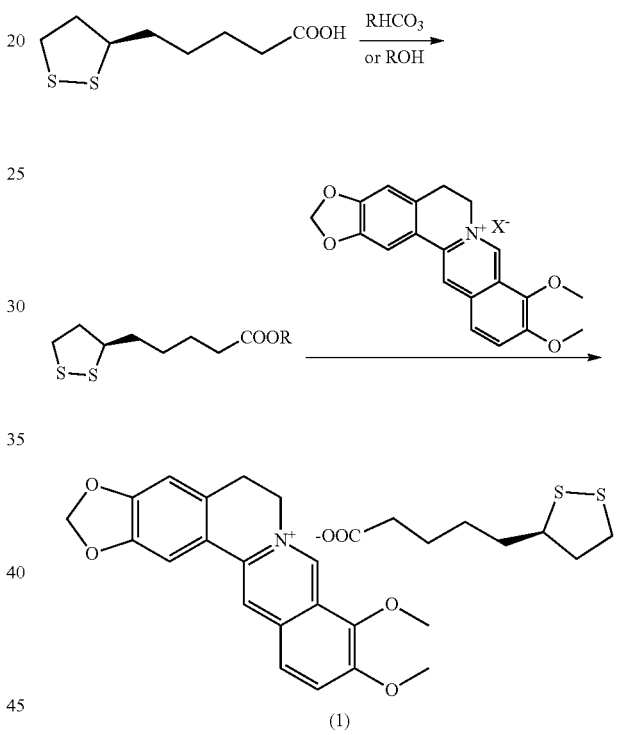

(2) Berberine Ursolic Acid Salt

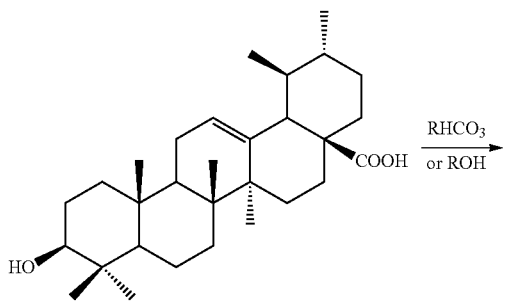

-continued
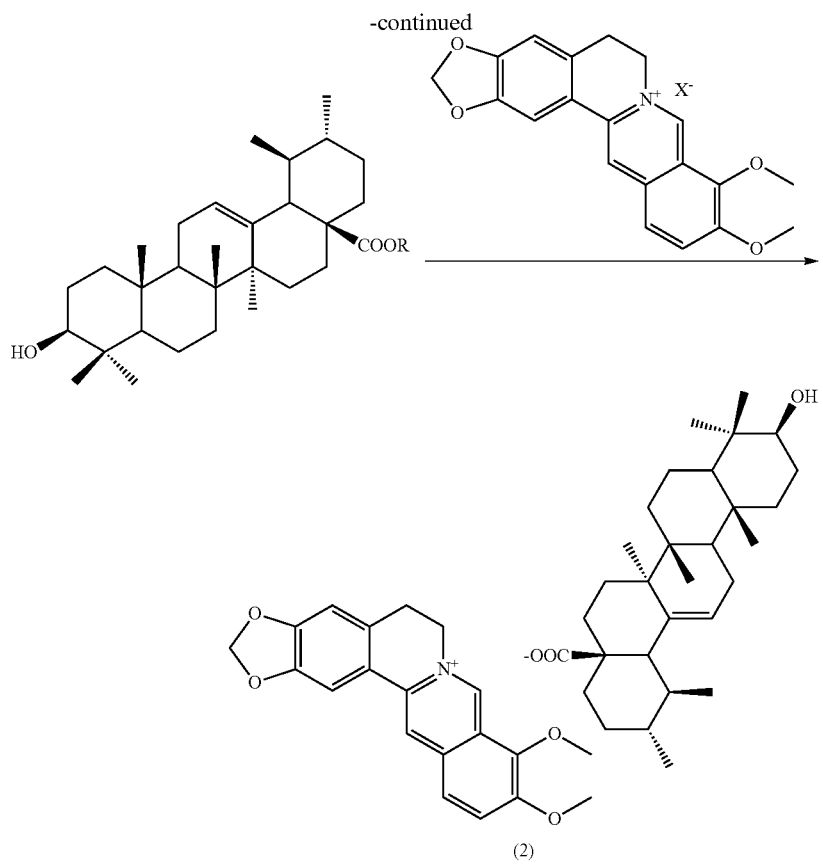
R: Na, K
X⁻: Cl, SO₄
R = Na, K
X⁻ = Cl⁻, HSO₄⁻
(3) Berberine Hydroxycitric Acid Salt (m=1, n=1)
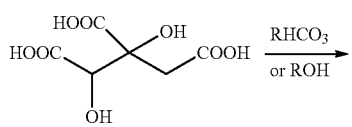
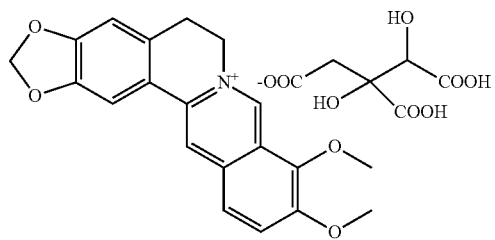
R = Na, K
X⁻ = Cl⁻, HSO₄⁻
(4) Berberine EPA Salt
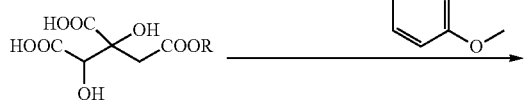
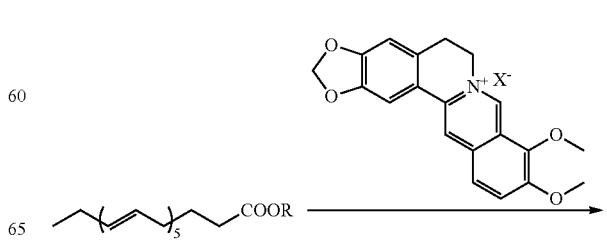

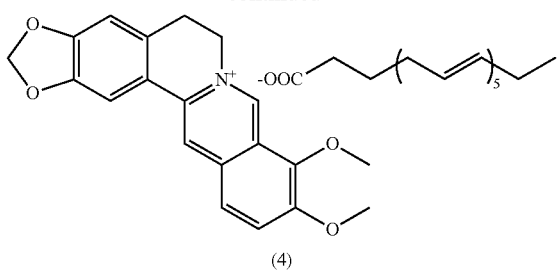

(4)

R = Na, K
X⁻ = Cl⁻, HSO₄⁻

(5) Berberine DHA Salt

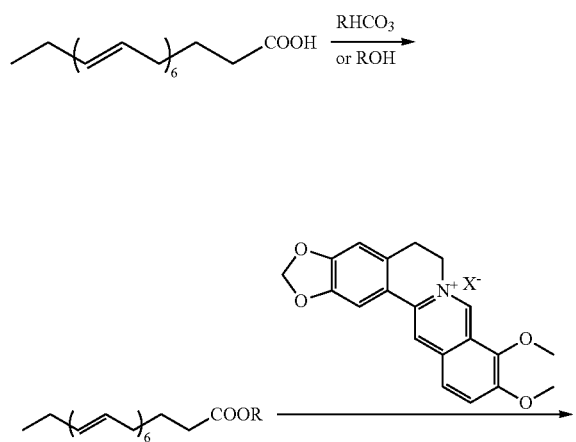

(5)

R = Na, K
X⁻ = Cl⁻, HSO₄⁻

(6) Preparation of Berberine Ursolic Salt

A solution of ursolic acid (0.9-1.5 eq.) in methanol was treated with a solution of sodium bicarbonate (0.9-1.5 eq.) in water. The solution was stirred for 30 minutes at room temperature, and then added dropwise to a solution of berberine chloride (1.0 eq.) in water. A yellow solid precipitated immediately upon the addition. The mixture was stirred for 1 hour, and then cooled to room temperature. A yellow solid was obtained by filtration with the yield of 30% (NMR is shown in FIG. 15).

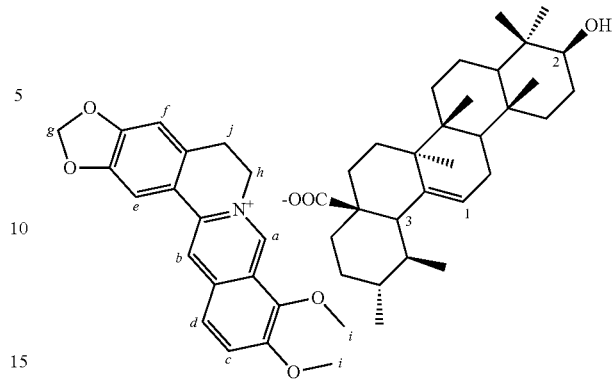

Example 8. Animal Models to Determine the Pharmacological Effects of Berberine Salts (1) Testing for Anti-Diabetes Activities Healthy male Sprague-Dawley rats, 8 weeks of age, were placed in a room with controlled lighting (12 hours light/dark cycle) and regulated temperature (18° C.-25° C.) and humidity. All rats were fed with regular chow (protein 21%, carbohydrate 55%, fat 6%, and total energy 15.36 KJ/g) for 1 week to be adapted for the environment. Six rats were randomly selected as normal control group (NC), which were fed regular chow diet throughout the study. The remaining rats were fed with high-fat diet (protein 16%, carbohydrate 38%, fat 46%, and total energy 20.54 KJ/g). After high-fat diet feeding for 8 weeks, diabetes was induced by a single intraperitoneal injection of freshly prepared streptozotocin (STZ, 30 or 50 mg/Kg body weight) (Sigma, St. Louis, Mo., USA) in citrate buffer (pH 4.5) to overnight fasted rats. After 2 wks of STZ administration, animals with fasting blood glucose levels >11.1 mM were selected for the study, and randomized in the following groups: vehicle (water), low dose, mid dose and high dose of berberine salts respectively by intragastric administration once daily for 28 consecutive days. The fasting glucose, insulin, total cholesterol, LDL-c, HDL-c and triglycerides levels of all animals were recorded on the day before first dosing (day 0) and day 7, 14, 21 and 28 days of dosing.

(2) Testing for Anti-Diabetic Complication (Diabetic Nephropathy) Activities

Five-week-old male Sprague-Dawley rats, weighing 120 to 130 g, were kept in wire-bottomed cages and exposed to a 12/12-h light/dark cycle. The room temperature was maintained at approximately 25° C. with relative constant humidity. They were allowed free access to regular laboratory pellet chow and water. After 1 week of adaptation, the rats underwent resection of one-half of the left kidney first, following by total excision of the right kidney 10 days after. Thereafter, they were injected intraperitoneally with STZ (25 mg/Kg body weight) in citrate buffer, pH 4.5. The blood glucose and urea nitrogen levels were determined after recovery from the injection, and the rats were divided into four groups (a control and three treatment groups), avoiding any intergroup differences in these blood indices. A normal group of rats that underwent sham operation was also included. Each experimental group contained 10 rats. Whereas the 50-day experiment was performed, the normal and control groups received water. The other three groups received berberine salts at low, mid and high dose via intragastric gavage respectively. At the end of this experiment, 24-h urine samples were collected using metabolic cages, and blood samples were obtained via cardiac puncture. The serum was immediately separated from the blood samples by centrifugation. After renal perfusion through the renal artery with ice-cold physiological saline, the remaining kidney was removed from each rat, and one part of the tissue was immersed in formalin for histological examination. The other part was frozen at −80° C. until analysis. Serum levels of glucose, total protein, albumin, total cholesterol, triglyceride, urea nitrogen, and creatinine were examined using commercial reagents.

(3) Testing for Anti-Dyslipidemia and/or Anti-Obesity Activities

The diet induced obesity (DIO) mice were established with feeding a high-fat diet (40 Kcal % fat) from 4 weeks of age of healthy NIH mice. Mice were housed three per group in polycarbonate cages maintained at normal temperature (22±4° C.) with normal humidity and exposed to 12/12-h light/dark cycle. After high-fat diet for 2 weeks, mice were weighed and randomized into groups of 10 mice each: control groups, low, mid and high dose of berberine salt by intragastric gavage once daily for a total of 4 weeks with the high-fat diet throughout the treatment. And six normal mice were included as normal group with regular chow diet. The food and water intake, body weight and non-fasting glucose were tested for all animals on the day before first dosing (day 0) and dosing of day 7, 14, 21 and 28. The 6-h fasting glucose, insulin, total cholesterol, LDL-c, HDL-c, triglyceride were tested for all animals on the day before first dosing (day 0) and dosing of day 28. The oral glucose tolerance test (OGTT) was test after 12-h fasting on day 28. After OGTT test, all animals were sacrificed and the pancreas, liver, kidney, and fat were weighed and collected for histology analysis.

(4) Testing for Efficacy in Skeletal Muscle Atrophy Model

Thirty-two male Sprague-Dawley rats (age 8 weeks) were housed individually at 25±1° C. with light from 8:00-20:00 and free access to water and regular commercial rat chow. After 1 week of acclimatization, rats were randomized into 4 groups. The control group (n=8) was injected with 2 mL/Kg/day of saline and the other three groups were injected with 2 mg/Kg/day prednisolone, a glucocorticoid purchased from SIGMA-Aldrich (MO, USA). The three glucocorticoid-injected groups were treated with water, low dose or high dose of berberine salts via intragastric gavage respectively (n=8 per group) for a total of 4 weeks. The food and water intake, body weight and glucose were tested for all animals on the day before first dosing (day 0) and dosing of day 7, 14, 21 and 28. At the end of the experiment, the rats were sacrificed by decapitation after overnight fasting. Blood was collected and centrifuged at 3000 rpm for 15 min to obtain serum. The serum was stored at −20° C. The liver, heart and skeletal muscles (soleus, plantaris, gastrocumemius, tibialis anterior and extensor digitorum longus) were quickly removed, weighed and stored at −80° C. until the analysis was performed.

(5) Testing for Efficacy in Attenuating NAFLD

Sixty-six healthy female Sprague-Dawley rats were randomized into two groups: high fat diet group (n=56, fed with high-fat diet) and normal group (n=10, fed with regular diet). At the end of 12th week, 6 rats from the high-fat diet group were randomly selected for hepatic histopathology examination and NAFLD rat model was confirmed to be successfully established. The remaining 50 model rats were subdivided into 5 equal subgroups: low, mid and high dose of berberine salts via intragastric gavage, vehicle control group and recovery group. Rats in vehicle control group were fed with water by gavage. 20 weeks later, all rats were anesthetized by 3% pentobarbital sodium through intraperitoneal injection. Plasma insulin and TG, TC, LDL-c, AST and ALT content in serum were determined. Upon sacrifice, liver tissues were harvested for histopathology examination.

(6) Testing for Efficacy in Attenuating NASH

Male Sprague-Dawley rats, weighing 160-170 g and six weeks of age were used in this study. They were housed in a temperature-controlled room (22±1° C.) with normal humidity and a 12 h light/dark cycle.

The rats were fed either standard chow (control group, n=8) or choline-deficient high-fat (CDHF) diets through the experiment period of 10 weeks. Fatty liver was induced by the feeding CDHF for 4 weeks. In the fifth week, rats on CDHF were randomized into six groups. The CDHF group (n=8) was fed CDHF diet only; the NASH group (n=8) rats were fed with CDHF diet, followed by i.p. injections of sodium nitrite ($NaNO_2$), an oxidant, 50 mg/Kg/day (Nacalai Tesque Inc., Kyoto, Japan) daily to induce methemoglobinemia (intermittent hypoxia stress) starting from the 5th week of CDHF for 6 weeks; NASH plus low, mid, and high dose of berberine salts (n=8 per group) via intragastric gavage concurrently during the period of nitrite injection.

At the end of the 10-week experimental period, animals were sacrificed by anesthetizing with diethyl ether. Blood samples were collected by vena cava inferior puncture with syringe containing heparin, and whole body perfusion was performed to left ventricular with 0.1 M potassium containing 5 mM benzamidine before obtaining tissue samples. Plasma was obtained by centrifugation at 1,000×g for 10 min at 4° C., and used for biochemical analysis. Plasma alanine aminotransferase (ALT) and aspartate aminotransferase (AST) were determined with commercial kits.

Fresh liver was used for liver fractionation and for observation of lipid peroxidation, and a portion for histopathological observation was immersed in 10% formalin for 3 days and then embedded in paraffin. And rest of liver was flash frozen by liquid nitrogen, stored in −80° C. for further analysis.

(7) Testing for Anti-Atherosclerosis Activities

The Atherosclerosis (AS) mice are established with feeding a composition of 15% lard, 4.5% cholesterol diet from 4 weeks of age of healthy C57/BL 6J mice. Mice are housed three per group in polycarbonate cages maintained at normal temperature (22±4° C.) with normal humidity and exposed to 12/12-h light/dark cycle.

After high-fat diet for 16 weeks, the histopathology of heart of 3-5 mice from the model group is conducted to evaluate the model establishment. The atherosclerotic lesions in predisposed cholesterol-fed mice are most pronounced in the ascending aorta at the attachment of aortic valves to the sinus wall. In the control animals, there is a single layer of endothelial cell overlying a thin layer of connective tissue and elastic. No lipid droplets are seen. The model mice are weighed and randomized into groups of 10 mice each: control groups, low, mid and high dose of berberine salt by intragastric gavage once daily for a total of 8 weeks with the high-fat diet throughout the treatment. And six normal mice are included as normal group with regular chow diet. The food and water intake and body weight are tested for all animals on the day before first dosing (day 0) and dosing of day 14, 28, 42 and 56. The total cholesterol, LDL-c, HDL-c, triglyceride are tested for all animals on the day before first dosing (day 0) and dosing of day 56. The all animals are sacrificed and the aorta, heart, liver, and fat are weighed and collected for histology analysis.

(8) Testing for Heart Failure Treatment

The efficacy of berberine salt for heart failure is evaluated with a rat model of dilated cardiomyopathy induced by Adriamycin. Adriamycin is injected into male Wistar rats by intraperitoneal at the dose of 2 mg/Kg per 3 days for 5 times, then at a dose of 2 mg/Kg per 7 days for 5 times to establish the heart failure model. Vehicle model group are injected with 0.9% saline using same methods. Rats are housed three per group in polycarbonate cages maintained at normal temperature (22±4° C.) with normal humidity and exposed to 12/12-h light/dark cycle with regular feed. Four rats are randomly picked up to evaluate the heart function with transthoracic echocardiography and myocardium morphology with electronmicroscope at the end of week 10. The parameters of LV end diastolic diameter (LVEDD) and LV end systolic diameter (LVESD), LV ejection fraction (EF) and LV faction shortening (FS) are shown that the heart failure of dilated cardiomyopathy type is established.

The rats are weighed and randomized into groups of 6 rats each: control groups, low, mid and high dose of berberine salt by intragastric gavage once daily for a total of 8 weeks treatment. And six vehicle model rats are included as normal group. The food and water intake and body weight are tested for all animals on the day before first dosing (day 0) and dosing of day 14, 28, 42 and 56. The parameters of LV end diastolic diameter (LVEDD) and LV end systolic diameter (LVESD), LV ejection fraction (EF) and LV faction shortening (FS) are tested on the day 56. After test, all animals are sacrificed and the heart, liver and kidney are weighed and collected for histology analysis.

(9) Testing for Neurodegenerative Diseases Treatment

The efficacy of berberine salt for Parkinson disease is evaluated with a C57/BL6 mice induced by 1-methyl-4-phenyl-1,2,3,6-tetrahydropyridine (MPTP). The mice are housed three per group in polycarbonate cages maintained at normal temperature (22±4° C.) with normal humidity and exposed to 12/12-h light/dark cycle with regular feed. 8-week old mice are intraperitoneally injected with MPTP at dose of 20 mg/kg/day for 7 consecutive days, while the same volume of saline is injected in vehicle model rats with same method. The mice are weighed and randomized into groups of 6 rats each: control groups, low, mid and high dose of berberine salt by intragastric gavage once daily for a total of 8 weeks treatment. And six vehicle model rats are included as normal group. Injection of MPTP induced dopaminergic neuronal death in the substantia nigra and fiber loss in the striatum, which results in impaired motor balance and coordination, as assessed by the beam walking test. By contrast, treatment with berberine enhances motor balance and coordination by preventing dopaminergic neuronal damage. Treatment with berberine also improves short-term memory by inhibiting apoptosis in the hippocampus.

In this specification and the appended claims, the singular forms "a," "an," and "the" include plural reference, unless the context clearly dictates otherwise.

Unless defined otherwise, all technical and scientific terms used herein have the same meaning as commonly understood by one of ordinary skill in the art. Although any methods and materials similar or equivalent to those described herein can also be used in the practice or testing of the present disclosure, the preferred methods and materials are now described. Methods recited herein may be carried out in any order that is logically possible, in addition to a particular order disclosed.

INCORPORATION BY REFERENCE

References and citations to other documents, such as patents, patent applications, patent publications, journals, books, papers, web contents, have been made in this disclosure. All such documents are hereby incorporated herein by reference in their entirety for all purposes. Any material, or portion thereof, that is said to be incorporated by reference herein, but which conflicts with existing definitions, statements, or other disclosure material explicitly set forth herein is only incorporated to the extent that no conflict arises between that incorporated material and the present disclosure material. In the event of a conflict, the conflict is to be resolved in favor of the present disclosure as the preferred disclosure.

EQUIVALENTS

The representative examples disclosed herein are intended to help illustrate the invention, and are not intended to, nor should they be construed to, limit the scope of the invention. Indeed, various modifications of the invention and many further embodiments thereof, in addition to those shown and described herein, will become apparent to those skilled in the art from the full contents of this document, including the examples which follow and the references to the scientific and patent literature cited herein. The following examples contain important additional information, exemplification and guidance that can be adapted to the practice of this invention in its various embodiments and equivalents thereof.

What is claimed is:

1. A pharmaceutical composition comprising a pharmaceutically acceptable excipient, carrier, or diluent and at least one berberine salt selected from the group consisting of:

(a) berberine (+)-α-lipoic acid salt having the following formula:

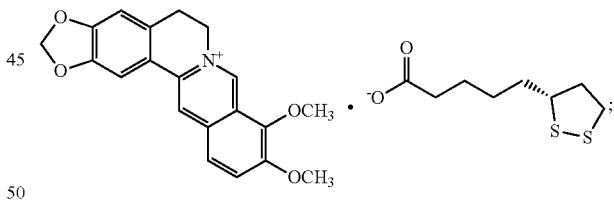

(b) berberine hydroxycitric acid salt having the following formula:

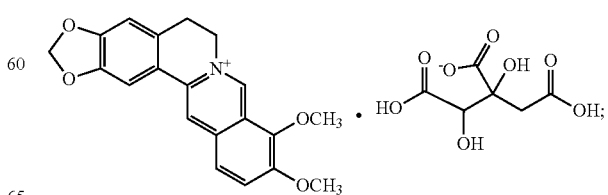

(c) berberine eicosapentaenoic acid (EPA) salt having the following formula:

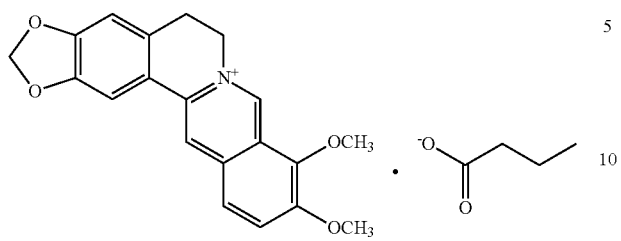

(d) berberine docosahexaenoic acid (DHA) salt having the following formula:

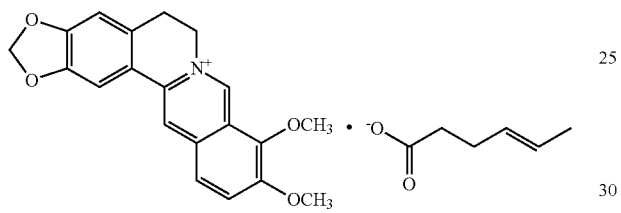

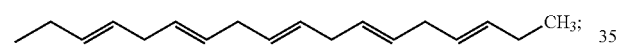

and (e) berberine ursolic acid (UA) salt having the following formula:

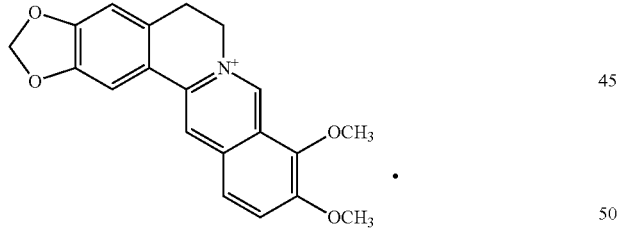

-continued

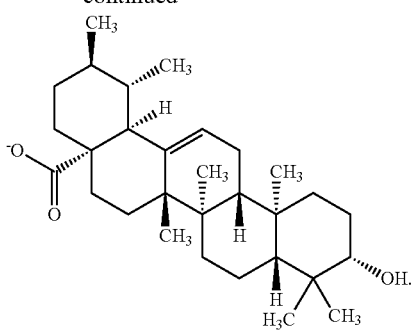

2. The pharmaceutical composition of claim 1, wherein the berberine salt is selected from the group consisting of:

(a) berberine (+)-α-lipoic acid salt having the following formula:

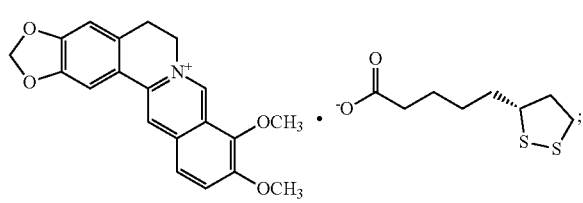

(b) berberine hydroxycitric acid salt having the following formula:

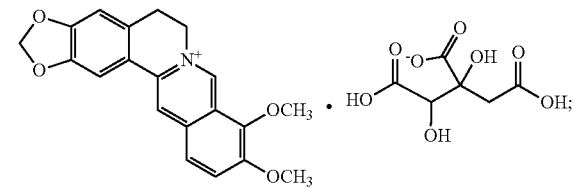

and (e) berberine ursolic acid (UA) salt having the following formula:

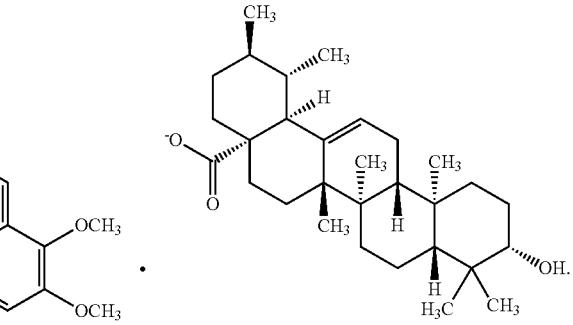

3. The pharmaceutical composition of claim 1, wherein the berberine salt is:
(c) berberine eicosapentaenoic acid (EPA) salt having the following formula:

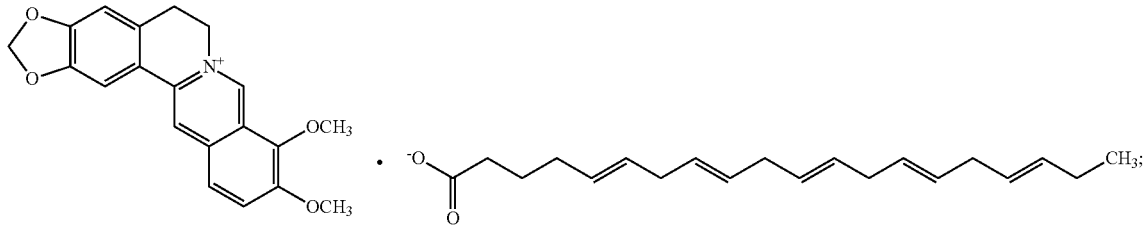

or
(d) berberine docosahexaenoic acid (DHA) salt having the following formula:

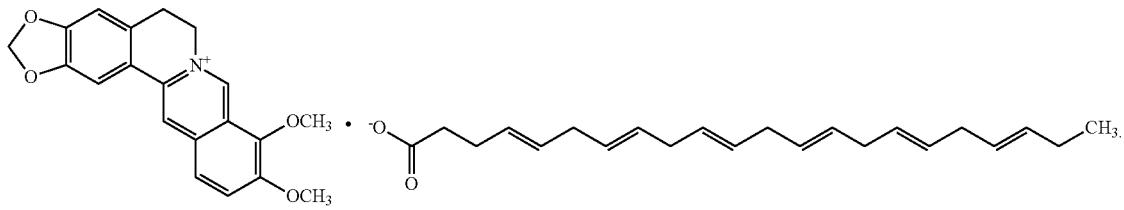

4. The pharmaceutical composition of claim 3, wherein the berberine salt is:
(c) berberine eicosapentaenoic acid (EPA) salt having the following formula:

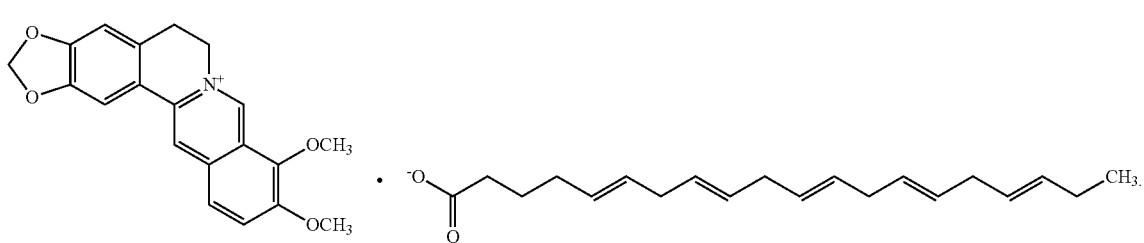

5. The pharmaceutical composition of claim 1, wherein the pharmaceutical composition further comprises at least one additional therapeutic agent selected from the group consisting of benfotiamine, chromium picolinate, vanadium, vitamin A, vitamin B12, vitamin C, vitamin D, and vitamin E.

6. A kit comprising:
(i) the pharmaceutical composition of claim 1;
(ii) at least one additional therapeutic agent selected from the group consisting of benfotiamine, chromium picolinate, vanadium, vitamin A, vitamin B12, vitamin C, vitamin D, and vitamin E; and
(iii) instructions for administering (i) and (ii) to a mammal having at least one disease or disorder selected from the group consisting of atherosclerosis, cancer, inflammation, muscle atrophy, sarcopenia, a heart disease, a liver disease, a metabolic disorder, and a neurodegenerative disease.

7. A method for treating a disease or disorder in a mammal, wherein the method comprises administering to a mammal in need thereof a therapeutically effective amount of the pharmaceutical composition of claim 1;
wherein the disease or disorder is selected from the group consisting of atherosclerosis, cancer, inflammation, muscle atrophy, sarcopenia, a heart disease, a liver disease, a metabolic disorder, and a neurodegenerative disease.

8. The method of claim 7, wherein the disease or disorder is atherosclerosis or a heart disease.

9. The method of claim 7, wherein the metabolic disorder is selected from the group consisting of cholestatic liver disease, diabetes, dyslipidemia, fatty liver disease, metabolic syndrome, nonalcoholic steatohepatitis, obesity, prediabetes, and a diabetic complication.

10. The method of claim 9, wherein the diabetes is type 1 diabetes or type 2 diabetes.

11. The method of claim 9, wherein the dyslipidemia is diabetic dyslipidemia or dyslipidemia in a statin-intolerant mammal.

12. The method of claim 9, wherein the fatty liver disease is nonalcoholic fatty liver disease.

* * * * *